(12) United States Patent
Kato et al.

(10) Patent No.: US 11,576,897 B2
(45) Date of Patent: Feb. 14, 2023

(54) THERAPEUTIC AGENT FOR NON-MOTOR SYMPTOMS ASSOCIATED WITH PARKINSON'S DISEASE

(71) Applicant: Sumitomo Pharma Co., Ltd., Osaka (JP)

(72) Inventors: Taro Kato, Osaka (JP); Satoko Shimizu, Osaka (JP)

(73) Assignee: Sumitomo Pharma Co., Ltd., Osaka (JP)

( * ) Notice: Subject to any disclaimer, the term of this patent is extended or adjusted under 35 U.S.C. 154(b) by 476 days.

(21) Appl. No.: 16/476,925

(22) PCT Filed: Jan. 12, 2018

(86) PCT No.: PCT/JP2018/000568
§ 371 (c)(1),
(2) Date: Jul. 10, 2019

(87) PCT Pub. No.: WO2018/131672
PCT Pub. Date: Jul. 19, 2018

(65) Prior Publication Data
US 2021/0299099 A1    Sep. 30, 2021

(30) Foreign Application Priority Data
Jan. 13, 2017   (JP) .............................. JP2017-004498

(51) Int. Cl.
| A61K 31/415 | (2006.01) |
| A61P 25/22 | (2006.01) |
| A61P 25/24 | (2006.01) |
| A61P 25/08 | (2006.01) |
| A61K 45/06 | (2006.01) |

(52) U.S. Cl.
CPC ............ A61K 31/415 (2013.01); A61K 45/06 (2013.01); A61P 25/08 (2018.01); A61P 25/22 (2018.01); A61P 25/24 (2018.01)

(58) Field of Classification Search
CPC ............................... A61K 31/415; A61P 25/22
See application file for complete search history.

(56) References Cited

U.S. PATENT DOCUMENTS

| 2005/0222206 A1 | 10/2005 | Cohen et al. |
| 2005/0261278 A1 | 11/2005 | Weiner et al. |
| 2006/0003996 A1 | 1/2006 | Roth et al. |
| 2006/0063757 A1 | 3/2006 | Forbes et al. |
| 2010/0004264 A1 | 1/2010 | Xiong et al. |
| 2013/0116296 A1 | 5/2013 | Sasaki et al. |

FOREIGN PATENT DOCUMENTS

| EP | 2594559 A1 * | 5/2013 | ............ A61P 25/18 |
| JP | 2006-504794 | 2/2006 | |
| JP | 2008-546691 | 12/2008 | |
| JP | 2010-505832 | 2/2010 | |
| TW | 263497 | 3/1992 | |
| WO | 2012/008528 | 1/2012 | |
| WO | 2013/157511 | 10/2013 | |

OTHER PUBLICATIONS

Caine, "I-Dopa in the treatment of parkinsonism", Clinical Pharmacology & Therapeutics, vol. 11, No. 6, pp. 789-801 (1970).*
Extended Search Report dated Aug. 27, 2020 in corresponding European Patent Application No. 18739127.1.
International Search Report dated Apr. 10, 2018 in International (PCT) Application No. PCT/JP2018/000568.
Written Opinion of International Searching Authority dated Apr. 10, 2018 in International (PCT) Application No. PCT/JP2018/000568.
Rabey, "Hallucinations and psychosis in Parkinson's disease", Parkisonism and Related Disorders, vol. 155, pp. S105-S110, 2009.
Breier et al., "Olanzapine in the Treatment of Dopamimetic-Induced Psychosis in Patients with Parkinson's Disease", Biological Psychiatry, vol. 52, No. 5, pp. 438-445, 2002.
Ondo et al., "Olanzapine Treatment for Dopaminergic-Induced Hallucinations", Movement Disorders, vol. 17, No. 5, pp. 1031-1035, 2002.
Gòmez-Esteban et al., "Use of Ziprasidone in Parkinsonian Patients With Psychosis", Clinical Neuropharmacology, vol. 28, No. 3, pp. 111-114, 2005.
Pollak et al., "Clozapine in drug induced psychosis in Parkinson's disease: a randomised, placebo controlled study with open follow up", Journal of Neurology Neurosurgery Psychiatry, vol. 75, No. 5, pp. 689-695, 2004.

(Continued)

Primary Examiner — Kevin E Weddington
(74) Attorney, Agent, or Firm — Wenderoth, Lind & Ponack, L.L.P.

(57) ABSTRACT

The purpose of the present invention is to provide: a therapeutic agent or a recurrence preventive agent for serotonergic system- or dopaminergic system-related diseases, in particular, mental dysfunction symptoms and other non-motor symptoms of Parkinson's disease; and a method for treating the aforesaid symptoms or preventing the recurrence of the same. A compound represented by formula (1) [wherein each symbol is as defined in the description] or a pharmaceutically acceptable salt thereof can exhibit an effect of treating serotonergic system- or dopaminergic system-related diseases, in particular, mental dysfunction symptoms and other non-motor symptoms of Parkinson's disease and/or an effect of preventing the recurrence of the same.

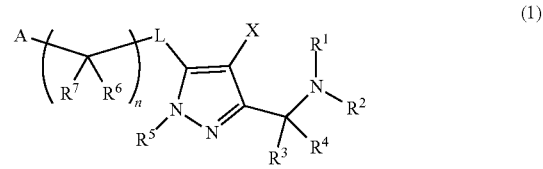

(1)

24 Claims, 3 Drawing Sheets

(56) References Cited

OTHER PUBLICATIONS

Cummings et al., "Pimavanserin for patients with Parkinson's disease psychosis: a randomised, placebo-controlled phase 3 trial", The Lancet, vol. 383, pp. 533-540, 2014.
Vanover et al., "Pharmacological and Behavioral Profile of N-(4-Fluorophenylmethyl)-N-(1-methylpiperidin-4-yl)-N'-(4-(2-methylpropyloxy)phenylmethyl) Carbamide (2R,3R)-Dihydroxybutanedioate (2:1) (ACP-103), a Novel 5-Hydroxytryptamine$_{2A}$ Receptor Inverse Agonist", The Journal of Pharmacology and Experimental Therapeutics, JPET, vol. 317, pp. 910-918, 2006.
Martinez-Martin et al., "Assessing the non-motor symptoms of Parkinson's disease: MDS-UPDRS and NMS Scale", European Journal of Neurology, vol. 22, pp. 37-43, 2015.
Duncan et al., "Health-Related Quality of Life in Early Parkinson's Disease: The Impact of Nonmotor Symptoms", Movement Disorder, vol. 29, No. 2, pp. 195-202, 2014.
Garcia-Borreguero et al., "Parkinson's disease and sleep", Sleep Medicine Reviews, vol. 7, No. 2, pp. 115-129, 2003.
Emre, "Dementia associated with Parkinson's disease", The Lancet Neurology, vol. 2, pp. 229-237, 2003.
Oberndorfer et al., "Effects of Selective Serotonin Reuptake Inhibitors on Objective and Subjective Sleep Quality", Neuropsychobiology, vol. 42, pp. 69-81, 2000.
Landolt et al., "Antagonism of serotonergic 5-HT$_{2A/2C}$ receptors: mutual improvement of sleep, cognition and mood?", European Journal of Neuroscience, vol. 29, pp. 1795-1809, 2009.
Avlar et al, "Improving Temporal Cognition by Enhancing Motivation", Behavoral Neuroscience, vol. 129, No. 5, pp. 576-588, 2015.
Marek et al., "Synergistic Action of 5-HT$_{2A}$ Antagonists and Selective Serotonin Reuptake Inhibitors in Neuropsychiatric Disorders", Neuropsychopharmacology, vol. 28, pp. 402-412, 2003.
Rénéric et al., "In the rat forced swimming test, chronic but not subacute administration of dual 5-HT/NA antidepressant treatments may produce greater effects than selective drugs", Behavioural Brain Research, vol. 136, pp. 521-532, 2002.
Andersen et al., "Anti-depressive treatment in Parkinson's disease: A Controlled Trial of the Effect of Nortriptyline in Patients With Parkinson's Disease Treated With L-DOPA", Acta Neurologica Scandinavica, vol. 62, No. 4, pp. 210-219, 1980.
Vijayapandi et al., "Biphasic Effects of Losartan Potassium on Immobility in Mice", Yakugaku Zasshi, vol. 125 No. 8, pp. 653-657, 2005.
Hanagasi et al., "Treatment of behavioural symptoms and dementia in Parkinson's disease", Fundamental & Clinical Pharmacology, vol. 19, pp. 133-146, 2005.
Clinical Practice Guideline for Parkinson's disease 2011 edited by Japanese Society of Neurology.
Cussac, D. et al., "Antagonist properties of the novel antipsychotic, SI6924, at cloned, human serotonin 5-HT$_{2c}$ receptors: a parallel phosphatidylinositol and calcium accumulation comparison with clozapine and haloperidol", Naunyn-Schmiedeberg's Arch. Pharmacol., 2000, vol. 361, pp. 549-554.

* cited by examiner

[Fig. 1]
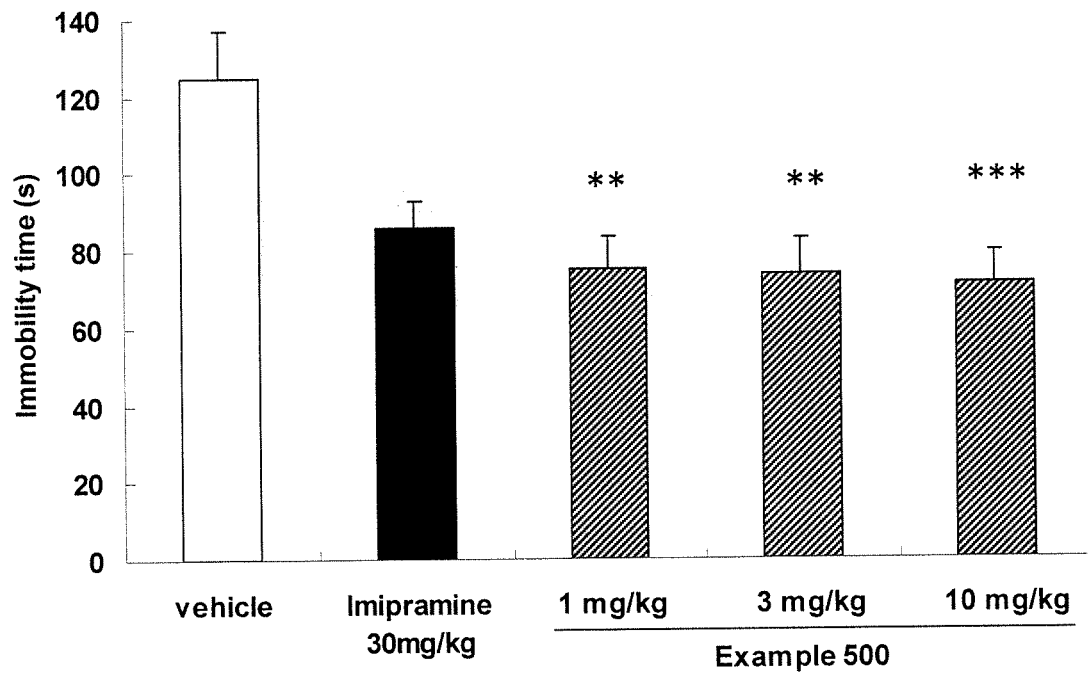
[Fig. 2]
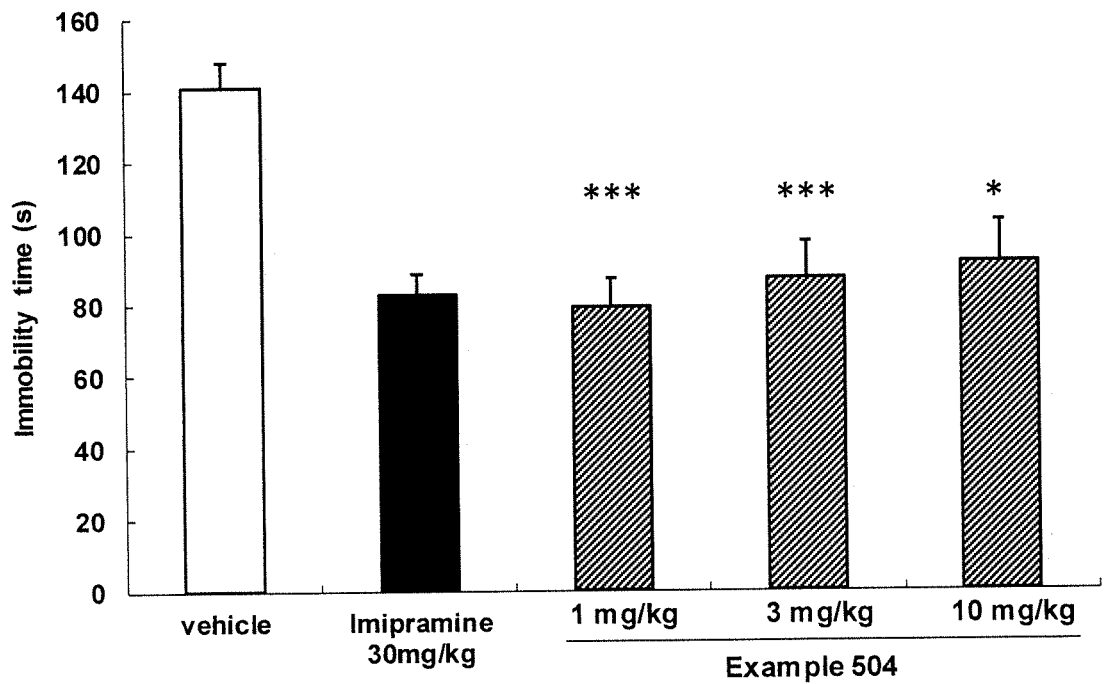

[Fig. 3]
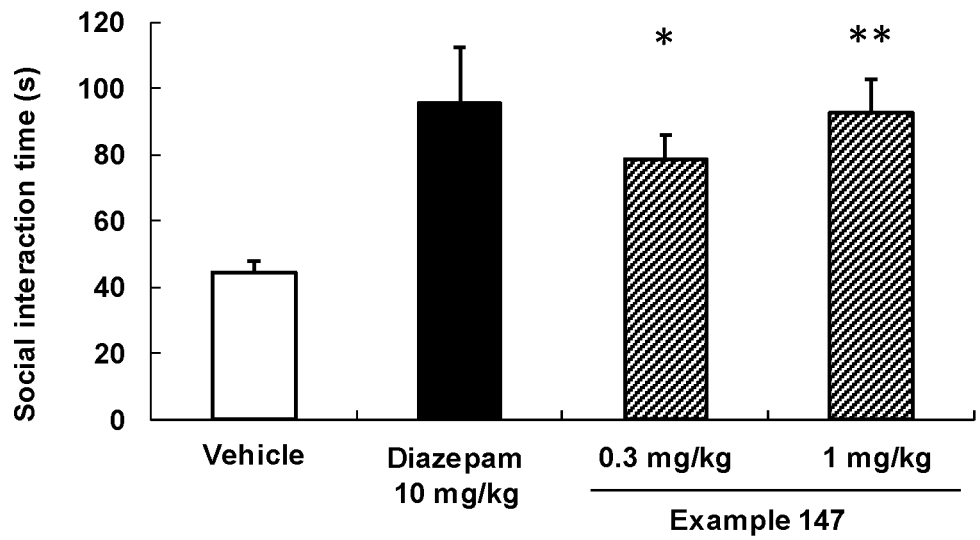
[Fig. 4]
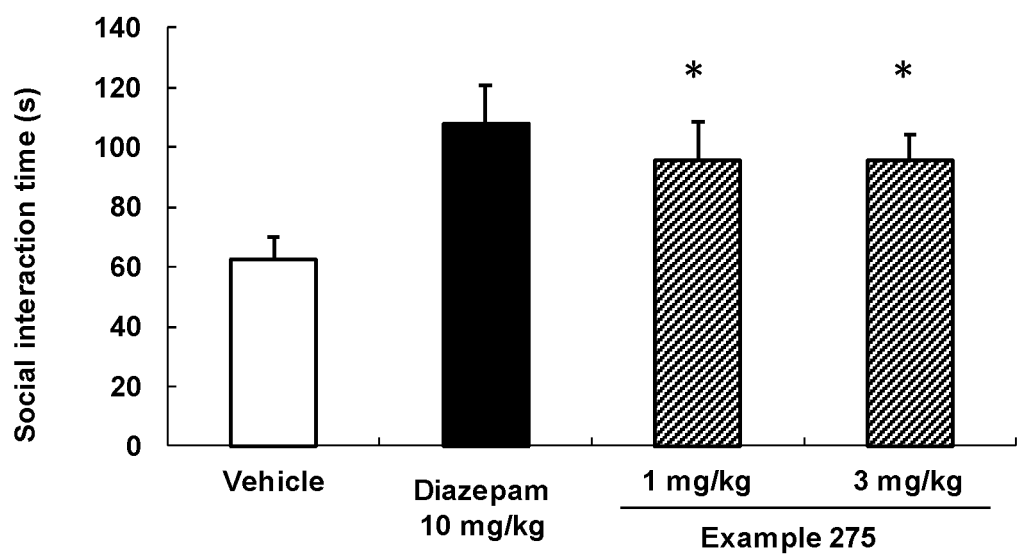

[Fig. 5]
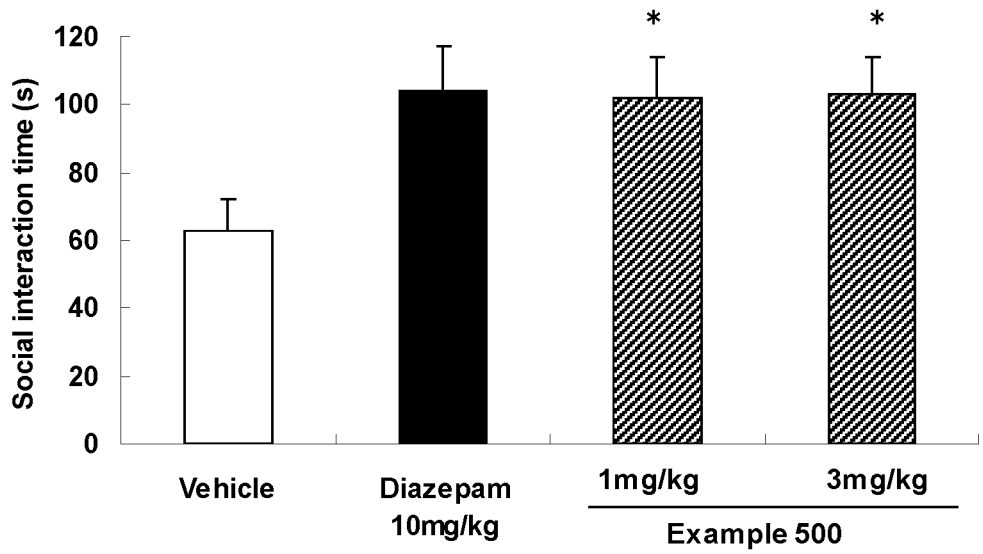
[Fig. 6]
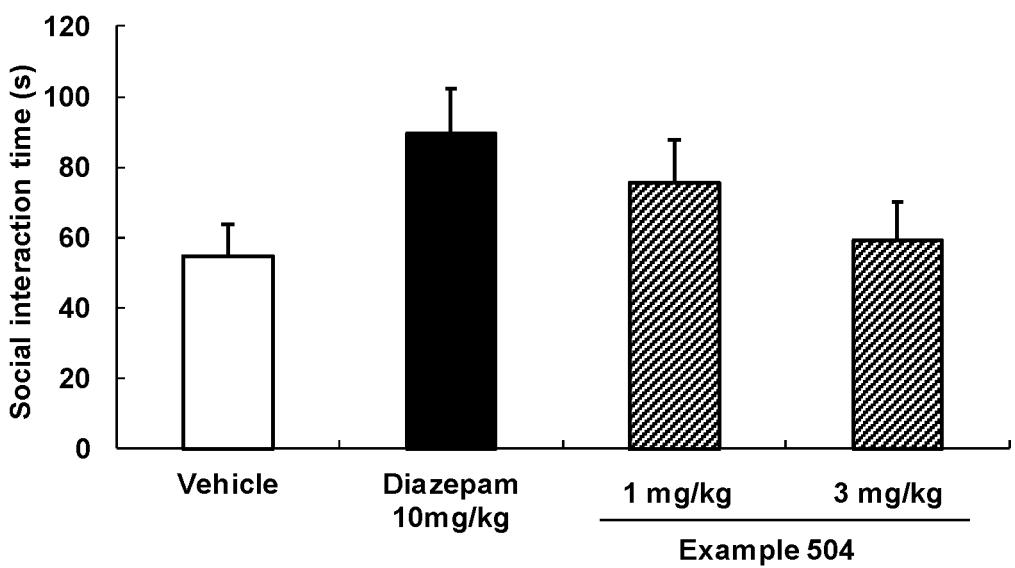

US 11,576,897 B2

THERAPEUTIC AGENT FOR NON-MOTOR SYMPTOMS ASSOCIATED WITH PARKINSON'S DISEASE

TECHNICAL FIELD

The present invention relates to treatment for non-motor symptoms associated with Parkinson's disease (also referred to as "PD" hereinafter). Specifically, the present invention relates to a medicament or drug for treating psychopathic symptoms (also referred to as "psychosis" hereinafter) and other non-motor symptoms associated with Parkinson's disease or preventing a relapse thereof, comprising as an active ingredient a compound of Formula (1) as below or a pharmaceutically acceptable salt thereof, and a method for treating or preventing a relapse of the same.

BACKGROUND ART

Parkinson's disease is a progressive neurodegenerative disease based on dopamine neuron degeneration in mensencephalic substantia nigra. A prominent symptom of Parkinson's disease includes motor disorder such as tremor at rest, muscular rigidity, immobility, hypokinesis, and impairment of postural reflexes. In addition to this, various non-motor symptoms are also observed. Non-motor symptoms include various conditions such as sleep-wake cycle abnormity (sleep disorder), cognitive dysfunction, psychopathic symptoms such as hallucination and delusion, depressive symptoms, anxiety symptoms, autonomic disorder, pain, edema, and impaired sense of smell, each of which increases in the expression frequency or becomes severe with progression of Parkinson's disease.

It is known that about 30% of PD patients show psychopathic symptoms and these symptoms greatly affect the quality of life (QOL). The symptoms constitute a primary factor in prolonged hospitalization or admission to a nursing home, which also leads to increase of caregiver burden (Non Patent Literature 1).

Psychosis in PD patients may be induced with a medicament for treating motor symptoms such as dopamine replacement drugs and dopamine receptor agonists. In the case where such symptoms are presented, it is common to first reduce the dose of a dopamine replacement drug or dopamine receptor agonist or discontinue the administration thereof. Such treatment, however, has not necessarily ameliorated the symptoms, and it has become a problem that such treatment involves exacerbations of a prominent symptom, motor symptoms. In the case where the reduction of dose of a dopamine replacement drug or dopamine receptor agonist or discontinuation of administration thereof does not result in amelioration of the symptoms, an atypical antipsychotic drug has been attempted to be administered so far. Atypical antipsychotic drugs may have the risk of exacerbations of motor symptoms due to their dopamine $D_2$ receptor antagonism (Non Patent Literature 2, Non Patent Literature 3, and Non Patent Literature 4), and in addition, no atypical antipsychotic drug has been demonstrated in long-term efficacy on psychopathic symptoms in Parkinson's disease in randomized controlled studies so far. Only clozapine has been reported to ameliorate psychopathic symptoms without exacerbations of motor symptoms in lower doses in a randomized controlled study (Non Patent Literature 5). Clozapine has not been approved for the symptoms as an indication in terms of the pharmaceutical affairs and have concerns for a serious adverse effect, agranulocytosis, and therefore, its off-label use requires severe watchful waiting.

Patent Literature 1 discloses that pyrazole compounds are successful in treating depression or anxiety, but it does not disclose specific effects on psychopathic symptoms and other non-motor symptoms such as sleep disorder in various diseases accompanied by Parkinson's disease or cognitive dysfunction.

After a long period of no approved drug with an indication of psychopathic symptoms associated with Parkinson's disease, serotonin 5-$HT_{2A}$ receptor inverse agonist, pimavanserin, was first approved for the symptoms as an indication in the United States in 2016. Unlike existing antipsychotic drugs, adverse effects of exacerbations of motor symptoms have not been reported for this drug (Non Patent Literature 6). A primary pharmacological activity of pimavanserin is serotonin 5-$HT_{2A}$ receptor inverse agonism, and in addition to that, it also shows serotonin 5-$HT_{2C}$ receptor inverse agonism (Non Patent Literature 7).

In Parkinson's disease patients, multiple non-motor symptoms frequently occur with motor symptoms, and it is reported that depressive symptoms, anxiety symptoms, sleep disorder, and cognitive dysfunction are accompanied in about 60%, about 50%, about 60%, and about 50%, respectively, of patients (Non Patent Literature 8). These non-motor symptoms lower QOL of Parkinson's disease patients markedly (Non Patent Literature 9), but no drug has been approved for the indication of depressive symptoms, anxiety symptoms, sleep disorder, and cognitive dysfunction associated with Parkinson's disease so far. Various antidepressants, anxiolytic drugs, hypnotics, and antidementia drugs, etc. are currently used for off-label use as supportive care, but various adverse effects such as oversedation, daytime hypersomnia, exacerbations of motor symptoms, tremor, and circulatory adverse effects become problematic. Due to few evidence in massive clinical trials for any of the symptoms, no drug has been confirmed for long-term efficacy (Non Patent Literature 10, Non Patent Literature 11, and Non Patent Literature 12). Thus, a drug with extensive therapeutic effects on non-motor symptoms associated with Parkinson's disease and lower risks of adverse effects has been desired to be developed.

An antidepressant, selective serotonin reuptake inhibitor (SSRI: the primary pharmacological action is serotonin transporter (SERT) inhibitory action), shows antidepressant effects or anxiolytic effects (Patent Literature 1). In addition, SSRIs have been reported recently to be involved in sleep-wake cycle regulation (Non Patent Literature 13). Serotonin 5-$HT_{2A/2C}$ receptor antagonists or inverse agonists have been indicated to ameliorate cognitive function in addition to the antidepressant effect, anxiolytic effect, and the action of ameliorating sleep disorder (Non Patent Literature 14 and Non Patent Literature 15). It has also been reported that compounds having both SERT inhibitory action and serotonin 5-$HT_{2A}$ receptor antagonism are suitable for improvement of sleep quality (Non Patent Literature 13).

It has been known that a combination of SERT inhibitory action and serotonin 5-$HT_{2C}$ receptor antagonism (including inverse agonist action) enhances pharmacological actions such as antidepressant effects and anxiolytic effects (Patent Literature 1). It has also been reported that a combination of serotonin 5-$HT_{2A}$ receptor antagonism (including inverse agonist action) with SERT inhibitory action enhances each of the pharmacological actions (Non Patent Literature 16).

PATENT LITERATURES

[Patent Literature 1] WO 2012/008528

NON PATENT LITERATURES

[Non Patent Literature 1] J. M. Rabey, Parkisonism and related disorder 155. 2009. S105-1110
[Non Patent Literature 2] A. Breier, Biol. Psychiatry. 2002. 52(5).438-445
[Non Patent Literature 3] W. G. Ondo, Mov. Disord. 2002. 17(5). 1031-1035
[Non Patent Literature 4] J. C. Gomez-Esteban, Clin. Neuropharmacol. 2005. 28(7). 111-114
[Non Patent Literature 5] P. Pollak, J. Neurol. Neurosurge. Psychiatry. 2004. 75(5). 689-695
[Non Patent Literature 6] J. Cummings, Lancet 2014; 383: 533-40
[Non Patent Literature 7] K. E. Vanovar, J. PHARMACOL. EXP. THERAPEUTICS: JPET 317:910-918, 2006
[Non Patent Literature 8] P. Martinez-Mertin, Eur. J. Neurology. 2015. 22. 37-43
[Non Patent Literature 9] W. Duncun, Movement Disorder. 2014. 29(2). 195-202
[Non Patent Literature 10] Clinical Practice Guideline for Parkinson's disease 2011 edited by Japanese Society of Neurology
[Non Patent Literature 11] D. Garcia-Borreguero, Sleep Medicine Reviews, Vol. 7, No. 2, pp 115-129, 2003
[Non Patent Literature 12] M. Emre, Lancet Neurology 2003; 2: 229-37
[Non Patent Literature 13] S. Oberndorfer, Neuropsychobiology 2000; 42: 69-81
[Non Patent Literature 14] H. P. Landolt, European Journal of Neuroscience, Vol. 29, pp. 1795-1809, 2009
[Non Patent Literature 15] B. Avlar, Behav Neurosci. 2015129(5): 576-588
[Non Patent Literature 16] G. J. Marek, Neuropsychopharmacology (2003) 28, 402-412
[Non Patent Literature 17] J. P. Reneric, Behavioural Brain Research 136 (2002) 521-532
[Non Patent Literature 18] J. Andersen, Acta Neural Scand. 1980. 62(4). 210-219
[Non Patent Literature 19] P. Vijayapandi, YAKUGAKU ZASSHI. 2005. 125(8). 653-657
[Non Patent Literature 20] H. A. Hanagasi, Fundamental & Clinical Pharmacology. 2005. 19. 133-146

SUMMARY OF INVENTION

Problems to be Solved by the Invention

An object of the present invention is to provide a medicament for treating psychopathic symptoms and other non-motor symptoms associated with diseases mediated by serotonergic system or dopaminergic system, particularly Parkinson's disease, or preventing a relapse thereof and a method for treating the symptoms or preventing a relapse thereof.

Means of Solving the Problems

The present inventors have extensively studied to solve the above problems and then have found that a compound of Formula (1) below or a pharmaceutically acceptable salt thereof (also referred to as "the present compound" hereinafter) is useful for treating psychopathic symptoms and other non-motor symptoms associated with diseases mediated by serotonergic system or dopaminergic system, particularly Parkinson's disease, and/or preventing a relapse thereof. Based upon the findings, the present invention has been completed.

Specifically, the present inventors have focused on pharmacological profiles of pimavanserin (wherein the primary pharmacological action is serotonin $5\text{-HT}_{2A/2C}$ receptor inverse agonist action) currently used for treatment of psychopathic symptoms associated with Parkinson's disease and selective serotonin reuptake inhibitors (SSRI: the primary pharmacological action is serotonin transporter (SERT) inhibitory action) used for treatment of depressive symptoms or anxiety symptoms associated with various diseases, and then have found that the present compound has serotonin $5\text{-HT}_{2A}$ receptor antagonism or inverse agonist action, serotonin transporter (SERT) inhibitory action, and serotonin $5\text{-HT}_{2C}$ receptor antagonism or inverse agonist action simultaneously, resulting in the efficacy for treating psychopathic symptoms and other non-motor symptoms associated with diseases mediated by serotonergic system or dopaminergic system, particularly Parkinson's disease, and/or preventing a relapse thereof.

Specifically, the present invention encompasses the following embodiments.

[1] A medicament for treating non-motor symptoms associated with Parkinson's disease or preventing a relapse thereof, comprising a compound of the following Formula (1):

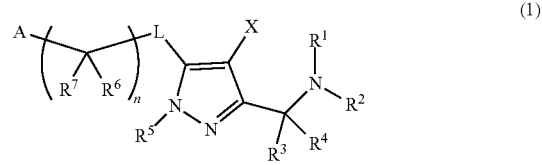

wherein $R^1$ and $R^2$ are each independently hydrogen atom, a $C_{1-6}$ alkyl group optionally substituted with 1 to 3 deuterium atoms, or a $C_{3-8}$ cycloalkyl group, $R^3$ and $R^4$ are each independently hydrogen atom, deuterium atom, or a $C_{1-6}$ alkyl group, $R^5$ is an optionally-substituted $C_{4-7}$ alkyl group or $-(CR^8R^9)_r\text{-E}$, $R^6$ and $R^7$ are each independently hydrogen atom, deuterium atom, fluorine atom, or an optionally-substituted $C_{1-6}$ alkyl group, $R^8$ and $R^9$ are each independently hydrogen atom, fluorine atom, or an optionally-substituted $C_{1-6}$ alkyl group, A is an optionally-substituted $C_{6-10}$ aryl group or an optionally-substituted 5- to 10-membered heteroaryl group, r is 1, 2, 3, or 4, E is an optionally-substituted $C_{3-8}$ cycloalkyl group, an optionally-substituted $C_{4-8}$ cycloalkenyl group, an optionally-substituted 5- to 10-membered saturated heterocyclic group wherein the saturated heterocyclic group comprises 1 to 3 heteroatoms independently selected from the group consisting of oxygen atom and sulfur atom as a constituent atom of the ring, an optionally-substituted $C_6$-aryl group, or an optionally-substituted 5- to 10-membered heteroaryl group, L is oxygen atom, sulfur atom, or $-NR^{10}-$, n is 1, 2, or 3, $R^{10}$ is hydrogen atom, a $C_{1-6}$ alkyl group, or a $C_{3-8}$ cycloalkyl group, X is hydrogen atom, a $C_{1-6}$ alkyl group optionally substituted with fluorine atom, or a halogen atom, a substituent on the optionally-substituted $C_{6-10}$ aryl group and optionally-substituted 5- to 10-membered heteroaryl group is 1 to 2 substituents each independently selected from the group consisting of a halogen atom; a $C_{1-6}$ alkyl group optionally substituted with fluorine atom; a $C_{1-6}$ alkyloxy group optionally substituted with fluorine atom; hydroxy group; a $C_{1-6}$ alkylthio group; a $C_{6-10}$ aryloxy group; a $C_{6-10}$ arylthio group; cyano group; —$CO_2R^{11}$; —$SO_2R^{11}$; —$NR^{10}SO_2R^{11}$; —$OSO_2R^{11}$; —$COR^{12}$; —$SO_2NR^{12}R^{13}$; —$CONR^{12}R^{13}$; —$NR^{12}R^{13}$; —$NR^{10}CONR^{12}R^{13}$; —$NR^{10}COR^{12}$; —$CR^{12}$=$N(OR^{11})$; oxime group; a $C_{3-8}$ cycloalkyl group; a $C_{6-10}$ aryl group; and a 5- to 10-membered heteroaryl group, wherein $R^{10}$ is defined as above, $R^{11}$ is a $C_{1-6}$ alkyl group, a $C_{3-8}$ cycloalkyl group, a $C_{6-10}$ aryl group, or a 5- to 10-membered heteroaryl group, $R^{12}$ and $R^{13}$ are each independently hydrogen atom, a $C_{1-6}$ alkyl group, a $C_{3-8}$ cycloalkyl group, a $C_{6-10}$ aryl group, or a 5- to 10-membered heteroaryl group, and the $C_{6-10}$ aryl group and 5- to 10-membered heteroaryl group in $R^{11}$, $R^{12}$, and $R^{13}$ may be optionally further substituted with a halogen atom, a $C_{1-6}$ alkyl group, hydroxy group, or a $C_{1-6}$ alkyloxy group, a substituent on the optionally-substituted $C_{1-6}$ alkyl group and optionally-substituted $C_{4-7}$ alkyl group is 1 to 2 substituents each independently selected from the group consisting of fluorine atom; hydroxy group; and a $C_{1-6}$ alkyloxy group optionally substituted with fluorine atom, and a substituent on the optionally-substituted $C_{3-8}$ cycloalkyl group, optionally-substituted $C_{4-8}$ cycloalkenyl group, and optionally-substituted 5- to 10-membered saturated heterocyclic group is 1 to 2 substituents each independently selected from the group consisting of fluorine atom; a $C_{1-6}$ alkyl group optionally substituted with fluorine atom; hydroxy group; and a $C_{1-6}$ alkyloxy group optionally substituted with fluorine atom, or a pharmaceutically acceptable salt thereof.

[2] The medicament according to [1], wherein $R^1$ and $R^2$ are each independently hydrogen atom, methyl group, or methyl group substituted with 1 to 3 deuterium atoms, $R^3$ is hydrogen atom, deuterium atom, or methyl group, and $R^4$ is hydrogen atom or deuterium atom.

[3] The medicament according to [1] or [2], wherein A is an optionally-substituted $C_{6-10}$ aryl group.

[4] The medicament according to any one of [1] to [3], wherein X is hydrogen atom.

[5] The medicament according to any one of [1] to [4], wherein L is oxygen atom.

[6] The medicament according to any one of [1] to [5], wherein n is 1.

[7] The medicament according to any one of [1] to [6], wherein $R^1$, $R^3$, and $R^4$ are hydrogen atom and $R^2$ is methyl group.

[8] The medicament according to any one of [1] to [7], wherein $R^6$ and $R^7$ are each independently hydrogen atom or deuterium atom and $R^8$ and $R^9$ are hydrogen atom.

[9] The medicament according to any one of [1] to [8], wherein E is an optionally-substituted $C_{3-8}$ cycloalkyl group, an optionally-substituted 5- to 10-membered saturated heterocyclic group wherein the saturated heterocyclic group comprises 1 to 3 oxygen atoms as a constituent atom of the ring, or optionally-substituted phenyl group.

[10] The medicament according to any one of [1] to [9], wherein E is an optionally-substituted $C_{3-8}$ cycloalkyl group.

[11] The medicament according to any one of [1] to [10], wherein r is 1 or 2.

[12] The medicament according to any one of [1] to [11], wherein $R^5$ is an optionally-substituted $C_{4-7}$ alkyl group.

[13] The medicament according to [1], wherein the compound of Formula (1) is any one of the following compounds or pharmaceutically acceptable salts thereof:

1-[5-(benzyloxy)-1-(cyclohexylmethyl)-1H-pyrazol-3-yl]-N-methylmethanamine; Example 5

1-{1-(cyclohexylmethyl)-5-[(2-fluorobenzyl)oxy]-1H-pyrazol-3-yl}-N-methylmethanamine; Example 20

1-{1-(cyclohexylmethyl)-5-[(3-fluorobenzyl)oxy]-1H-pyrazol-3-yl}-N-methylmethanamine; Example 21

1-{1-(cyclohexylmethyl)-5-[(4-fluorobenzyl)oxy]-1H-pyrazol-3-yl}-N-methylmethanamine; Example 22

1-{5-[(2-chlorobenzyl)oxy]-1-(cyclohexylmethyl)-1H-pyrazol-3-yl}-N-methylmethanamine; Example 23

1-{5-[(3-chlorobenzyl)oxy]-1-(cyclohexylmethyl)-1H-pyrazol-3-yl}-N-methylmethanamine; Example 24

1-{1-(cyclohexylmethyl)-5-[(2-methylbenzyl)oxy]-1H-pyrazol-3-yl}-N-methylmethanamine; Example 26

1-{1-(cyclohexylmethyl)-5-[(3-methylbenzyl)oxy]-1H-pyrazol-3-yl}-N-methylmethanamine; Example 27

1-{1-(cyclohexylmethyl)-5-[(2,4-difluorobenzyl)oxy]-1H-pyrazol-3-yl}-N-methylmethanamine; Example 29

1-{5-[(2-chloro-4-fluorobenzyl)oxy]-1-(cyclohexylmethyl)-1H-pyrazol-3-yl}-N-methylmethanamine; Example 30

1-{1-(cyclohexylmethyl)-5-[(4-fluoro-2-methylbenzyl)oxy]-1H-pyrazol-3-yl}-N-methylmethanamine; Example 31

1-{1-(cyclohexylmethyl)-5-[(2,5-difluorobenzyl)oxy]-1H-pyrazol-3-yl}-N-methylmethanamine; Example 33

1-{5-[(5-chloro-2-fluorobenzyl)oxy]-1-(cyclohexylmethyl)-1H-pyrazol-3-yl}-N-methylmethanamine; Example 34

1-{1-(cyclohexylmethyl)-5-[(2-fluoro-5-methylbenzyl)oxy]-1H-pyrazol-3-yl}-N-methylmethanamine; Example 35

1-{5-[(2-chloro-5-fluorobenzyl)oxy]-1-(cyclohexylmethyl)-1H-pyrazol-3-yl}-N-methylmethanamine; Example 37

1-{1-(cyclohexylmethyl)-5-[(2,5-dichlorobenzyl)oxy]-1H-pyrazol-3-yl}-N-methylmethanamine; Example 38

1-{5-[(2-chloro-5-methylbenzyl)oxy]-1-(cyclohexylmethyl)-1H-pyrazol-3-yl}-N-methylmethanamine; Example 39

1-[5-(benzyloxy)-1-(cyclopentylmethyl)-1H-pyrazol-3-yl]-N-methylmethanamine; Example 4

1-{1-(cyclopentylmethyl)-5-[(2-fluorobenzyl)oxy]-1H-pyrazol-3-yl}-N-methylmethanamine; Example 135

1-{1-(cyclopentylmethyl)-5-[(3-fluorobenzyl)oxy]-1H-pyrazol-3-yl}-N-methylmethanamine; Example 136

1-{1-(cyclopentylmethyl)-5-[(4-fluorobenzyl)oxy]-1H-pyrazol-3-yl}-N-methylmethanamine; Example 137

1-{5-[(2-chlorobenzyl)oxy]-1-(cyclopentylmethyl)-1H-pyrazol-3-yl}-N-methylmethanamine; Example 138

1-{5-[(3-chlorobenzyl)oxy]-1-(cyclopentylmethyl)-1H-pyrazol-3-yl}-N-methylmethanamine; Example 139

1-{1-(cyclopentylmethyl)-5-[(2-methylbenzyl)oxy]-1H-pyrazol-3-yl}-N-methylmethanamine; Example 141

1-{1-(cyclopentylmethyl)-5-[(3-methylbenzyl)oxy]-1H-pyrazol-3-yl}-N-methylmethanamine; Example 142

1-{1-(cyclopentylmethyl)-5-[(2,4-difluorobenzyl)oxy]-1H-pyrazol-3-yl}-N-methylmethanamine; Example 144

1-{5-[(2-chloro-4-fluorobenzyl)oxy]-1-(cyclopentylmethyl)-1H-pyrazol-3-yl}-N-methylmethanamine; Example 145

1-{1-(cyclopentylmethyl)-5-[(4-fluoro-2-methylbenzyl)oxy]-1H-pyrazol-3-yl}-N-methylmethanamine; Example 146

1-{1-(cyclopentylmethyl)-5-[(2,5-difluorobenzyl)oxy]-1H-pyrazol-3-yl}-N-methylmethanamine; Example 147

1-{5-[(5-chloro-2-fluorobenzyl)oxy]-1-(cyclopentylmethyl)-1H-pyrazol-3-yl}-N-methylmethanamine; Example 148

1-{1-(cyclopentylmethyl)-5-[(2-fluoro-5-methylbenzyl)oxy]-1H-pyrazol-3-yl}-N-methylmethanamine; Example 149

1-{5-[(2-chloro-5-fluorobenzyl)oxy]-1-(cyclopentylmethyl)-1H-pyrazol-3-yl}-N-methylmethanamine; Example 150

1-{1-(cyclopentylmethyl)-5-[(2,5-dichlorobenzyl)oxy]-1H-pyrazol-3-yl}-N-methylmethanamine; Example 151

1-{5-[(2-chloro-5-methylbenzyl)oxy]-1-(cyclopentylmethyl)-1H-pyrazol-3-yl}-N-methylmethanamine; Example 152

1-[5-(benzyloxy)-1-(3,3-dimethylbutyl)-1H-pyrazol-3-yl]-N-methylmethanamine; Example 264

1-{5-[(3-chlorobenzyl)oxy]-1-(3,3-dimethylbutyl)-1H-pyrazol-3-yl}-N-methylmethanamine; Example 265

1-{5-[(2,5-difluorobenzyl)oxy]-1-(3,3-dimethylbutyl)-1H-pyrazol-3-yl}-N-methylmethanamine; Example 266

1-{5-[(5-chloro-2-fluorobenzyl)oxy]-1-(3,3-dimethylbutyl)-1H-pyrazol-3-yl}-N-methylmethanamine; Example 267

1-[5-(benzyloxy)-1-(3-methylbutyl)-1H-pyrazol-3-yl]-N-methylmethanamine; Example 268

1-{5-[(2,5-difluorobenzyl)oxy]-1-(3-methylbutyl)-1H-pyrazol-3-yl}-N-methylmethanamine; Example 269

1-{5-[(5-chloro-2-fluorobenzyl)oxy]-1-(3-methylbutyl)-1H-pyrazol-3-yl}-N-methylmethanamine; Example 270

1-{5-[(2,5-difluorobenzyl)oxy]-1-(3-methoxy-3-methylbutyl)-1H-pyrazol-3-yl}-N-methylmethanamine; Example 274

1-{5-[(5-chloro-2-fluorobenzyl)oxy]-1-(3-methoxy-3-methylbutyl)-1H-pyrazol-3-yl}-N-methylmethanamine; Example 275

1-{1-(cyclopentylmethyl)-5-[(2,4,5-trifluorobenzyl)oxy]-1H-pyrazol-3-yl}-N-methylmethanamine; Example 280

1-{1-(cyclohexylmethyl)-5-[(2,4,5-trifluorobenzyl)oxy]-1H-pyrazol-3-yl}-N-methylmethanamine;

1-{1-(2-cyclopentylethyl)-5-[(2,5-difluorobenzyl)oxy]-1H-pyrazol-3-yl}-N-methylethanamine; Example 315

N-methyl-1-{1-(3-methylbutyl)-5-[(2,4,5-trifluorobenzyl)oxy]-1H-pyrazol-3-yl}methanamine; Example 283

1-{1-(3,3-dimethylbutyl)-5-[(2,4,5-trifluorobenzyl)oxy]-1H-pyrazol-3-yl}-N-methylmethanamine; Example 284

1-{1-(4-fluorobenzyl)-5-[(2-fluorobenzyl)oxy]-1H-pyrazol-3-yl}-N-methylmethanamine; Example 218

1-{5-[(2,5-difluorobenzyl)oxy]-1-(4-fluorobenzyl)-1H-pyrazol-3-yl}-N-methylmethanamine; Example 219

1-{1-(4-fluorobenzyl)-5-[(2,4,5-trifluorobenzyl)oxy]-1H-pyrazol-3-yl}-N-methylmethanamine;

1-{5-[(2-fluorobenzyl)oxy]-1-(4-methylbenzyl)-1H-pyrazol-3-yl}-N-methylmethanamine; Example 228

1-{5-[(2,5-difluorobenzyl)oxy]-1-(4-methylbenzyl)-1H-pyrazol-3-yl}-N-methylmethanamine; Example 230

N-methyl-1-{1-(4-methylbenzyl)-5-[(2,4,5-trifluorobenzyl)oxy]-1H-pyrazol-3-yl}methanamine; Example 286

1-{5-[(2,5-difluorobenzyl)oxy]-1-(4-methoxybenzyl)-1H-pyrazol-3-yl}-N-methylmethanamine;

1-{1-(4-methoxybenzyl)-5-[(2,4,5-trifluorobenzyl)oxy]-1H-pyrazol-3-yl}-N-methylmethanamine; Example 285

1-{5-[(5-chloro-2-fluorobenzyl)oxy]-1-(cyclopropylmethyl)-1H-pyrazol-3-yl}-N-methylmethanamine; Example 131

1-{5-[(4-fluorobenzyl)oxy]-1-(2-methylpropyl)-1H-pyrazol-3-yl}-N-methylmethanamine; Example 369

1-{5-[(5-chloro-2-fluorobenzyl)oxy]-1-(2-methylpropyl)-1H-pyrazol-3-yl}-N-methylmethanamine; Example 256

1-{1-(2,2-dimethylpropyl)-5-[(4-fluorobenzyl)oxy]-1H-pyrazol-3-yl}-N-methylmethanamine; Example 375

1-{5-[(2,5-difluorobenzyl)oxy]-1-(2,2-dimethylpropyl)-1H-pyrazol-3-yl}-N-methylmethanamine; Example 258

1-{5-[(5-chloro-2-fluorobenzyl)oxy]-1-(2,2-dimethylpropyl)-1H-pyrazol-3-yl}-N-methylmethanamine; Example 259

1-{5-[(2-fluorobenzyl)oxy]-1-(3-methylbutyl)-1H-pyrazol-3-yl}-N-methylmethanamine; Example 381

1-{5-[(4-fluorobenzyl)oxy]-1-(3-methylbutyl)-1H-pyrazol-3-yl}-N-methylmethanamine; Example 383

1-(5-[(4-fluorobenzyl)oxy]-1-{[1-(trifluoromethyl)cyclopentyl]methyl}-1H-pyrazol-3-yl)-N-methylmethanamine; Example 446

1-(5-[(2,5-difluorobenzyl)oxy]-1-{[1-(trifluoromethyl)cyclopentyl]methyl}-1H-pyrazol-3-yl)-N-methylmethanamine; Example 447

1-(5-[(5-chloro-2-fluorobenzyl)oxy]-1-{[1-(trifluoromethyl)cyclopentyl]methyl}-1H-pyrazol-3-yl)-N-methylmethanamine; Example 448

(−)-1-{5-[(5-chloro-2-fluorobenzyl)oxy]-1-(tetrahydro-2H-pyran-2-ylmethyl)-1H-pyrazol-3-yl}-N-methylmethanamine; Example 474

(+)-1-{5-[(5-chloro-2-fluorobenzyl)oxy]-1-(tetrahydro-2H-pyran-2-ylmethyl)-1H-pyrazol-3-yl}-N-methylmethanamine; Example 475

(−)-1-{1-(2-cyclopentylethyl)-5-[(2,5-difluorobenzyl)oxy]-1H-pyrazol-3-yl}-N-methylethanamine; Example 476

(+)-1-{1-(2-cyclopentylethyl)-5-[(2,5-difluorobenzyl)oxy]-1H-pyrazol-3-yl}-N-methylethanamine; Example 477

1-{5-[(2,5-difluorobenzyl)oxy]-1-(3-fluoro-3-methylbutyl)-1H-pyrazol-3-yl}-N-methylmethanamine; Example 481

1-{5-[(5-chloro-2-fluorobenzyl)oxy]-1-(3-fluoro-3-methylbutyl)-1H-pyrazol-3-yl}-N-methylmethanamine; Example 482

1-[1-benzyl-5-(benzyloxy)-1H-pyrazol-3-yl]-N-methylmethanamine; Example 1

1-{5-[(4-fluoro-2-methylbenzyl)oxy]-1-(tetrahydro-2H-pyran-2-ylmethyl)-1H-pyrazolo-3-yl}-N-methylmethanamine; Example 108

1-[5-(benzyloxy)-1-(bicyclo[2.2.1]hept-2-ylmethyl)-1H-pyrazol-3-yl]-N-methylmethanamine; Example 115

1-{1-(bicyclo[2.2.1]hept-2-ylmethyl)-5-[(2,5-difluorobenzyl)oxy]-1H-pyrazol-3-yl}-N-methylmethanamine; Example 117

1-{1-(bicyclo[2.2.1]hept-2-ylmethyl)-5-[(5-chloro-2-fluorobenzyl)oxy]-1H-pyrazol-3-yl}-N-methylmethanamine; Example 118

1-{5-[(3-chlorobenzyl)oxy]-1-(2-oxabicyclo[2.2.2]oct-3-yl-methyl)-1H-pyrazol-3-yl}-N-methylmethanamine; Example 508

1-{5-[(2,5-difluorobenzyl)oxy]-1-[(4,4-difluorocyclohexyl)methyl]-1H-pyrazol-3-yl}-N-methylmethanamine; Example 124

1-{5-[(2,5-difluorobenzyl)oxy]-1-[(1-fluorocyclohexyl)methyl]-1H-pyrazol-3-yl}-N-methylmethanamine; Example 127

2-[({1-(cyclopentylmethyl)-3-[(methylamino)methyl]-1H-pyrazol-5-yl}oxy)methyl]benzonitrile; Example 162

1-{1-(4-chlorobenzyl)-5-[(2,5-difluorobenzyl)oxy]-1H-pyrazol-3-yl}-N-methylmethanamine; Example 224

1-{1-butyl-5-[(2,5-difluorobenzyldifluorobenzyl)oxy]-1H-pyrazol-3-yl}-N-methylmethanamine; Example 242

1-{5-[(5-chloro-2-fluorobenzyl)oxy]-1-(2-ethylbutyl)-1H-pyrazol-3-yl}-N-methylmethanamine; Example 263

1-[5-(benzyloxy)-1-(1-cyclopentylethyl)-1H-pyrazol-3-yl]-N-methylmethanamine; Example 288

1-{5-[(5-chloro-2-fluorobenzyl)oxy]-1-(1-cyclopentylethyl)-1H-pyrazol-3-yl}-N-methylmethanamine; Example 291

1-[5-(benzyloxy)-1-(1-cyclohexylethyl)-1H-pyrazol-3-yl]-N-methylmethanamine; Example 292

1-{1-(1-cyclohexylethyl)-5-[(2-fluorobenzyl)oxy]-1H-pyrazol-3-yl}-N-methylmethanamine; Example 293

1-{1-(1-cyclohexylethyl)-5-[(4-fluorobenzyl)oxy]-1H-pyrazol-3-yl}-N-methylmethanamine; Example 295

1-{5-[(2-chlorobenzyl)oxy]-1-(1-cyclohexylethyl)-1H-pyrazol-3-yl}-N-methylmethanamine; Example 296

1-{1-(1-cyclohexylethyl)-5-[(2-methylbenzyl)oxy]-1H-pyrazol-3-yl}-N-methylmethanamine; Example 298

1-{1-(1-cyclohexylethyl)-5-[(3-methylbenzyl)oxy]-1H-pyrazol-3-yl}-N-methylmethanamine; Example 299

1-{1-(1-cyclohexylethyl)-5-[(2,4-difluorobenzyl)oxy]-1H-pyrazol-3-yl}-N-methylmethanamine; Example 300

1-{5-[(2-chloro-4-fluorobenzyl)oxy]-1-(1-cyclohexylethyl)-1H-pyrazol-3-yl}-N-methylmethanamine; Example 301

1-{1-(1-cyclohexylethyl)-5-[(4-fluoro-2-methylbenzyl)oxy]-1H-pyrazol-3-yl}-N-methylmethanamine; Example 302

1-{1-(1-cyclohexylethyl)-5-[(2,5-difluorobenzyl)oxy]-1H-pyrazol-3-yl}-N-methylmethanamine; Example 303

1-{5-[(5-chloro-2-fluorobenzyl)oxy]-1-(1-cyclohexylethyl)-1H-pyrazol-3-yl}-N-methylmethanamine; Example 304

1-{1-(1-cyclohexylethyl)-5-[(2-fluoro-5-methylbenzyl)oxy]-1H-pyrazol-3-yl}-N-methylmethanamine; Example 305

1-[5-(benzyloxy)-1-(1-cyclohexyl-2-fluoroethyl)-1H-pyrazol-3-yl]-N-methylmethanamine; Example 330

1-{5-(benzyloxy)-1-[(1-methylcyclohexyl)methyl]-1H-pyrazol-3-yl}-N-methylmethanamine; Example 331

1-{5-[(3-chlorobenzyl)oxy]-1-(3,4-dihydro-2H-chromen-2-ylmethyl)-1H-pyrazol-3-yl}-N-methylmethanamine; Example 341

N-({1-(cyclohexylmethyl)-5-[(2,5-difluorobenzyl)oxy]-1H-pyrazol-3-yl}methyl)cyclopropanamine; Example 342

N-({1-(cyclohexylmethyl)-5-[(2,5-difluorobenzyl)oxy]-1H-pyrazol-3-yl}methyl)ethanamine; Example 344

1-{1-(cyclohexylmethyl)-5-[(2,5-difluorobenzyl)oxy]-1H-pyrazol-3-yl}methanamine; Example 347

1-{1-(cyclohexylmethyl)-5-[difluoro(phenyl)methoxy]-1H-pyrazol-3-yl}-N-methylmethanamine; Example 349

1-[5-(benzyloxy)-1-(cyclohexylmethyl)-1H-pyrazol-3-yl]-N-methyl($^2H_2$)methanamine; Example 492

1-[5-(benzyloxy)-1-(cyclohexylmethyl)-1H-pyrazol-3-yl]-N-($^2H_3$)methyl($^2H_2$)methanamine; Example 493

1-[5-(benzyloxy)-1-(cyclohexylmethyl)-1H-pyrazol-3-yl]-N-($^2H_3$)methylmethanamine; Example 494

1-[1-(cyclopentylmethyl)-5-{[(2,5-difluorophenyl)($^2H_2$)methyl]oxy}-1H-pyrazol-3-yl]-N-methylmethanamine; Example 495

1-[5-{[(5-chloro-2-fluorophenyl)($^2H_2$)methyl]oxy}-1-(cyclopentylmethyl)-1H-pyrazol-3-yl]-N-methylmethanamine; Example 496

1-[1-(cyclohexylmethyl)-5-{[(2,5-difluorophenyl)($^2H_2$)methyl]oxy}-1H-pyrazol-3-yl]-N-methylmethanamine; Example 497

1-[5-{[(5-chloro-2-fluorophenyl)($^2H_2$)methyl]oxy}-1-(cyclohexylmethyl)-1H-pyrazol-3-yl]-N-methylmethanamine; Example 498 or 1-[5-{[(2,5-difluorophenyl)($^2H_2$)methyl]oxy}-1-(3,3-dimethylbutyl)-1H-pyrazol-3-yl]-N-methyl($^2H_2$)methanamine; Example 499.

[14] The medicament according to [1], wherein the compound of Formula (1) is any one of the following compounds or pharmaceutically acceptable salts thereof:

1-[5-(benzyloxy)-1-(cyclohexylmethyl)-1H-pyrazol-3-yl]-N-methylmethanamine; Example 5

1-{1-(cyclohexylmethyl)-5-[(2-fluorobenzyl)oxy]-1H-pyrazol-3-yl}-N-methylmethanamine; Example 20

1-{5-[(2-chloro-4-fluorobenzyl)oxy]-1-(cyclohexylmethyl)-1H-pyrazol-3-yl}-N-methylmethanamine; Example 30

1-{1-(cyclohexylmethyl)-5-[(4-fluoro-2-methylbenzyl)oxy]-1H-pyrazol-3-yl}-N-methylmethanamine; Example 31

1-{1-(cyclohexylmethyl)-5-[(2,5-difluorobenzyl)oxy]-1H-pyrazol-3-yl}-N-methylmethanamine; Example 33

1-{5-[(5-chloro-2-fluorobenzyl)oxy]-1-(cyclohexylmethyl)-1H-pyrazol-3-yl}-N-methylmethanamine; Example 34

1-{5-[(2-chloro-5-fluorobenzyl)oxy]-1-(cyclohexylmethyl)-1H-pyrazol-3-yl}-N-methylmethanamine; Example 37

1-{1-(cyclohexylmethyl)-5-[(2,5-dichlorobenzyl)oxy]-1H-pyrazol-3-yl}-N-methylmethanamine; Example 38

1-{1-(cyclopentylmethyl)-5-[(4-fluorobenzyl)oxy]-1H-pyrazol-3-yl}-N-methylmethanamine Example 137

1-{5-[(2-chlorobenzyl)oxy]-1-(cyclopentylmethyl)-1H-pyrazol-3-yl}-N-methylmethanamine; Example 138

1-{1-(cyclopentylmethyl)-5-[(2,4-difluorobenzyl)oxy]-1H-pyrazol-3-yl}-N-methylmethanamine; Example 144

1-{1-(cyclopentylmethyl)-5-[(2,5-difluorobenzyl)oxy]-1H-pyrazol-3-yl}-N-methylmethanamine; Example 147

1-{5-[(5-chloro-2-fluorobenzyl)oxy]-1-(cyclopentylmethyl)-1H-pyrazol-3-yl}-N-methylmethanamine; Example 148

1-{5-[(2,5-difluorobenzyl)oxy]-1-(3,3-dimethylbutyl)-1H-pyrazol-3-yl}-N-methylmethanamine; Example 266

1-{5-[(2,5-difluorobenzyl)oxy]-1-(3-methylbutyl)-1H-pyrazol-3-yl}-N-methylmethanamine; Example 269

1-{5-[(5-chloro-2-fluorobenzyl)oxy]-1-(3-methoxy-3-methylbutyl)-1H-pyrazol-3-yl}-N-methylmethanamine; Example 275

1-{1-(cyclopentylmethyl)-5-[(2,4,5-trifluorobenzyl)oxy]-1H-pyrazol-3-yl}-N-methylmethanamine; Example 280

1-{1-(2-cyclopentylethyl)-5-[(2,5-difluorobenzyl)oxy]-1H-pyrazol-3-yl}-N-methylethanamine; Example 315

N-methyl-1-{1-(3-methylbutyl)-5-[(2,4,5-trifluorobenzyl)oxy]-1H-pyrazol-3-yl}methanamine; Example 283

1-{1-(3,3-dimethylbutyl)-5-[(2,4,5-trifluorobenzyl)oxy]-1H-pyrazol-3-yl}-N-methylmethanamine; Example 284

1-{1-(4-fluorobenzyl)-5-[(2-fluorobenzyl)oxy]-1H-pyrazol-3-yl}-N-methylmethanamine; Example 218

1-{5-[(2,5-difluorobenzyl)oxy]-1-(4-fluorobenzyl)-1H-pyrazol-3-yl}-N-methylmethanamine; Example 219

1-{5-[(2,5-difluorobenzyl)oxy]-1-(4-methylbenzyl)-1H-pyrazol-3-yl}-N-methylmethanamine; Example 230

N-methyl-1-{1-(4-methylbenzyl)-5-[(2,4,5-trifluorobenzyl)oxy]-1H-pyrazol-3-yl}methanamine; Example 1-{5-[(5-chloro-2-fluorobenzyl)oxy]-1-(cyclopropylmethyl)-1H-pyrazol-3-yl}-N-methylmethanamine; Example 131

1-{5-[(5-chloro-2-fluorobenzyl)oxy]-1-(2-methylpropyl)-1H-pyrazol-3-yl}-N-methylmethanamine; Example 256

1-{5-[(2,5-difluorobenzyl)oxy]-1-(2,2-dimethylpropyl)-1H-pyrazol-3-yl}-N-methylmethanamine; Example 258

1-{5-[(5-chloro-2-fluorobenzyl)oxy]-1-(2,2-dimethylpropyl)-1H-pyrazol-3-yl}-N-methylmethanamine; Example 259

1-[l-benzyl-5-(benzyloxy)-1H-pyrazol-3-yl]-N-methylmethanamine; Example 1

1-{5-[(4-fluoro-2-methylbenzyl)oxy]-1-(tetrahydro-2H-pyran-2-ylmethyl)-1H-pyrazolo-3-yl]-N-methylmethanamine; Example 108

1-[5-(benzyloxy)-1-(bicyclo[2.2.1]hept-2-ylmethyl)-1H-pyrazol-3-yl]-N-methylmethanamine; Example 115

1-{1-(bicyclo[2.2.1]hept-2-ylmethyl)-5-[(2,5-difluorobenzyl)oxy]-1H-pyrazol-3-yl}-N-methylmethanamine; Example 117

1-{1-(bicyclo[2.2.1]hept-2-ylmethyl)-5-[(5-chloro-2-fluorobenzyl)oxy]-1H-pyrazol-3-yl}-N-methylmethanamine; Example 118

1-{5-[(3-chlorobenzyl)oxy]-1-(2-oxabicyclo[2.2.2]oct-3-ylmethyl)-1H-pyrazol-3-yl}-N-methylmethanamine; Example 508

1-{5-[(2,5-difluorobenzyl)oxy]-1-[(4,4-difluorocyclohexyl)methyl]-1H-pyrazol-3-yl}-N-methylmethanamine; Example 124

1-{5-[(2,5-difluorobenzyl)oxy]-1-[(1-fluorocyclohexyl)methyl]-1H-pyrazol-3-yl}-N-methylmethanamine; Example 127

2-[({1-(cyclopentylmethyl)-3-[(methylamino)methyl]-1H-pyrazol-5-yl}oxy)methyl]benzonitrile; Example 162

1-{1-(4-chlorobenzyl)-5-[(2,5-difluorobenzyl)oxy]-1H-pyrazol-3-yl}-N-methylmethanamine; Example 224

1-{5-[(5-chloro-2-fluorobenzyl)oxy]-1-(2-ethylbutyl)-1H-pyrazol-3-yl}-N-methylmethanamine; Example 263

1-[5-(benzyloxy)-1-(1-cyclopentylethyl)-1H-pyrazol-3-yl]-N-methylmethanamine; Example 288

1-{5-[(5-chloro-2-fluorobenzyl)oxy]-1-(1-cyclopentylethyl)-1H-pyrazol-3-yl}-N-methylmethanamine; Example 291

1-[5-(benzyloxy)-1-(1-cyclohexylethyl)-1H-pyrazol-3-yl]-N-methylmethanamine; Example 292

1-{1-(1-cyclohexylethyl)-5-[(2-fluorobenzyl)oxy]-1H-pyrazol-3-yl}-N-methylmethanamine; Example 293

1-{l-(1-cyclohexylethyl)-5-[(4-fluorobenzyl)oxy]-1H-pyrazol-3-yl}-N-methylmethanamine; Example 295

1-{5-[(2-chlorobenzyl)oxy]-1-(1-cyclohexylethyl)-1H-pyrazol-3-yl}-N-methylmethanamine; Example 296

1-{1-(1-cyclohexylethyl)-5-[(2-methylbenzyl)oxy]-1H-pyrazol-3-yl}-N-methylmethanamine; Example 298

1-{1-(1-cyclohexylethyl)-5-[(3-methylbenzyl)oxy]-1H-pyrazol-3-yl}-N-methylmethanamine; Example 299

1-{1-(1-cyclohexylethyl)-5-[(2,4-difluorobenzyl)oxy]-1H-pyrazol-3-yl}-N-methylmethanamine; Example 300

1-{5-[(2-chloro-4-fluorobenzyl)oxy]-1-(1-cyclohexylethyl)-1H-pyrazol-3-yl}-N-methylmethanamine; Example 301

1-{1-(1-cyclohexylethyl)-5-[(4-fluoro-2-methylbenzyl)oxy]-1H-pyrazol-3-yl}-N-methylmethanamine; Example 302

1-{1-(1-cyclohexylethyl)-5-[(2,5-difluorobenzyl)oxy]-1H-pyrazol-3-yl}-N-methylmethanamine; Example 303

1-{5-[(5-chloro-2-fluorobenzyl)oxy]-1-(1-cyclohexylethyl)-1H-pyrazol-3-yl}-N-methylmethanamine; Example 304

1-{1-(1-cyclohexylethyl)-5-[(2-fluoro-5-methylbenzyl)oxy]-1H-pyrazol-3-yl}-N-methylmethanamine; Example 305

1-[5-(benzyloxy)-1-(1-cyclohexyl-2-fluoroethyl)-1H-pyrazol-3-yl]-N-methylmethanamine; Example 330

1-{5-(benzyloxy)-1-[(1-methylcyclohexyl)methyl]-1H-pyrazol-3-yl}-N-methylmethanamine; Example 331

1-{5-[(3-chlorobenzyl)oxy]-1-(3,4-dihydro-2H-chromen-2-ylmethyl)-1H-pyrazol-3-yl}-N-methylmethanamine; Example 341

N-({1-(cyclohexylmethyl)-5-[(2,5-difluorobenzyl)oxy]-1H-pyrazol-3-yl}methyl)cyclopropanamine; Example 342

N-({1-(cyclohexylmethyl)-5-[(2,5-difluorobenzyl)oxy]-1H-pyrazol-3-yl}methyl)ethanamine; Example 344

1-{1-(cyclohexylmethyl)-5-[(2,5-difluorobenzyl)oxy]-1H-pyrazol-3-yl}methanamine; Example 347

1-{1-(cyclohexylmethyl)-5-[difluoro(phenyl)methoxy]-1H-pyrazol-3-yl}-N-methylmethanamine; Example 349

1-[5-(benzyloxy)-1-(cyclohexylmethyl)-1H-pyrazol-3-yl]-N-methyl($^2H_2$)methanamine; Example 492

1-[5-(benzyloxy)-1-(cyclohexylmethyl)-1H-pyrazol-3-yl]-N-($^2H_3$)methyl($^2H_2$)methanamine; Example 493

1-[5-(benzyloxy)-1-(cyclohexylmethyl)-1H-pyrazol-3-yl]-N-($^2H_3$)methylmethanamine; Example 494

1-[1-(cyclopentylmethyl)-5-{[(2,5-difluorophenyl) ($^2H_2$)methyl]oxy}-1H-pyrazol-3-yl]-N-methylmethanamine; Example 495

1-[5-{[(5-chloro-2-fluorophenyl) ($^2H_2$)methyl]oxy}-1-(cyclopentylmethyl)-1H-pyrazol-3-yl]-N-methylmethanamine; Example 496

1-[1-(cyclohexylmethyl)-5-{[(2,5-difluorophenyl) ($^2H_2$)methyl]oxy}-1H-pyrazol-3-yl]-N-methylmethanamine; Example 497

1-[5-{[(5-chloro-2-fluorophenyl) ($^2H_2$)methyl]oxy}-1-(cyclohexylmethyl)-1H-pyrazol-3-yl]-N-methylmethanamine; Example 498 or 1-[5-{[(2,5-difluorophenyl) ($^2H_2$)methyl]oxy}-1-(3,3-dimethylbutyl)-1H-pyrazol-3-yl]-N-methyl($^2H_2$)methanamine; Example 499.

[15] The medicament according to any one of [1] to [14], wherein the non-motor symptoms associated with Parkinson's disease are selected from the group consisting of psychopathic symptoms, depressive symptoms, anxiety symptoms, sleep disorder, cognitive dysfunction, and any combinations thereof.

[16] The medicament according to any one of [1] to [14], wherein the non-motor symptoms associated with Parkinson's disease are psychopathic symptoms, depressive symptoms, anxiety symptoms, or cognitive dysfunction.

[17] The medicament according to any one of [1] to [14], wherein the non-motor symptoms associated with Parkinson's disease are psychopathic symptoms, depressive symptoms, anxiety symptoms, or sleep disorder.

[18] The medicament according to any one of [1] to [14], wherein the non-motor symptoms associated with Parkinson's disease are psychopathic symptoms, depressive symptoms, or anxiety symptoms.

[19] The medicament according to any one of [1] to [14], wherein the non-motor symptoms associated with Parkinson's disease are psychopathic symptoms, sleep disorder, or cognitive dysfunction.

[20] The medicament according to any one of [1] to [14], wherein the non-motor symptoms associated with Parkinson's disease are psychopathic symptoms or depressive symptoms.
[21] The medicament according to any one of [1] to [14], wherein the non-motor symptoms associated with Parkinson's disease are psychopathic symptoms or sleep disorder.
[22] The medicament according to any one of [1] to [14], wherein the non-motor symptoms associated with Parkinson's disease are psychopathic symptoms.
[23] A method for treating non-motor symptoms associated with Parkinson's disease or preventing a relapse thereof, comprising administering a therapeutically effective amount of a compound of Formula (1) according to any one of [1] to [14] or a pharmaceutically acceptable salt thereof to a patient in need thereof.
[24] Use of a compound of Formula (1) according to any one of [1] to [14] or a pharmaceutically acceptable salt thereof in the manufacture of a medicament for treating non-motor symptoms associated with Parkinson's disease or preventing a relapse thereof according to any one of [1] to [14].
[25] An agent for antagonizing serotonin 5-$HT_{2A}$ receptor, inhibiting serotonin transporter, and antagonizing serotonin 5-$HT_{2C}$ receptor, comprising a compound of Formula (1) according to any one of [1] to [14] or a pharmaceutically acceptable salt thereof.
[26] A medicament for treating non-motor symptoms associated with Parkinson's disease or preventing a relapse thereof, comprising a compound of Formula (1) according to any one of [1] to [14] or a pharmaceutically acceptable salt thereof, wherein the medicament has the action of antagonizing serotonin 5-$HT_{2A}$ receptor, inhibiting serotonin transporter, and antagonizing serotonin 5-$HT_{2C}$ receptor.
[27] A medicament for treating non-motor symptoms associated with Parkinson's disease or preventing a relapse thereof, comprising as an active ingredient a compound that has the action of antagonizing serotonin 5-$HT_{2A}$ receptor, inhibiting serotonin transporter, and antagonizing serotonin 5-$HT_{2C}$ receptor.
[28] A medicament for treating psychopathic symptoms, depressive symptoms, anxiety disorder, agitation symptoms, or sleep disorder, associated with various diseases presenting with cognitive dysfunction such as Alzheimer disease, Lewy body disease, frontotemporal degeneration, vascular disease, and traumatic brain injury, or preventing a relapse thereof, comprising a compound of Formula (1) according to any one of [1] to [14] or a pharmaceutically acceptable salt thereof.
[29] A medicament for treating psychopathic symptoms, depressive symptoms, or agitation symptoms, associated with Alzheimer disease, or preventing a relapse thereof, comprising a compound of Formula (1) according to any one of [1] to [14] or a pharmaceutically acceptable salt thereof.
[30] A medicament for treating a disease mediated by serotonergic system or dopaminergic system such as fibromyalgia and attention-deficit hyperactivity disorder or preventing a relapse thereof, comprising a compound of Formula (1) according to any one of [1] to [14] or a pharmaceutically acceptable salt thereof.
[31] A compound drug for treating a disease mediated by serotonergic system or dopaminergic system, particularly non-motor symptoms associated with Parkinson's disease, or preventing a relapse thereof, comprising as an active ingredient a compound of Formula (1) according to any one of [1] to [14] or a pharmaceutically acceptable salt thereof and at least one medicament selected from the group consisting of antidepressants, anxiolytic drugs, antipsychotic drugs, dopamine replacement drugs, dopamine receptor agonists, antiparkinsonian drugs, antiepilepsy drugs, anticonvulsant drugs, analgesic drugs, hormone preparations, antimigraine drugs, adrenaline § receptor antagonists, antidementia drugs, therapeutic drugs for mood disorder, antiemetic drugs, sleep-inducing drugs, and anticonvulsant drugs.
[32] A medicament for treating a disease mediated by serotonergic system or dopaminergic system, particularly non-motor symptoms associated with Parkinson's disease, or preventing a relapse thereof, comprising a compound of Formula (1) according to any one of [1] to [14] or a pharmaceutically acceptable salt thereof, for use in combination with at least one medicament selected from the group consisting of antidepressants, anxiolytic drugs, antipsychotic drugs, dopamine replacement drugs, dopamine receptor agonists, antiparkinsonian drugs, antiepilepsy drugs, anticonvulsant drugs, analgesic drugs, hormone preparations, antimigraine drugs, adrenaline @ receptor antagonists, antidementia drugs, therapeutic drugs for mood disorder, antiemetic drugs, sleep-inducing drugs, and anticonvulsant drugs.

Effect of the Invention

The present compound has serotonin 5-$HT_{2A}$ receptor antagonism or inverse agonist action, serotonin 5-$HT_{2C}$ receptor antagonism or inverse agonist action, and SERT inhibitory action and may be effective for treating psychopathic symptoms and other non-motor symptoms in diseases mediated by serotonergic system or dopaminergic system, particularly Parkinson's disease, and/or preventing a relapse thereof. Administration of the present compound may be more effective than a single administration of a medicament that has one of these actions only.

BRIEF DESCRIPTION OF DRAWINGS

FIG. 1 The results of rat-forced swimming test in Test 3 are shown. The vertical axis is the average time of immobility±standard deviation;  means $p<0.01$ to the vehicle group; * means $p<0.001$ to the vehicle group (two-sided parametric Dunnett's multiple comparison test).

FIG. 2 The results of rat-forced swimming test in Test 3 are shown. The vertical axis is the average time of immobility±standard deviation; * means $p<0.05$ to the vehicle group; *** means $p<0.001$ to the vehicle group (two-sided parametric Dunnett's multiple comparison test).

FIG. 3 The results of rat social interaction evaluation in Test 4 are shown. The vertical axis is the average time of social interaction±standard deviation; * means $p<0.05$ to the vehicle group; ** means $p<0.01$ to the vehicle group (two-sided parametric Dunnett's multiple comparison test).

FIG. 4 The results of rat social interaction evaluation in Test 4 are shown. The vertical axis is the average time of social interaction±standard deviation; * means $p<0.05$ to the vehicle group (two-sided parametric Dunnett's multiple comparison test).

FIG. 5 The results of rat social interaction evaluation in Test 4 are shown. The vertical axis is the average time of social interaction±standard deviation; * means $p<0.05$ to the vehicle group (two-sided parametric Dunnett's multiple comparison test).

FIG. 6 The results of rat social interaction evaluation in Test 4 are shown. The vertical axis is the average time of social interaction±standard deviation (two-sided parametric Dunnett's multiple comparison test).

DESCRIPTION OF EMBODIMENTS

The present invention is illustrated below in more detail. The number of substituents on a group defined with the phrase "optionally-substituted" used herein is not limited as long as it is acceptable, and the number may be 1 or more. The definition of each group is also applied to the case where the group is a part of another group or a substituent thereof unless otherwise specified.

Throughout the description, for example, $C_{1-6}$, $C_{1-4}$, and $C_6$ indicate that the number of carbon atoms is 1 to 6, 1 to 4, and 6, respectively. As used herein, a similar definition of carbon having a different subscript number is also meant in the same manner.

The "halogen atom" used herein includes fluorine atom, chlorine atom, bromine atom, and iodine atom. The halogen atom includes preferably fluorine atom and chlorine atom.

The "$C_{1-6}$ alkyl group" used herein means a straight- or branched-chain saturated aliphatic hydrocarbon group having 1 to 6 carbon atoms, and specifically includes methyl group, ethyl group, propyl group, n-butyl group, n-pentyl group, n-hexyl group, isopropyl group, sec-butyl group, isobutyl group, tert-butyl group, 1-methylbutyl group, 2-methylbutyl group, 3-methylbutyl group, 1-ethylpropyl group, and the like. The $C_{1-6}$ alkyl group includes preferably a $C_{1-4}$ alkyl group, more preferably a $C_{1-3}$ alkyl group.

The "$C_{1-6}$ alkyl group optionally substituted with 1 to 3 deuterium atoms" used herein means a $C_{1-6}$ alkyl group where any 1 to 3 hydrogen atoms of the above-defined $C_{1-6}$ alkyl group may be optionally replaced with deuterium atom (also referred to as "$^2$H" or "D" hereinafter). The $C_{1-6}$ alkyl group substituted with 1 to 3 deuterium atoms includes preferably ($^2$H$_3$)methyl group.

The "$C_{4-7}$ alkyl group" used herein means a straight- or branched-chain saturated aliphatic hydrocarbon group having 4 to 7 carbon atoms, and specifically includes n-butyl group, n-pentyl group, n-hexyl group, n-heptyl group, 1-ethylpropyl group, 1,1-dimethylpropyl group, 1-methyl-1-ethylpropyl group, 1,1-diethylpropyl group, 2,2-dimethylpropyl group, sec-butyl group, isobutyl group, tert-butyl group, 1-methylbutyl group, 2-methylbutyl group, 3-methylbutyl group, 2-ethylbutyl group, 2,2-dimethylbutyl group, 3,3-dimethylbutyl group, 2-methyl-2-ethylbutyl group, and the like. The $C_{4-7}$ alkyl group includes preferably a $C_{4-6}$ alkyl group, and specifically includes isobutyl group, 2,2-dimethylpropyl group, 3-methylbutyl group, 3,3-dimethylbutyl group, and 2-ethylbutyl group.

The "$C_{6-10}$ aryl group" used herein means a monocyclic or bicyclic aromatic hydrocarbon ring group having 6 to 10 carbon atoms, and includes preferably a $C_6$ or $C_{10}$ aryl group. The $C_{6-10}$ aryl group specifically includes phenyl group, 1- and 2-naphthyl group, and the like.

The "5- to 10-membered heteroaryl group" means a 5- to 10-membered monocyclic or bicyclic aromatic heterocyclic group comprising 1 to 3 heteroatoms independently selected from the group consisting of nitrogen atom, oxygen atom, and sulfur atom, wherein the position of heteroatom in the heteroaryl group and the bonding position of the heteroaryl group are not limited as long as they are chemically stable. The 5- to 10-membered heteroaryl group specifically includes furyl group, thienyl group, pyrrolyl group, oxazolyl group, isoxazolyl group, thiazolyl group, isothiazolyl group, imidazolyl group, pyrazolyl group, furazanyl group, oxadiazolyl group, triazolyl group, tetrazolyl group, pyridyl group, pyrimidinyl group, pyridazinyl group, pyrazinyl group, indolyl group, quinolyl group, isoquinolyl group, quinazolinyl group, imidazo[2,1-b] [1,3]thiazolyl group, benzofuryl group, indolizinyl group, indazolyl group, and the like; preferably 5- and 6-membered monocyclic heteroaryl group and 9- and 10-membered bicyclic heteroaryl group. The 5- to 10-membered heteroaryl group also includes an N-oxide form thereof wherein the nitrogen atom of the heteroaryl group is oxidized.

Furthermore, the $C_{6-10}$ aryl group and the 5- to 10-membered heteroaryl group may each form a fused ring with a $C_{3-8}$ cycloalkyl, $C_{4-8}$ cycloalkenyl, or 5- to 10-membered saturated heterocyclic group. In this case, the $C_{6-10}$ aryl group forming a fused ring specifically includes the following formulae:

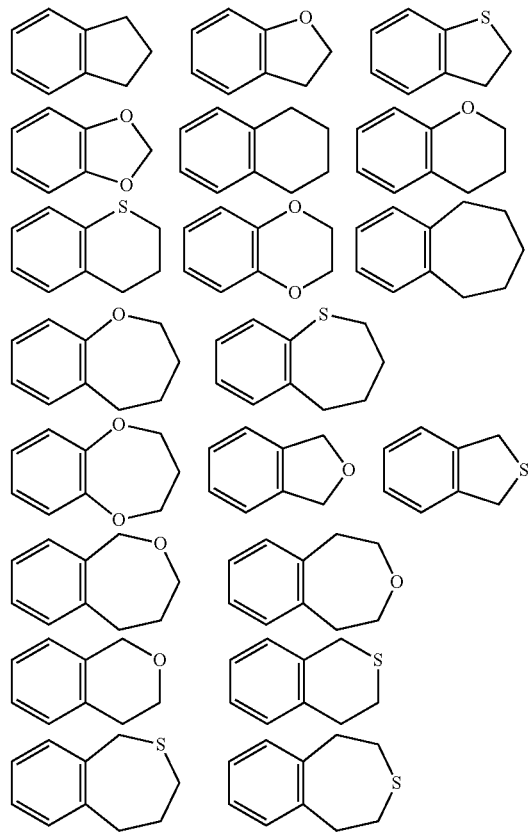

wherein the bonding position of the benzene ring is not limited as long as it is chemically stable. Furthermore, the 5- to 10-membered heteroaryl group forming a fused ring specifically includes the following formulae:

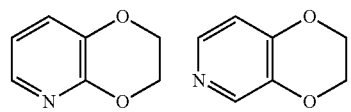

wherein the bonding position of the pyridine ring is not limited as long as it is chemically stable. The fused ring may have the below-mentioned substituent which is illustrated as a substituent for each of rings forming the fused ring.

The "$C_{3-8}$ cycloalkyl group" used herein means a monocyclic or bicyclic saturated aliphatic hydrocarbon ring group having 3 to 8 carbon atoms; and specifically includes cyclopropyl group, cyclobutyl group, cyclopentyl group, cyclohexyl group, cycloheptyl group, cyclooctyl group, bicyclo[2,2,1]heptyl group (norbornyl group), bicyclo[3,2,0]heptyl group, and the like. The $C_{3-8}$ cycloalkyl group includes preferably a monocyclic $C_{3-6}$ cycloalkyl group.

The "$C_{4-8}$ cycloalkenyl group" used herein means a monocyclic or bicyclic unsaturated aliphatic hydrocarbon ring group having 4 to 8 carbon atoms with 1 or 2 double bonds, and specifically includes cyclobutenyl group, cyclopentenyl group, cyclohexenyl group, and cycloheptenyl group. The position of double bond in the ring is not limited. The $C_{4-8}$ cycloalkenyl group includes preferably $C_5$ and $C_6$ cycloalkenyl groups.

The "5- to 10-membered saturated heterocyclic group" used herein means a 5- to 10-membered monocyclic or bicyclic saturated aliphatic heterocyclic group comprising 1 to 3 heteroatoms independently selected from the group consisting of oxygen atom and sulfur atom as a constituent atom of the ring, wherein the position of heteroatom in the heterocyclic group and the bonding position of the heterocyclic group are not limited as long as they are chemically stable. The saturated heterocyclic group includes preferably 5- to 8-membered saturated heterocyclic groups, more preferably 5- and 6-membered saturated heterocyclic groups. The 5- to 10-membered saturated heterocyclic group specifically includes tetrahydrofuryl group, tetrahydro-2H-pyranyl group, 1,4-dioxanyl group, tetrahydrothienyl group, tetrahydro-2H-thiopyranyl group, and bicyclic groups of the following formulae:

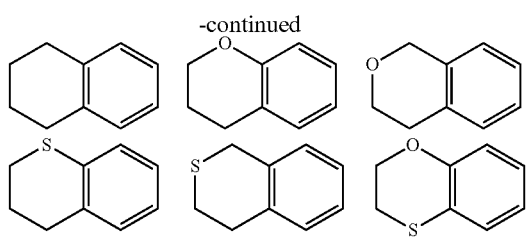

wherein the bonding position of the ring is not limited as long as it is chemically stable. The 5- to 10-membered saturated heterocyclic group is preferably a 5- to 10-membered saturated heterocyclic group comprising 1 or 2 oxygen atoms in the ring, and includes, for example, tetrahydrofuryl group, tetrahydro-2H-pyranyl group, 1,4-dioxanyl group, 7-oxabicyclo[2,2,1]heptyl group, and 2-oxabicyclo[2,2,2]octyl group.

The $C_{3-8}$ cycloalkyl group, $C_{4-8}$ cycloalkenyl group, and 5- to 10-membered saturated heterocyclic group may each form a fused ring with a $C_{6-10}$ aryl or 5- to 10-membered heteroaryl. The fused ring specifically includes the following formulae:

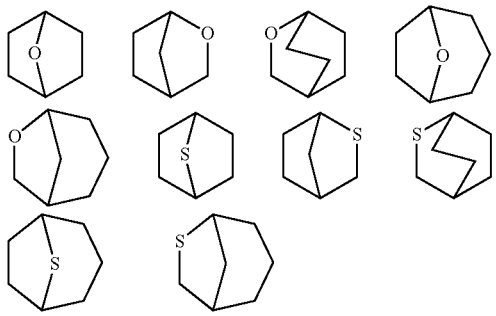

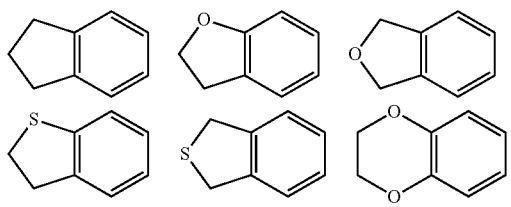

wherein the bonding position of the $C_{3-8}$ cycloalkyl group, $C_{4-8}$ cycloalkenyl group, and 5- to 10-membered saturated heterocyclic group is not limited as long as it is chemically stable. The fused ring may have the below-mentioned substituent which is illustrated as a substituent for each of rings forming the fused ring.

The substituents of the "optionally-substituted $C_{6-10}$ aryl group" and "optionally-substituted 5- to 10-membered heteroaryl group" include, for example, a halogen atom; a $C_{1-6}$ alkyl group optionally substituted with fluorine atom; a $C_{1-6}$ alkyloxy group optionally substituted with fluorine atom; hydroxy group; a $C_{1-6}$ alkylthio group; a $C_{6-10}$ aryloxy group; a $C_{6-10}$ arylthio group; cyano group; —$CO_2R^{11}$; —$SO_2R^{11}$; —$NR^{10}SO_2R^{11}$; —$OSO_2R^{11}$; —$COR^{12}$; —$SO_2NR^{12}R^{13}$; —$CONR^{12}R^{13}$; —$NR^{12}R^{13}$; —$NR^{10}CONR^{12}R^{13}$; —$NR^{10}COR^{12}$; —$CR^{12}=N(OR^{11})$; oxime group; a $C_{3-8}$ cycloalkyl group; a $C_{6-10}$ aryl group; and a 5- to 10-membered heteroaryl group (wherein $R^{10}$ is the same as defined in the above [1], $R^{11}$ is a $C_{1-6}$ alkyl group, a $C_{3-8}$ cycloalkyl group, a $C_{6-10}$ aryl group, or a 5- to 10-membered heteroaryl group, and $R^{12}$ and $R^{13}$ are each independently hydrogen atom, a $C_{1-6}$ alkyl group, a $C_{3-8}$ cycloalkyl group, a $C_{6-10}$ aryl group, or a 5- to 10-membered heteroaryl group; and the $C_{6-10}$ aryl group and 5- to 10-membered heteroaryl group in $R^{11}$, $R^{12}$, and $R^{13}$ may be each optionally further substituted with a halogen atom, a $C_{1-6}$ alkyl group, hydroxy group, or a $C_{1-6}$ alkyloxy group). The substituents include preferably a halogen atom, a $C_{1-6}$ alkyl group optionally substituted with fluorine atom, a $C_{1-6}$ alkyloxy group optionally substituted with fluorine atom, hydroxy group, a $C_{1-6}$ alkylthio group, and cyano group; and more preferably fluorine atom, chlorine atom, bromine atom, methyl group, ethyl group, isopropyl group, trifluoromethyl group, methoxy group, ethoxy group, isopropoxy group, trifluoromethoxy group, difluoromethoxy group, and cyano group. As used herein, one or more of the same or different substituents may exist at any position as long as the substitution is possible.

The substituents of the "optionally-substituted $C_{1-6}$ alkyl group" and "optionally-substituted $C_{4-7}$ alkyl group" include, for example, fluorine atom; hydroxy group; and a $C_{1-6}$ alkyloxy group optionally substituted with fluorine atom. As used herein, one or more of the same or different substituents may exist at any position as long as the substitution is possible.

The substituents of the "optionally-substituted $C_{3-8}$ cycloalkyl group", "optionally-substituted $C_{4-8}$ cycloalkenyl group", and "optionally-substituted 5- to 10-membered saturated heterocyclic group" include, for example, fluorine atom; a $C_{1-6}$ alkyl group optionally substituted with fluorine atom; hydroxy group; and a $C_{1-6}$ alkyloxy group optionally substituted with fluorine atom. As used herein, one or more of the same or different substituents may exist at any position as long as the substitution is possible.

The "$C_{1-6}$ alkyloxy group" used herein means an oxy group substituted with the above-defined "$C_{1-6}$ alkyl group", and specifically includes methoxy group, ethoxy group, propoxy group, isopropoxy group, 1-methylethoxy group, n-butoxy group, sec-butoxy group, tert-butoxy group, 1-methylpropoxy group, 2-methylpropoxy group, 1,1-dimethylethoxy group, pentyloxy group, and hexyloxy group. The $C_{1-6}$ alkyloxy group includes preferably a $C_{1-4}$ alkyloxy group, and includes, for example, methoxy group, ethoxy group, and isopropoxy group.

The "$C_{1-6}$ alkylthio group" used herein means thio group substituted with the above-defined "$C_{1-6}$ alkyl group" and includes, for example, methylthio group, ethylthio group, propylthio group, 1-methylethylthio group, butylthio group, 1-methylpropylthio group, 2-methylpropylthio group, 1,1-dimethylethylthio group, pentylthio group, and hexylthio group. The $C_{1-6}$ alkylthio group includes preferably a $C_{1-4}$ alkylthio group.

The "$C_{6-10}$ aryloxy group" used herein means oxy group substituted with the above-defined "$C_{6-10}$ aryl group". The $C_{6-10}$ aryloxy group includes preferably a $C_6$ aryloxy group and $C_{10}$ aryloxy group, and includes, for example, phenyloxy group, 1-naphthyloxy group, and 2-naphthyloxy group.

The "$C_{6-10}$ arylthio group" used herein means thio group substituted with the above-defined "$C_{6-10}$ aryl group". The $C_{6-10}$ arylthio group includes preferably a $C_6$ arylthio group or $C_{10}$ arylthio group, and includes, for example, phenylthio group, 1-naphthylthio group, and 2-naphthylthio group.

The "—$CONR^{12}R^{13}$" used herein includes, for example, carbamoyl group, methylcarbamoyl group, ethylcarbamoyl group, propylcarbamoyl group, isopropylcarbamoyl group, dimethylcarbamoyl group, diethylcarbamoyl group, and methylethylcarbamoyl group.

The "—$CO_2R^{11}$" used herein includes, for example, methoxycarbonyl group, ethoxycarbonyl group, propoxycarbonyl group, butoxycarbonyl group, and tert-butoxycarbonyl group.

The "—$COR^{12}$" used herein includes, for example, acetyl group, propionyl group, butyryl group, isobutyryl group, valeryl group, isovaleryl group, pivaloyl group, pentanoyl group, isopentanoyl group, neopentanoyl group, and hexanoyl group.

The "—$SO_2R^{11}$" used herein includes, for example, methylsulfonyl group, ethylsulfonyl group, propylsulfonyl group, butylsulfonyl group, and tert-butylsulfonyl group.

The "—$NR^{10}SO_2R^{11}$" used herein includes, for example, methylsulfonylamide group, ethylsulfonylamide group, propylsulfonylamide group, butylsulfonylamide group, and tert-butylsulfonylamide group.

The "—$NR^{10}CONR^{12}R^{13}$" used herein includes, for example, methylureido group, ethylureido group, and propylureido group.

The "—$NR^{12}R^{13}$" used herein includes, for example, amino group, methylamino group, ethylamino group, propylamino group, dimethylamino group, diethylamino group, and methylethylamino group.

The "—$NR^{10}COR^{12}$" used herein includes, for example, acetylamino group, ethylcarbonylamino group, propyl-carbonylamino group, isopropylcarbonylamino group, butyl-carbonylamino group, isobutylcarbonylamino group, benzoylamino group, and 1- and 2-naphthoylamino group.

The "—$OSO_2R^{11}$" used herein includes, for example, methylsulfonyloxy group, ethylsulfonyloxy group, propylsulfonyloxy group, butylsulfonyloxy group, and tert-butylsulfonyloxy group.

The "—$SO_2NR^{12}R^{13}$" used herein includes, for example, methylaminosulfonyl group, ethylaminosulfonyl group, propylaminosulfonyl group, butylaminosulfonyl group, and tert-butylaminosulfonyl group.

The "—$CR^{12}=N(OR^{11})$" used herein includes, for example, N-hydroxyiminoethyl group, N-hydroxy-1-iminopropyl group, N-methoxyiminoethyl group, N-methoxy-1-iminopropyl group, N-ethoxyiminoethyl group, and N-ethoxy-1-iminopropyl group.

Specific embodiments of each substituent in a compound of Formula (1) are illustrated as follows. The present invention also encompasses any combinations of the embodiments of each substituent in Formula (1).

$R^1$ and $R^2$ are each independently hydrogen atom, a $C_{1-6}$ alkyl group optionally substituted with deuterium atoms, or a $C_{3-8}$ cycloalkyl group; preferably hydrogen atom, a $C_{1-6}$ alkyl group optionally substituted with 1 to 3 deuterium atoms (e.g., a $C_{1-3}$ alkyl group), or a $C_{3-6}$ cycloalkyl group. More preferably, one of $R^1$ and $R^2$ is hydrogen atom, and the other is a $C_{1-6}$ alkyl group (e.g., a $C_{1-3}$ alkyl group).

$R^1$ and $R^2$ specifically include hydrogen atom, methyl group, ($^2H_3$)methyl group, ethyl group, propyl group, isopropyl group, and cyclopropyl group; preferably one of $R^1$ and $R^2$ is hydrogen atom, and the other is methyl group.

$R^3$ and $R^4$ are each independently hydrogen atom, deuterium atom, or a $C_{1-6}$ alkyl group, preferably hydrogen atom, deuterium atom, or a $C_{1-3}$ alkyl group.

$R^3$ and $R^4$ specifically include hydrogen atom, deuterium atom, methyl group, and ethyl group; preferably both of $R^3$ and $R^4$ are hydrogen atom. $R^3$ and $R^4$ may be each independently hydrogen atom or methyl group.

$R^5$ is an optionally-substituted $C_{4-7}$ alkyl group or —$(CR^8R^9)_r$-E.

The $C_{4-7}$ alkyl group of $R^5$ specifically includes n-butyl group, n-pentyl group, n-hexyl group, n-heptyl group, 1-ethylpropyl group, 1,1-dimethylpropyl group, 1-methyl-1-ethylpropyl group, 1,1-diethylpropyl group, 2,2-dimethylpropyl group, sec-butyl group, isobutyl group, tert-butyl group, 1-methylbutyl group, 2-methylbutyl group, 3-methylbutyl group, 2-ethylbutyl group, 2,2-dimethylbutyl group, 3,3-dimethylbutyl group, 2-methyl-2-ethylbutyl group, and the like; preferably isobutyl group, 2,2-dimethylpropyl group, 3-methylbutyl group, 3,3-dimethylbutyl group, and 2-ethylbutyl group.

$R^8$ and $R^9$ are each independently hydrogen atom, fluorine atom, or an optionally-substituted $C_{1-6}$ alkyl group; preferably hydrogen atom or a $C_{1-6}$ alkyl group optionally substituted with the same or different 1 to 3 halogen atoms; more preferably hydrogen atom or a $C_{1-3}$ alkyl group. Even more preferably, both of $R^8$ and $R^9$ are hydrogen atom. $R^8$ and $R^9$ specifically include hydrogen atom, methyl group, ethyl group, and hydroxymethyl group.

r is 1, 2, 3, or 4; preferably 1, 2, or 3; more preferably 1 or 2; even more preferably 1.

E is an optionally-substituted $C_{3-8}$ cycloalkyl group, an optionally-substituted $C_{4-8}$ cycloalkenyl group, an optionally-substituted 5- to 10-membered saturated heterocyclic group which comprises 1 to 3 heteroatoms independently selected from the group consisting of oxygen atom and sulfur atom as a constituent atom of the ring, an optionally-substituted $C_{6-10}$ aryl group, or an optionally-substituted 5- to 10-membered heteroaryl group; preferably an optionally-substituted $C_{3-8}$ cycloalkyl group, an optionally-substituted 5- to 10-membered saturated heterocyclic group which comprises 1 to 3 heteroatoms independently selected from the group consisting of oxygen atom and sulfur atom as a constituent atom of the ring, an optionally-substituted $C_{6-10}$ aryl group, or an optionally-substituted 5- to 10-membered heteroaryl group; more preferably an optionally-substituted $C_{3-8}$ cycloalkyl group, an optionally-substituted 5- to 10-membered saturated heterocyclic group which comprises 1 to 3 heteroatoms independently selected from the group consisting of oxygen atom and sulfur atom as a constituent atom of the ring, or an optionally-substituted $C_{6-10}$ aryl group; even more preferably an optionally-substituted $C_{3-8}$ cycloalkyl group or an optionally-substituted $C_{6-10}$ aryl group; still even more preferably an optionally-substituted $C_{3-8}$ cycloalkyl group.

The substituents of the optionally-substituted $C_{6-10}$ aryl group and optionally-substituted 5- to 10-membered heteroaryl group in E include, for example, (i) halogen atoms such as fluorine atom and chlorine atom, (ii) $C_{1-6}$ alkyl groups such as methyl group, ethyl group, and propyl group, (iii) $C_{1-6}$ alkyloxy groups such as methoxy group, ethoxy group, and isopropoxy group, (iv) $C_{1-6}$ alkylthio groups such as methylthio group and ethylthio group, (v) cyano group, (vi) trifluoromethyl group, (vii) trifluoromethoxy group, (viii) hydroxy group, and (ix) difluoromethoxy group; preferably halogen atoms (preferably fluorine atom and chlorine atom), methyl group, and methoxy group. As used herein, one or more of the same or different substituents may exist at any position as long as the substitution is possible.

E specifically includes phenyl group optionally substituted with a substituent selected from the group consisting of a halogen atom, cyano group, a $C_{1-6}$ alkyl group and a $C_{1-6}$ alkyloxy group (e.g., phenyl group substituted at the 2-, 3-, or 4-position, preferably at the 4-position); 1-naphthyl group; 2-naphthyl group; cyclopropyl group; cyclobutyl group; cyclopentyl group; cyclohexyl group; cycloheptyl group; tetrahydrofuryl group; tetrahydro-2H-pyranyl group; 1,4-dioxanyl group; tetrahydrothienyl group; tetrahydro-2H-thiopyranyl group; and bicyclic ring groups of the following formulae:

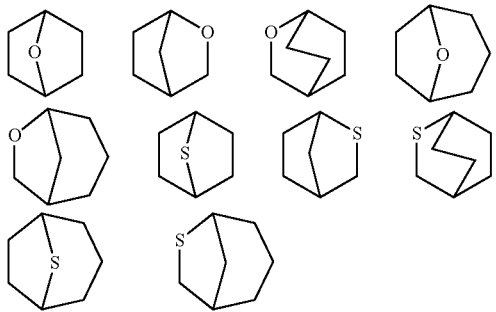

wherein the bonding position of the bicyclic ring is not limited as long as it is chemically stable. E includes preferably phenyl group, 4-fluorophenyl group, 4-chlorophenyl group, 4-methylphenyl group, 4-ethylphenyl group, 4-methoxyphenyl group, 4-ethoxyphenyl group, 4-isopropoxyphenyl group, 4-trifluoromethylphenyl group, cyclopropyl group, cyclobutyl group, cyclopentyl group, cyclohexyl group, and groups of the following formulae:

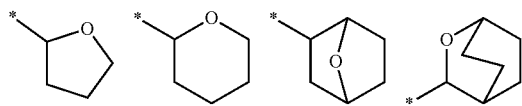

wherein * is the bonding position.

$R^6$ and $R^7$ are each independently hydrogen atom, deuterium atom, fluorine atom, or an optionally-substituted $C_{1-6}$ alkyl group; preferably hydrogen atom, deuterium atom, or fluorine atom; more preferably hydrogen atom or deuterium atom; even more preferably both of $R^6$ and $R^7$ are hydrogen atom. $R^6$ and $R^7$ specifically include hydrogen atom, deuterium atom, fluorine atom, methyl group, ethyl group, and hydroxymethyl group.

A is an optionally-substituted $C_{6-10}$ aryl group or an optionally-substituted 5- to 10-membered heteroaryl group; preferably an optionally-substituted $C_{6-10}$ aryl group. The optionally-substituted $C_{6-10}$ aryl group is preferably an optionally-substituted $C_6$ or $C_{10}$ aryl group, more preferably an optionally-substituted $C_6$ aryl group (phenyl group). The optionally-substituted 5- to 10-membered heteroaryl group is preferably an optionally-substituted 5- or 6-membered monocyclic group, or an optionally-substituted 9- or 10-membered bicyclic heteroaryl group; more preferably an optionally-substituted 5- or 6-membered monocyclic heteroaryl group.

Specific examples of A include preferably an optionally-substituted phenyl group and an optionally-substituted 1- and 2-naphthyl group; more preferably an optionally-substituted phenyl group.

The substituents of the optionally-substituted $C_{6-10}$ aryl group, optionally-substituted 5- to 10-membered heteroaryl group, optionally-substituted phenyl group, and optionally-substituted 1- or 2-naphthyl group in A include, for example, (i) a halogen atom such as fluorine atom and chlorine atom, (ii) a $C_{1-6}$ alkyl group optionally substituted with fluorine atom such as methyl group, ethyl group, propyl group, and trifluoromethyl group, (iii) a $C_{1-6}$ alkyloxy group optionally substituted with fluorine atom such as methoxy group, ethoxy group, isopropoxy group, and trifluoromethoxy group, (iv) a $C_{1-6}$ alkylthio group such as methylthio group and ethylthio group, (v) cyano group, and (vi) hydroxy group; preferably a halogen atom, methyl group, methoxy group, and cyano group; more preferably a halogen atom (preferably fluorine atom and chlorine atom), methyl group, and cyano group; even more preferably fluorine atom and chlorine atom. As used herein, one or more of the same or different substituents may exist at any position as long as the substitution is possible. In addition, the $C_{6-10}$ aryl group and the 5- to 10-membered heteroaryl group may form a fused ring with a $C_{3-8}$ cycloalkyl, $C_{4-8}$ cycloalkenyl, or 5- to 10-membered saturated heterocyclic group.

The optionally-substituted phenyl group includes, for example, the following formulae:

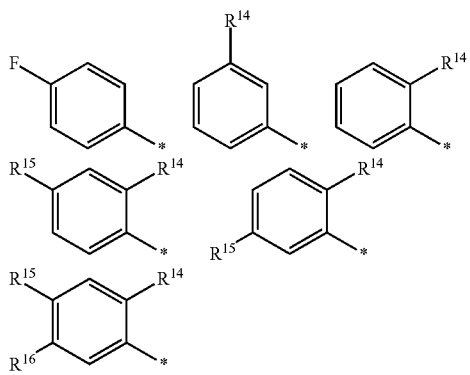

wherein
$R^{14}$, $R^{15}$, and $R^{16}$ are each independently a halogen atom, a $C_{1-6}$ alkyl group optionally substituted with fluorine atom, a $C_{1-6}$ alkyloxy group optionally substituted with fluorine atom, and cyano group, and
* is the bonding position.

L is oxygen atom, sulfur atom, or —$NR^{10}$—; preferably oxygen atom or sulfur atom; more preferably oxygen atom.

$R^{10}$ is hydrogen atom, a $C_{1-6}$ alkyl group, or a $C_{3-8}$ cycloalkyl group; preferably hydrogen atom or a $C_{1-6}$ alkyl group; more preferably hydrogen atom or a $C_{1-3}$ alkyl group.

$R^{10}$ specifically includes hydrogen atom, methyl group, ethyl group, n-propyl group, butyl group, pentyl group, hexyl group, cyclopropyl group, cyclobutyl group, cyclopentyl group, and cyclohexyl group; preferably hydrogen atom and methyl group.

X is hydrogen atom, a $C_{1-6}$ alkyl group optionally substituted with fluorine atom, or a halogen atom, and includes, for example, hydrogen atom, fluorine atom, chlorine atom, and methyl group. X is preferably hydrogen atom or a halogen atom, more preferably hydrogen atom.

n is 1, 2, or 3; preferably 1 or 2; more preferably 1.

One embodiment of a compound of Formula (1) may be the embodiment illustrated as follows:

a compound of Formula (1), or a pharmaceutically acceptable salt thereof, wherein $R^1$ and $R^2$ are each independently hydrogen atom, a $C_{1-6}$ alkyl group, or a $C_{1-6}$ alkyl group substituted with 1 to 3 deuterium atoms, $R^3$ and $R^4$ are each independently hydrogen atom, deuterium atom, or methyl group, $R^5$ is an optionally-substituted $C_{4-7}$ alkyl group or —$(CR^8R^9)_r$-E, $R^6$ and $R^7$ are each independently hydrogen atom or deuterium atom, $R^8$ and $R^9$ are each independently hydrogen atom, fluorine atom, or an optionally-substituted $C_{1-6}$ alkyl group, A is an optionally-substituted $C_{6-10}$ aryl group or an optionally-substituted 5- to 10-membered heteroaryl group, r is 1 or 2, E is an optionally-substituted $C_{3-8}$ cycloalkyl group, an optionally-substituted $C_{4-8}$ cycloalkenyl group, an optionally-substituted 5- to 10-membered saturated heterocyclic group which comprises 1 to 3 heteroatoms selected from the group consisting of oxygen atom and sulfur atom as a constituent atom of the ring, an optionally-substituted $C_{6-10}$ aryl group, or an optionally-substituted 5- to 10-membered heteroaryl group, L is oxygen atom or sulfur atom, n is 1, and X is hydrogen atom, a $C_{1-6}$ alkyl group optionally substituted with fluorine atom, or a halogen atom.

Another embodiment includes a compound of Formula (1), or a pharmaceutically acceptable salt thereof, wherein $R^1$ and $R^2$ are each independently hydrogen atom, a $C_{1-6}$ alkyl group, or a $C_{1-6}$ alkyl group substituted with 1 to 3 deuterium atoms, $R^3$ and $R^4$ are each independently hydrogen atom or deuterium atom, $R^5$ is an optionally-substituted $C_{4-7}$ alkyl group or —$(CR^8R^9)_r$-E, $R^6$ and $R^7$ are each independently hydrogen atom or deuterium atom, $R^8$ and $R^9$ are each independently hydrogen atom, fluorine atom, or an optionally-substituted $C_{1-6}$ alkyl group, A is an optionally-substituted $C_{6-10}$ aryl group, r is 1 or 2, E is an optionally-substituted $C_{3-8}$ cycloalkyl group, an optionally-substituted 5- to 10-membered saturated heterocyclic group wherein the saturated heterocyclic group includes 1 to 3 oxygen atoms as a constituent atom of the ring, or an optionally-substituted $C_{6-10}$ aryl group, L is oxygen atom, n is 1, and X is hydrogen atom.

Still another embodiment includes a compound of Formula (1), or a pharmaceutically acceptable salt thereof, wherein one of $R^1$ or $R^2$ is hydrogen atom, and the other is a $C_{1-6}$ alkyl group, for example, methyl group, $R^5$ is an optionally-substituted $C_{4-7}$ alkyl group (e.g., isobutyl group, 2,2-dimethylpropyl group, 3-methylbutyl group, 3,3-dimethylbutyl group, and 2-ethylbutyl group), or —$CH_2$-E, $R^3$, $R^4$, $R^6$, and $R^7$ are hydrogen atom, A is an optionally-substituted $C_{6-10}$ aryl group (e.g., phenyl group and naphthyl group), E is an optionally-substituted $C_{3-8}$ cycloalkyl group (e.g., cyclopropyl, cyclobutyl, cyclopentyl group, and cyclohexyl group) or an optionally-substituted $C_{6-10}$ aryl group (e.g., phenyl group and naphthyl group), L is oxygen atom, n is 1, and X is hydrogen atom.

Still another embodiment includes a compound of Formula (1), or a pharmaceutically acceptable salt thereof, wherein $R^1$ and $R^2$ are each independently hydrogen atom, a $C_{1-6}$ alkyl group optionally substituted with 1 to 3 deuterium atoms, or a $C_{3-6}$ cycloalkyl group, $R^3$ and $R^4$ are each independently hydrogen atom, deuterium atom, or methyl group, $R^5$ is an optionally-substituted $C_{4-7}$ alkyl group (e.g., n-butyl group, isobutyl group, 2,2-dimethylpropyl group, 3-methylbutyl group, 3,3-dimethylbutyl group, and 2-ethylbutyl group), or —$(CR^8R^9)_r$-E, wherein a substituent on the $C_{4-7}$ alkyl group is 1 to 3 groups independently selected from the group consisting of, for example, a halogen atom and methoxy group, $R^6$ and $R^7$ are each independently hydrogen atom, deuterium atom, or fluorine atom, $R^8$ and $R^9$ are each independently hydrogen atom, or a $C_{1-6}$ alkyl group optionally substituted with the same or different 1 to 3 halogen atoms, A is an optionally-substituted $C_{6-10}$ aryl group wherein a substituent on the $C_{6-10}$ aryl group is 1 to 3 groups independently selected from the group consisting of, for example, a halogen atom, methyl group, and cyano group, r is 1 or 2, E is an optionally-substituted $C_{3-8}$ cycloalkyl group (e.g., cyclopropyl group, cyclobutyl group, cyclopentyl group, cyclohexyl group, and norbornyl group); a 5- to 10-membered saturated heterocyclic group comprising 1 to 3 oxygen atoms as a constituent atom of the ring (e.g., tetrahydropyranyl group, 2-oxabicyclo[2.2.2]octyl group, and the following group:

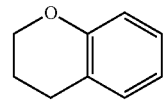

or an optionally-substituted $C_{6-10}$ aryl group, wherein a substituent on the $C_{3-8}$ cycloalkyl group is 1 to 2 groups independently selected from the group consisting of, for example, a halogen atom, methyl group, and trifluoromethyl group, and a substituent on the $C_{6-10}$ aryl group is 1 to 2 groups independently selected from the group consisting of, for example, a halogen atom, methyl group, and methoxy group, L is oxygen atom, n is 1, and X is hydrogen atom.

A pharmaceutically acceptable salt of a compound of Formula (1) is a typically-used nontoxic salt including, for example, acid addition salts such as organic acid salts (e.g., acetate, propionate, trifluoroacetate, maleate, fumarate, citrate, succinate, tartrate, methanesulfonate, benzenesulfonate, formate, and toluenesulfonate) and inorganic acid salts (e.g., hydrochloride, hydrobromide, hydroiodide, sulfate, nitrate, and phosphate); salts with amino acids such as arginine acid, aspartic acid, and glutamic acid; metal salts such as alkali metal salts (e.g., sodium salt and potassium salt) and alkaline earth metal salts (e.g., calcium salt and magnesium salt); ammonium salts; and organic base salts (e.g., trimethylamine salt, triethylamine salt, pyridine salt, picoline salt, dicyclohexylamine salt, and N,N'-dibenzylethylenediamine salt). The pharmaceutically acceptable salt is preferably hydrochloride, phosphate, trifluoroacetate, citrate, or succinate.

The present compound may be in the form of its solvate such as hydrate.

The present compound can show a high binding affinity (antagonism or inverse agonist action) for human serotonin 5-HT$_{2A}$ receptor, serotonin 5-HT$_{2C}$ receptor, and serotonin transporter (SERT). Based on the binding-affinity profile, the present compound can be useful as a medicament for treating a disease mediated by serotonergic system or dopaminergic system, particularly non-motor symptoms associated with Parkinson's disease, and/or preventing a relapse thereof. In the present compound, a compound that does not show the affinity for dopamine D$_{2L}$ receptor can be advantageous in view of fewer adverse effects such as exacerbations of motor symptoms in Parkinson's disease.

The disease mediated by serotonergic system or dopaminergic system herein includes F00-F09: organic mental disorder including symptomatic one, F10-F19: mental and behavioral disorders caused by use of psychotropic substances, F45: somatoform disorder, F84: pervasive development disorder, F90-F98: behavioral and emotional disorder typically developed in childhood and adolescence, F99: unspecified psychopathic disorder, G10: Huntington disease, G20-G26: extrapyramidal disturbance and abnormal movement, G30-G32: other degenerative diseases of nervous system, M79: fibromyalgia encompassed in other soft-tissue disorders or other unclassified disorders, and R45: symptoms and signs involving emotional state, as listed in International Statistical Classification of Diseases and Related Health Problems 10th edition (ICD-10). Specifically, F00-F09: organic mental disorder including symptomatic one includes, for example, Alzheimer disease, vascular dementia, Lewy body dementia, dementia in Parkinson's disease, psychopathic disorder associated with diseases such as brain injury, and other psychopathic disorders caused by brain dysfunction or physical disorder. F10-F19: Psychopathic and behavioral disorder caused by use of psychotropic substances includes, for example, delirium tremens, psychotic disorder, and amnestic syndrome, which are caused by use of various substances. F45: Somatoform disorder includes, for example, somatization disorder, hypochondriacal disorder, somatoform disorder, and persistent somatoform pain disorder. F84: Pervasive development disorder includes, for example, autism, hypophrenia, and hyperactivity disorder associated with stereotyped movement. F90-F98: Behavioral and emotional disorder typically developed in childhood and adolescence includes, for example, hyperactivity disorder, behavioral disorder, and mixed disturbance of behavior and emotion. G20-G26: Extrapyramidal disturbance and abnormal movement includes, for example, Parkinson's disease and secondary parkinsonism. G30-G32: Other degenerative diseases of nervous system include, for example, Alzheimer disease, frontotemporal dementia, frontotemporal degeneration, Lewy body dementia, and senile cerebral degeneration. R45: Symptoms and signs involving emotional state include, for example, nervous erethism, emotional anxiety and agitation, funk, and other symptoms and signs associated with emotional conditions.

The present compound may be useful for treating these diseases, particularly various conditions associated with Parkinson's disease, e.g., psychopathic symptoms such as hallucination and delusion, and non-motor symptoms such as sleep-wake cycle abnormity (sleep disorder), depressive symptoms, anxiety symptoms, cognitive dysfunction, autonomic disorder, pain, edema, and impaired sense of smell and/or preventing a relapse thereof. The present compound may also be useful for treating various conditions associated with Alzheimer disease, e.g., psychopathic symptoms, depressive symptoms, anxiety disorder, agitation symptoms, and sleep disorder, and/or preventing a relapse thereof.

The "inverse agonist action" used herein means a stimulating action so as to inhibit a receptor. The "antagonism" used herein means an action where a substance binds to a receptor to inhibit activation. Both an inverse agonist and antagonist show an inhibitory action against the receptor.

Although there is no animal model that mimics depressive symptoms and anxiety symptoms in Parkinson's disease, it is considered that the efficacy on depressive symptoms or anxiety symptoms in Parkinson's disease can be evaluated with the drug efficiency evaluation models described in Tests 3 and 4. The present compound is considered to be generally useful for treating depression and anxiety disorders including depressive symptoms and anxiety symptoms in Parkinson's disease, and/or preventing a relapse thereof because that showed marked antidepressant effect and anxiolytic effect in Tests 3 and 4.

In these evaluation models, not only SSRI that is used for treatment of depressive symptoms associated with various diseases but also various antidepressants such as noradrenergic and specific serotonergic antidepressants (NaSSA) and serotonin- and noradrenaline-selective reuptake inhibitors have been reported to show drug efficacy, in addition to imipramine and diazepam that were used as a positive control in Tests 3 and 4 (Non Patent Literature 17).

Doses of the present compound may vary depending on the age and conditions of patients; and in general, when it is administered to humans, about 0.1 mg to about 1,000 mg, preferably about 1 mg to about 100 mg, can be administered as a daily dose per an individual patient. The administration may be once or several times a day, and each administration may include 1, 2, or 3 doses.

The present compound can be administered orally or parenterally (e.g., intravenously, subcutaneously, intramuscularly, intrathecally, topically, transrectally, percutaneously, nasally, and pulmonarily) as a pharmaceutical composition. Oral dosage forms include, for example, tablets, capsules, pills, granules, fine granules, powders, solutions, syrups, and suspensions; and parenteral dosage forms include, for example, aqueous injections, non aqueous injections, suppositories, nasal preparations, transdermal preparations such as lotions, emulsion, ointments, creams, jellies, gels, adhesive skin patches (e.g., tapes, transdermal patches, and poultices), topical powders, and the like. These formulations can be formulated according to conventionally well-known techniques, and they may comprise nontoxic and inactive carriers which are typically used in the field of formulation.

The carriers used for formulation include substances typically used in the field of formulation which react with neither a compound of Formula (1) nor a pharmaceutically acceptable salt thereof. That is, a pharmaceutical composition comprising a compound of Formula (1) or a pharmaceutically acceptable salt thereof may further contain carriers used for formulation such as excipients, binders, lubricants, stabilizers, disintegrants, buffers, solubilizers, tonicity agents, pH adjusters, surfactants, emulsifying agents, suspending agents, dispersants, suspension stabilizers, thickeners, viscosity modifiers, gelling agents, soothing agents, preservatives, plasticizers, transdermal-absorption promoters, antioxidants, humectants, antiseptics, flavors, and the like. Furthermore, a pharmaceutical composition may optionally comprise a mixture of two or more of the above-listed carriers used for formulation.

Solid formulations such as tablets can be formulated by mixing an active ingredient, the present compound, with carriers used for formulation, for example, excipients (e.g., lactose, sucrose, and corn starch); binders (e.g., crystalline cellulose, hydroxypropylcellulose, polyvinylpyrrolidone, and hydroxypropyl methylcellulose); disintegrants (e.g., carboxymethylcellulose sodium and sodium carboxymethyl starch); lubricants (e.g., stearic acid and magnesium stearate); and preservatives.

For parenteral dosage forms, an active ingredient may be dissolved or suspended in physiologically acceptable carriers such as water, saline, oil, and aqueous glucose solution; and if necessary, adjuvants such as emulsifying agents, stabilizing agents, salts for regulating osmotic pressure, and/or buffers may be added thereto.

A pharmaceutical composition may be prepared as a formulation according to conventional methods. For example, a pharmaceutical composition may comprise the present compound as an active ingredient in a therapeutically effective amount of, for example, 0.05 wt % to 99 wt %, preferably 0.05 wt % to 80 wt %, more preferably 0.1 wt % to 70 wt %, even more preferably 0.1 wt % to 50 wt %, per formulation. The formulation may comprise other ingredients which are efficacious for the treatment.

A formulation comprising the present compound, for example tablets, can be formulated by mixing 20 mg of the compound of Example 1, 100 mg of lactose, 25 mg of crystalline cellulose, and 1 mg of magnesium stearate, and then compressing the mixture.

For the purpose of enhancing efficacy, the present compound may be used in combination with medicaments such as antidepressants, anxiolytic drugs, antipsychotic drugs, dopamine replacement drugs, dopamine receptor agonists, antiparkinsonian drugs, antiepilepsy drugs, anticonvulsant drugs, analgesic drugs, hormone preparations, antimigraine drugs, adrenergic β receptor antagonists, antidementia drugs, and therapeutic drugs for mood disorder. Preferably, the present compound may be used in combination with medicaments such as antidepressants, anxiolytic drugs, antipsychotic agents, dopamine replacement drugs, dopamine receptor agonists, antiparkinsonian drugs, antidementia drugs, and therapeutic drugs for mood disorder. Furthermore, for the purpose of reducing side effects, the present compound may be used in combination with medicaments such as antiemetic drugs, sleep-inducing drugs, and anticonvulsants. The timing of administration of the present compound and the above additional medicaments (also referred to as "combined medicament(s)" hereinafter) are not limited, and thus they may be administered simultaneously or sequentially with a certain time interval to a subject. Furthermore, the present compound and the combined medicaments may be administered in the form of a single compound drug comprising them. The dose of a combined medicament may vary, and can be optionally determined on the basis of the amount used in clinical practice. The administration or combination ratio of the present compound and a combined medicament can be optionally determined on the basis of, for example, a subject to be administered, administration route, disease, symptom, or a combination thereof. For example, when a subject is human, 0.01 to 1000 parts by volume of a combined medicament per 1 part by volume of the present compound may be used.

EXAMPLES

Hereinafter, the present invention is illustrated in more detail by Reference examples, Examples, and Tests, but the technical scope of the present invention should not be limited thereto. In addition, the compound names shown in the Reference Examples and Examples below do not necessarily follow the IUPAC nomenclature system.

The following abbreviations may be used herein.
DMSO: dimethylsulfoxide
DMF: N,N-dimethylformamide
THF: tetrahydrofuran
Tol: toluene
Ac: acetyl
Boc: tert-butoxycarbonyl
Ms: methanesulfonyl
Ts: toluenesulfonyl
Preparation The compounds of Examples shown in the following table were prepared according to methods described in Patent Literature 1 (WO 2012/008528). Compounds were identified by proton nuclear magnetic resonance spectra ($^1$H-NMR spectra) and mass spectra (LC-MS). Specific optical rotations were also measured for optically active substances. In the LC-MS analysis, the mass spectra of molecules protonated by electro spray ionization were observed.

| Example | Structure | Mass analysis Observed [M + 1]/ $^1$H-NMR spectra/specific optical rotation |
|---|---|---|
| 1 | 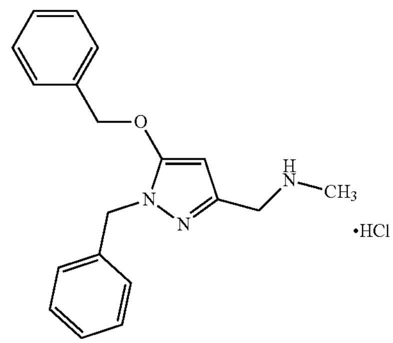 [SMILES: CNCc1cc(OCc2ccccc2)n(Cc2ccccc2)n1 ; Cl] | 308.4 |
| 4 | 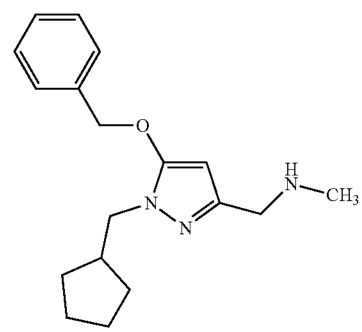 [SMILES: CNCc1cc(OCc2ccccc2)n(CC2CCCC2)n1] | 300.3 |
| 5 | 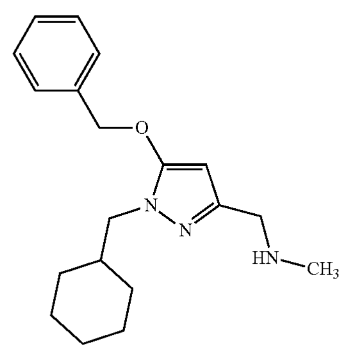 [SMILES: CNCc1cc(OCc2ccccc2)n(CC2CCCCC2)n1] | 314.3 |
| 20 | 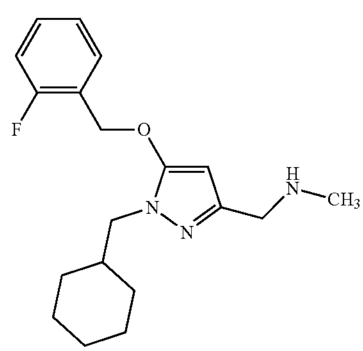 [SMILES: CNCc1cc(OCc2ccccc2F)n(CC2CCCCC2)n1] | 332.5 |

-continued

| Example | Structure | Mass analysis Observed [M + 1]/ ¹H-NMR spectra/specific optical rotation |
|---|---|---|
| 21 | 3-fluorobenzyl ether of pyrazole with cyclohexylmethyl on N and CH₂NHCH₃ | 332.5 |
| 22 | 4-fluorobenzyl ether analog | 332.5 |
| 23 | 2-chlorobenzyl ether analog ·HCl | 348.5 |
| 24 | 3-chlorobenzyl ether analog ·HCl | 348.5 |

-continued
| Example | Structure | Mass analysis Observed [M + 1]/ ¹H-NMR spectra/specific optical rotation |
|---|---|---|
| 26 | 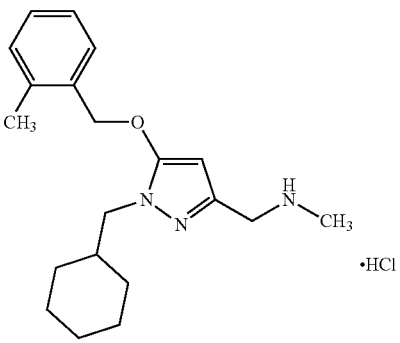 [SMILES: CNCc1cc(OCc2ccccc2C)n(CC2CCCCC2)n1 ; Cl] •HCl | 328.3 |
| 27 | 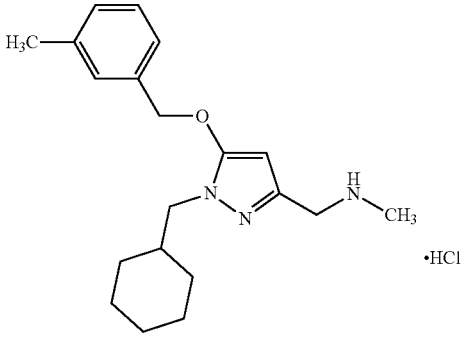 •HCl | 328.6 |
| 29 | 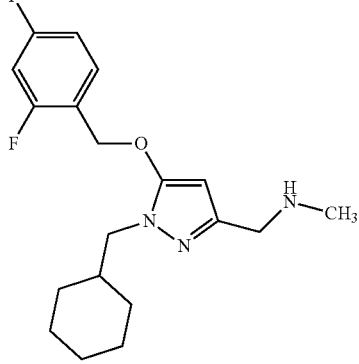 | 350.2 |
| 30 | 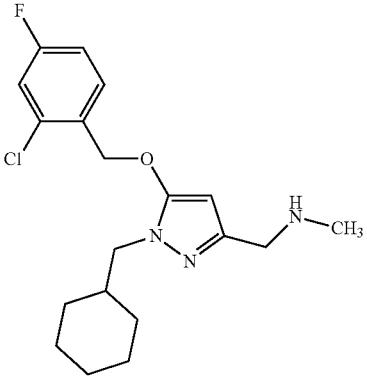 [SMILES: CNCc1cc(OCc2ccc(F)cc2Cl)n(CC2CCCCC2)n1] | 366.2 |

-continued

| Example | Structure | Mass analysis Observed [M + 1]/ ¹H-NMR spectra/specific optical rotation |
|---|---|---|
| 31 | (4-fluoro-2-methylbenzyl ether of pyrazole with cyclohexylmethyl and methylaminomethyl) | 346.2 |
| 33 | (2,5-difluorobenzyl ether of pyrazole with cyclohexylmethyl and methylaminomethyl) ·HCl | 350.7 |
| 34 | (5-chloro-2-fluorobenzyl ether of pyrazole with cyclohexylmethyl and methylaminomethyl) ·HCl | 366.1 |
| 35 | (2-fluoro-5-methylbenzyl ether of pyrazole with cyclohexylmethyl and methylaminomethyl) ·HCl | 346.2 |

-continued
| Example | Structure | Mass analysis Observed [M + 1]/ ¹H-NMR spectra/specific optical rotation |
|---|---|---|
| 37 | 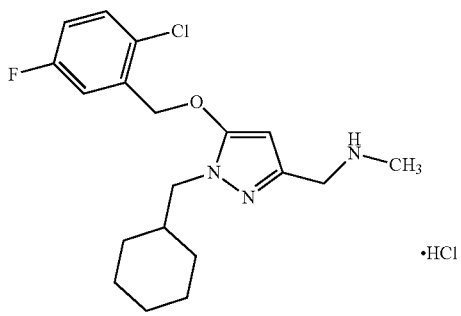 [SMILES: CNCc1cc(OCc2cc(F)ccc2Cl)n(CC2CCCCC2)n1 ; Cl] ·HCl | 366.1 |
| 38 | 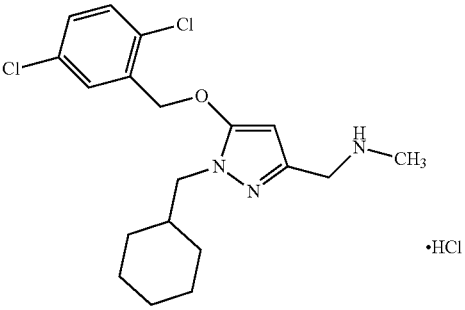 [SMILES: CNCc1cc(OCc2cc(Cl)ccc2Cl)n(CC2CCCCC2)n1 ; Cl] ·HCl | 382.4 |
| 39 | 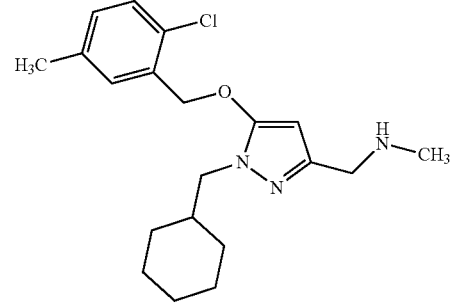 | 362.5 |
| 108 | 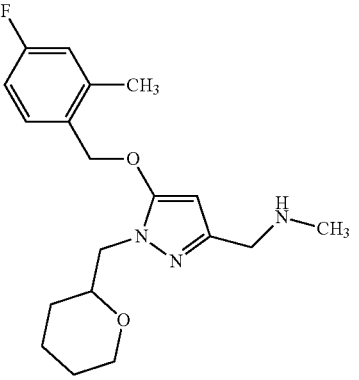 [SMILES: CNCc1cc(OCc2ccc(F)cc2C)n(CC2CCCCO2)n1] | 348.2 |

-continued

| Example | Structure | Mass analysis Observed [M + 1]/ ¹H-NMR spectra/specific optical rotation |
|---|---|---|
| 115 | 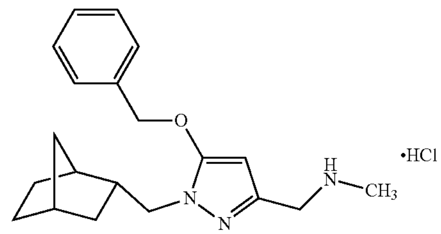 [SMILES: CNCc1cc(OCc2ccccc2)n(CC2CC3CCC2C3)n1 ; Cl] | 326.4 |
| 117 | 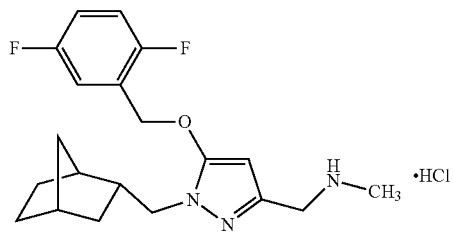 [SMILES: CNCc1cc(OCc2cc(F)ccc2F)n(CC2CC3CCC2C3)n1 ; Cl] | 362.5 |
| 118 | 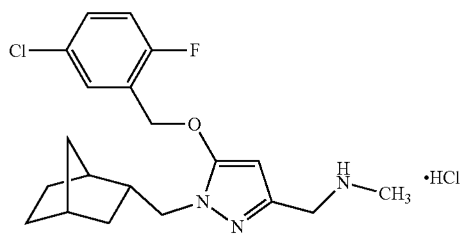 [SMILES: CNCc1cc(OCc2cc(Cl)ccc2F)n(CC2CC3CCC2C3)n1 ; Cl] | 378.5 |
| 124 | 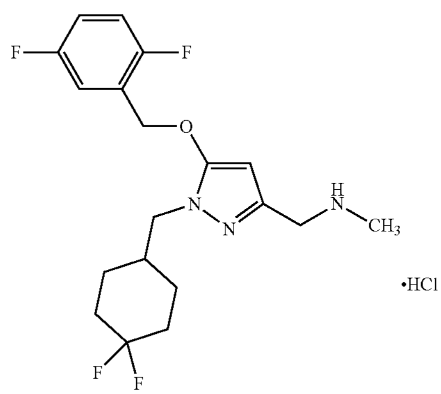 [SMILES: CNCc1cc(OCc2cc(F)ccc2F)n(CC2CCC(F)(F)CC2)n1 ; Cl] | 386.6 |
| 127 | 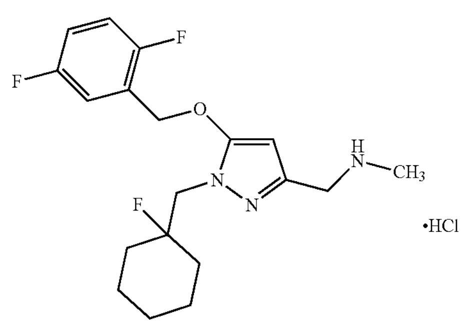 [SMILES: CNCc1cc(OCc2cc(F)ccc2F)n(CC2(F)CCCCC2)n1 ; Cl] | 368.4 |

-continued

| Example | Structure | Mass analysis Observed [M + 1]/ ¹H-NMR spectra/specific optical rotation |
|---|---|---|
| 131 | 5-[(5-chloro-2-fluorobenzyl)oxy]-1-(cyclopropylmethyl)-N-methyl-1H-pyrazol-3-yl]methanamine · HCl | 324.4 |
| 135 | 1-(cyclopentylmethyl)-5-[(2-fluorobenzyl)oxy]-N-methyl-1H-pyrazol-3-yl]methanamine · CF₃CO₂H | 317.9 |
| 136 | 1-(cyclopentylmethyl)-5-[(3-fluorobenzyl)oxy]-N-methyl-1H-pyrazol-3-yl]methanamine · HCl | 318.2 |
| 137 | 1-(cyclopentylmethyl)-5-[(4-fluorobenzyl)oxy]-N-methyl-1H-pyrazol-3-yl]methanamine · CF₃CO₂H | 318.0 |

-continued

| Example | Structure | Mass analysis Observed [M + 1]/ ¹H-NMR spectra/specific optical rotation |
|---|---|---|
| 138 | 2-Cl-C6H4-CH2-O-pyrazole(N-CH2-cyclopentyl)-CH2-NH-CH3 ·CF3CO2H | 333.9 |
| 139 | 3-Cl-C6H4-CH2-O-pyrazole(N-CH2-cyclopentyl)-CH2-NH-CH3 ·HCl | 334.2 |
| 141 | 2-CH3-C6H4-CH2-O-pyrazole(N-CH2-cyclopentyl)-CH2-NH-CH3 ·CF3CO2H | 313.9 |
| 142 | 3-CH3-C6H4-CH2-O-pyrazole(N-CH2-cyclopentyl)-CH2-NH-CH3 ·HCl | 314.3 |

-continued
| Example | Structure | Mass analysis Observed [M + 1]/ $^1$H-NMR spectra/specific optical rotation |
|---|---|---|
| 144 | 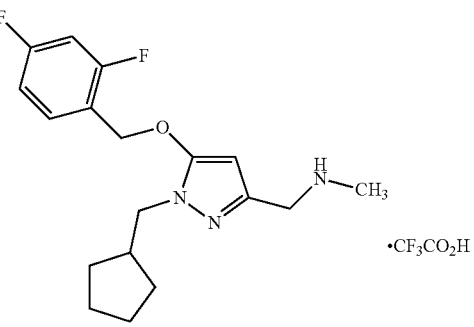 ·CF$_3$CO$_2$H | 335.9 |
| 145 | 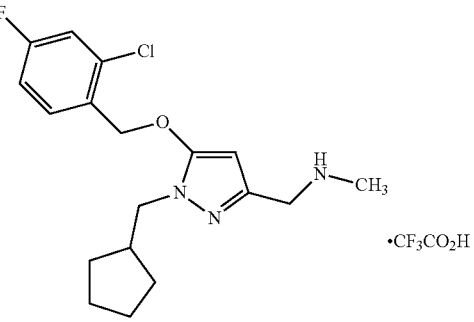 ·CF$_3$CO$_2$H | 351.8 |
| 146 | 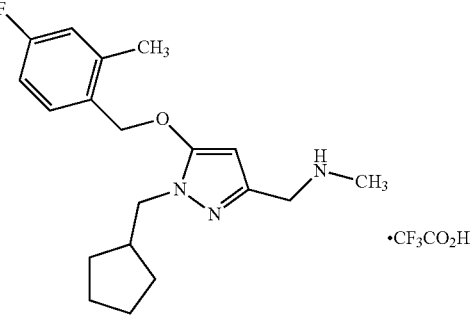 ·CF$_3$CO$_2$H | 331.8 |
| 147 | 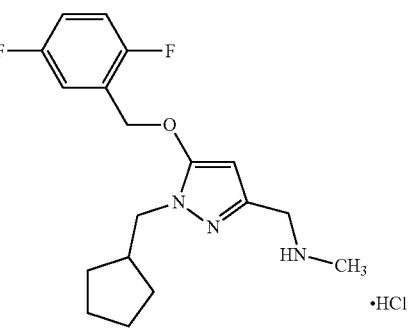 ·HCl | 336.4 |

-continued

| Example | Structure | Mass analysis Observed [M + 1]/ ¹H-NMR spectra/specific optical rotation |
|---|---|---|
| 148 | (5-chloro-2-fluorobenzyl ether pyrazole with cyclopentylmethyl and N-methylaminomethyl) ·HCl | 352.4 |
| 149 | (2-fluoro-5-methylbenzyl ether pyrazole with cyclopentylmethyl and N-methylaminomethyl) ·CF₃CO₂H | 331.9 |
| 150 | (2-chloro-5-fluorobenzyl ether pyrazole with cyclopentylmethyl and N-methylaminomethyl) ·CF₃CO₂H | 351.9 |
| 151 | (2,5-dichlorobenzyl ether pyrazole with cyclopentylmethyl and N-methylaminomethyl) ·CF₃CO₂H | 367.7 |
| 152 | (2-chloro-5-methylbenzyl ether pyrazole with cyclopentylmethyl and N-methylaminomethyl) ·CF₃CO₂H | 348.1 |

-continued

| Example | Structure | Mass analysis Observed [M + 1]/ ¹H-NMR spectra/specific optical rotation |
|---|---|---|
| 162 | 2-cyanobenzyl ether of 1-(cyclopentylmethyl)-5-hydroxy-N-methyl-1H-pyrazole-3-methanamine · CF₃CO₂H | 324.8 |
| 218 | 2-fluorobenzyl ether of 1-(4-fluorobenzyl)-5-hydroxy-N-methyl-1H-pyrazole-3-methanamine · HCl | 344.1 |
| 219 | 2,5-difluorobenzyl ether of 1-(4-fluorobenzyl)-5-hydroxy-N-methyl-1H-pyrazole-3-methanamine · HCl | 362.1 |
| 224 | 2,5-difluorobenzyl ether of 1-(4-chlorobenzyl)-5-hydroxy-N-methyl-1H-pyrazole-3-methanamine · HCl | 378.5 |

-continued

| Example | Structure | Mass analysis Observed [M + 1]/ ¹H-NMR spectra/specific optical rotation |
|---|---|---|
| 228 | 2-fluorobenzyloxy-1-(4-methylbenzyl)-3-(methylaminomethyl)pyrazole · HCl | 340.4 |
| 230 | 2,5-difluorobenzyloxy-1-(4-methylbenzyl)-3-(methylaminomethyl)pyrazole · HCl | 358.3 |
| 242 | 2,5-difluorobenzyloxy-1-butyl-3-(methylaminomethyl)pyrazole · HCl | 310.4 |
| 256 | 5-chloro-2-fluorobenzyloxy-1-isobutyl-3-(methylaminomethyl)pyrazole · HCl | 326.4 |

-continued
| Example | Structure | Mass analysis Observed [M + 1]/ ¹H-NMR spectra/specific optical rotation |
|---|---|---|
| 258 | 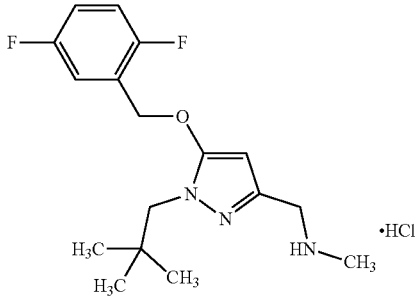 [SMILES: CNCc1cc(OCc2cc(F)ccc2F)n(CC(C)(C)C)n1 ; Cl] | 324.4 |
| 259 | 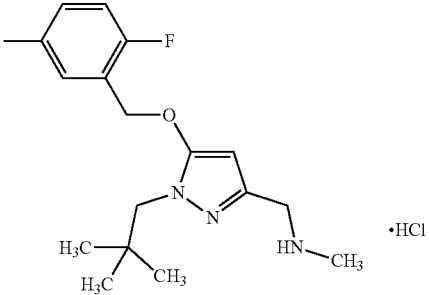 | 340.4 |
| 263 | 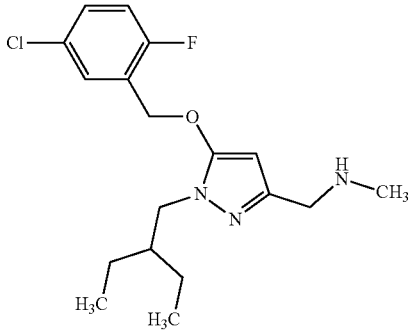 [SMILES: CCC(CC)Cn1nc(CNC)cc1OCc1cc(Cl)ccc1F] | 354.4 |
| 264 | 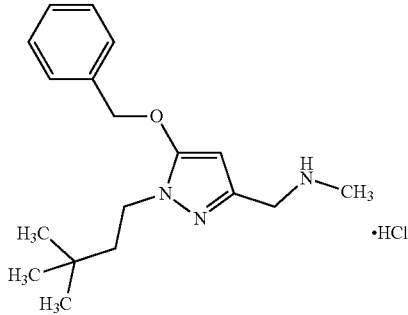 [SMILES: CNCc1cc(OCc2ccccc2)n(CCC(C)(C)C)n1 ; Cl] | 302.5 |

-continued

| Example | Structure | Mass analysis Observed [M + 1]/ ¹H-NMR spectra/specific optical rotation |
|---|---|---|
| 265 | 3-chlorobenzyloxy pyrazole with 3,3-dimethylbutyl N1 substituent and CH₂NHCH₃ at C3 ·HCl | 336.4 |
| 266 | 2,5-difluorobenzyloxy pyrazole with 3,3-dimethylbutyl N1 substituent and CH₂NHCH₃ at C3 ·HCl | 338.4 |
| 267 | 5-chloro-2-fluorobenzyloxy pyrazole with 3,3-dimethylbutyl N1 substituent and CH₂NHCH₃ at C3 ·HCl | 354.3 |
| 268 | benzyloxy pyrazole with 3-methylbutyl N1 substituent and CH₂NHCH₃ at C3 ·HCl | 288.3 |

-continued

| Example | Structure | Mass analysis Observed [M + 1]/ ¹H-NMR spectra/specific optical rotation |
|---|---|---|
| 269 | 2,5-difluorobenzyloxy pyrazole with N-(3-methylbutyl) and CH₂NHCH₃·HCl | 324.4 |
| 270 | 5-chloro-2-fluorobenzyloxy pyrazole with N-(3-methylbutyl) and CH₂NHCH₃·HCl | 340.4 |
| 274 | 2,5-difluorobenzyloxy pyrazole with N-(3-methoxy-3-methylbutyl) and CH₂NHCH₃·HCl | 354.4 |
| 275 | 5-chloro-2-fluorobenzyloxy pyrazole with N-(3-methoxy-3-methylbutyl) and CH₂NHCH₃·HCl | 370.3 |

-continued

| Example | Structure | Mass analysis Observed [M + 1]/ ¹H-NMR spectra/specific optical rotation |
|---|---|---|
| 280 | (structure) | 354.4 |
| 283 | (structure) | ¹H-NMR (400 MHz, CDCl₃) δ: 0.88 (6H, d, J = 6.0 Hz), 1.40-1.70 (5H, m), 2.59 (3H, s), 3.91 (2H, d, J = 6.0 Hz), 4.06 (2H, s), 5.06 (2H, s), 6.11 (1H, s), 6.93-7.01 (1H, m), 7.22-7.35 (1H, m). |
| 284 | (structure) | ¹H-NMR (400 MHz, CDCl₃) δ: 0.90 (9H, s), 1.60-1.65 (2H, m), 2.59 (3H, s), 3.89-3.94 (2H, m), 4.07 (2H, s), 5.07 (2H, s), 6.13 (1H, s), 6.93-7.02 (1H, m), 7.25-7.35 (1H, m), 9.77 (2H, br s). |
| 285 | (structure) | ¹H-NMR (400 MHz, CDCl₃) δ: 2.58 (3H, s), 3.76 (3H, s), 4.06 (2H, s), 5.03 (2H, s), 5.03 (2H, s), 6.13 (1H, s), 6.80 (2H, d, J = 8.0 Hz), 6.90-6.96 (1H, m), 7.08 (2H, d, J = 8.0 Hz), 7.23-7.29 (1H, m), 9.79 (2H, br s). |

-continued
| Example | Structure | Mass analysis Observed [M + 1]/ ¹H-NMR spectra/specific optical rotation |
|---|---|---|
| 286 | 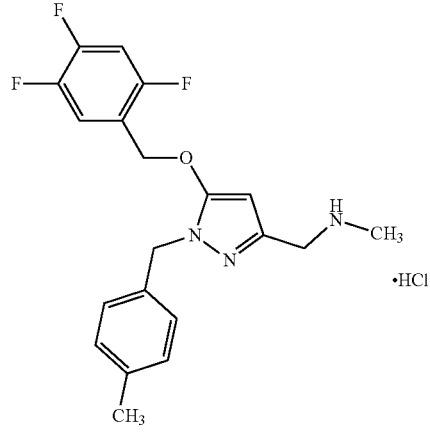 [SMILES: CNCc1cc(OCc2cc(F)c(F)cc2F)n(Cc2ccc(C)cc2)n1 ; Cl] | ¹H-NMR (400 MHz, CDCl₃) δ: 2.29 (3H, s), 2.58 (3H, s), 4.06 (2H, s), 5.03 (2H, s), 5.05 (2H, s), 6.14 (1H, s), 6.88-6.96 (1H, m), 7.01 (2H, d, J = 8.0 Hz), 7.08 (2H, d, J = 8.0 Hz), 7.21-7.26 (1H, m), 9.80 (2H, br s). |
| 288 | 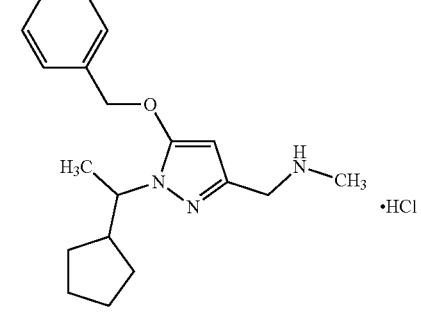 | ¹H-NMR (300 MHz, DMSO-d₆) δ: 0.90-1.03 (1H, m), 1.14-1.27 (2H, m), 1.31 (3H, d, J = 6.6 Hz), 1.34-1.63 (4H, m), 1.67-1.80 (1H, m), 2.16-2.30 (1H, m), 2.50 (3H, br s), 3.95 (2H, br, J = 5.6 Hz), 3.99-4.08 (1H, m), 5.14 (2H, s), 5.86 (1H, s), 7.32-7.46 (5H, m), 8.92 (2H, br s). |
| 291 | 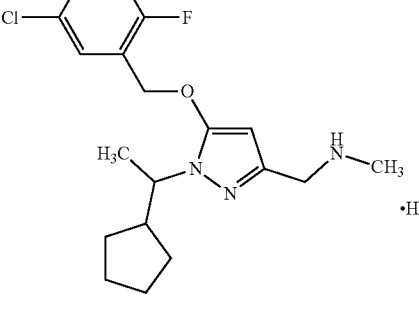 | ¹H-NMR (300 MHz, DMSO-d₆) δ: 0.86-0.98 (1H, m), 1.12-1.26 (2H, m), 1.29 (3H, d, J = 6.6 Hz), 1.33-1.60 (4H, m), 1.65-1.77 (1H, m), 2.20 (1H, br td, J = 17.1, 8.9 Hz), 2.50 (3H, br s), 3.91-4.03 (3H, m), 5.18 (2H, s), 5.93 (1H, s), 7.34 (1H, t, J = 9.2 Hz), 7.51 (1H, ddd, J = 8.8, 4.4, 2.8 Hz), 7.63 (1H, br dd, J = 6.2, 2.8 Hz), 8.99 (2H, br s). |
| 292 | 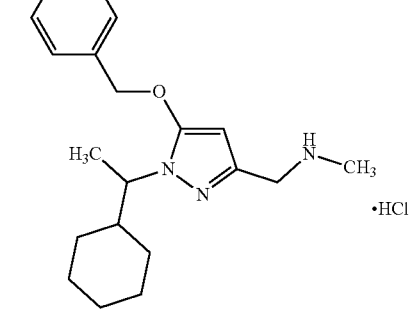 | 328.3 |

-continued
| Example | Structure | Mass analysis Observed [M + 1]/ $^1$H-NMR spectra/specific optical rotation |
|---|---|---|
| 293 | 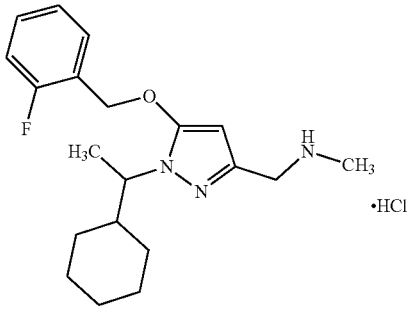 [SMILES: CNCc1cc(OCc2ccccc2F)n(C(C)C2CCCCC2)n1 ; Cl] ·HCl | 346.5 |
| 295 | 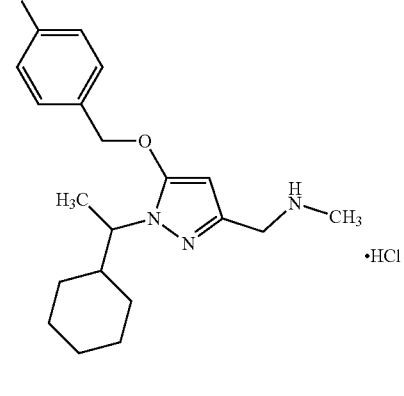 ·HCl | 346.2 |
| 296 | 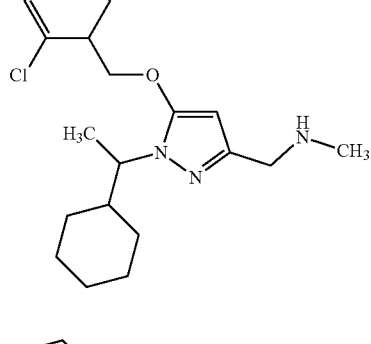 | 362.2 |
| 298 | 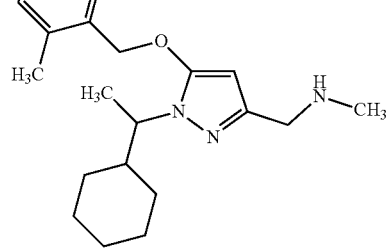 | 342.3 |

-continued

| Example | Structure | Mass analysis Observed [M + 1]/ ¹H-NMR spectra/specific optical rotation |
|---|---|---|
| 299 | 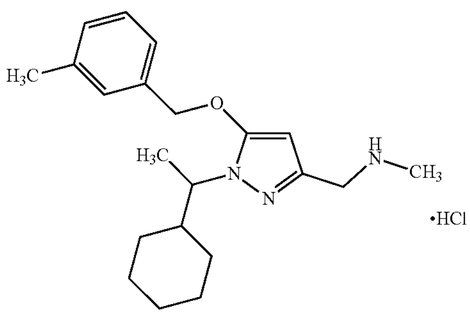 | 342.3 |
| 300 | 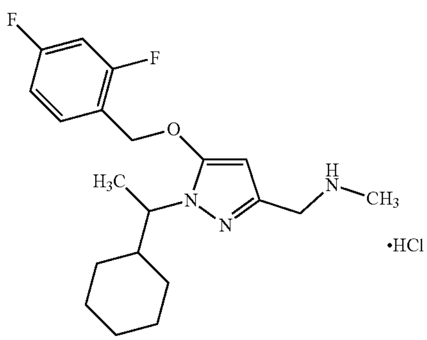 [SMILES: CNCc1cc(OCc2ccc(F)cc2F)n(C(C)C2CCCCC2)n1 ; Cl] | 364.5 |
| 301 | 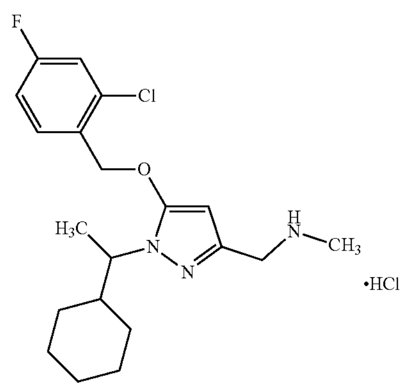 [SMILES: CNCc1cc(OCc2ccc(F)cc2Cl)n(C(C)C2CCCCC2)n1 ; Cl] | 380.2 |
| 302 | 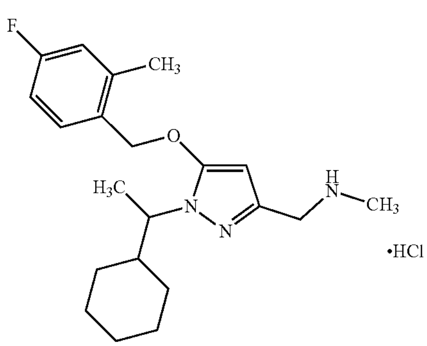 [SMILES: CNCc1cc(OCc2ccc(F)cc2C)n(C(C)C2CCCCC2)n1 ; Cl] | 360.5 |

-continued

| Example | Structure | Mass analysis Observed [M + 1]/ ¹H-NMR spectra/specific optical rotation |
|---|---|---|
| 303 | 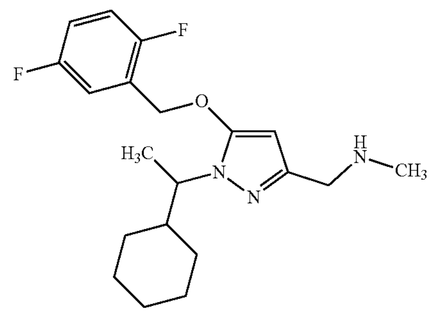 [SMILES: CNCc1cc(OCc2cc(F)ccc2F)n(C(C)C2CCCCC2)n1] | 364.2 |
| 304 | 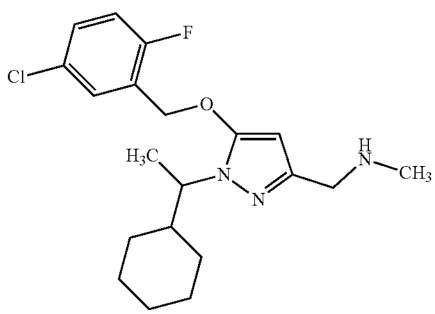 [SMILES: CNCc1cc(OCc2cc(Cl)ccc2F)n(C(C)C2CCCCC2)n1] | 380.4 |
| 305 | 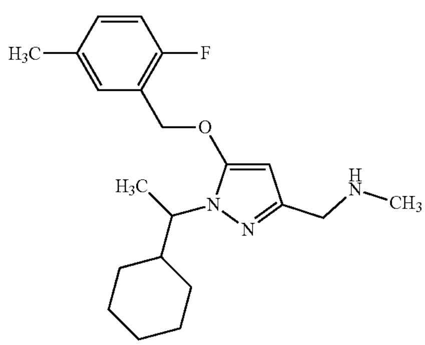 | 360.2 |
| 315 | 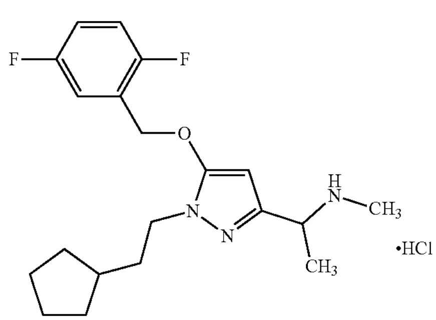 [SMILES: CNC(C)c1cc(OCc2cc(F)ccc2F)n(CCC2CCCC2)n1 ; Cl] | 364.5 |

| Example | Structure | Mass analysis Observed [M + 1]/ ¹H-NMR spectra/specific optical rotation |
|---|---|---|
| 330 | 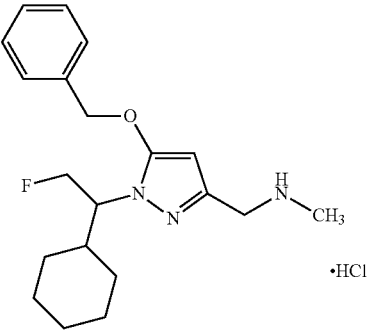 [SMILES: CNCc1cc(OCc2ccccc2)n(C(CF)C2CCCCC2)n1 ; Cl] | ¹H-NMR (300 MHz, CDCl₃) δ: 0.89 (1H, m), 0.96-1.33 (5H, m), 1.57-1.96 (5H, m), 2.59 (3H, s), 4.10 (2H, s), 4.27 (1H, m), 4.71 (1H, ddd, J = 45.8, 9.7, 4.0 Hz), 4.82 (1H, ddd, J = 48.2, 8.9, 8.9 Hz), 5.09 (2H, s), 6.10 (1H, s), 7.39 (5H, m), 9.77 (2H, br s). |
| 331 | 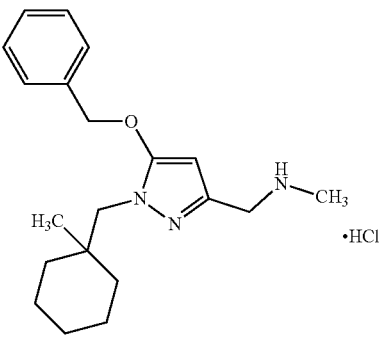 [SMILES: CNCc1cc(OCc2ccccc2)n(CC2(C)CCCCC2)n1 ; Cl] | 328.6 |
| 341 | 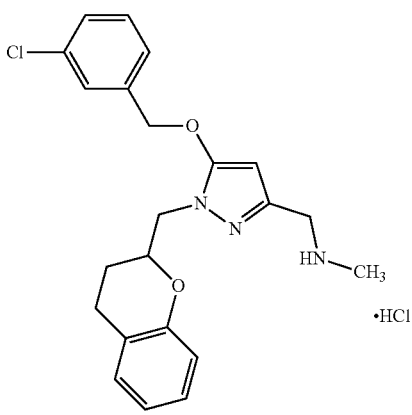 [SMILES: CNCc1cc(OCc2cccc(Cl)c2)n(CC2CCc3ccccc3O2)n1 ; Cl] | ¹H-NMR (400 MHz, DMSO-d6) δ: 1.64-1.74 (1H, m), 1.96-2.03 (1H, m), 2.54 (3H, br t, J = 4.3 Hz), 2.69-2.84 (2H, m), 3.98 (2H, br t, J = 5.2 Hz), 4.16 (1H, dd, J = 14.0, 5.0 Hz), 4.26 (1H, dd, J = 14.4, 6.8 Hz), 4.33-4.40 (1H, m), 5.21 (2H, s), 5.90-5.96 (1H, m), 6.65 (1H, br d, J = 8.0 Hz), 6.81 (1H, br t, J = 7.4 Hz), 7.01-7.08 (2H, m), 7.41-7.47 (3H, m), 7.54 (1H, s), 9.01 (2H, br s). |
| 342 | 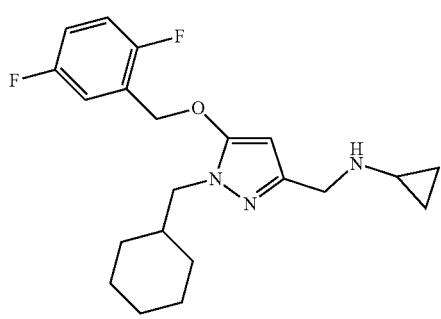 [SMILES: Fc1ccc(F)c(COc2cc(CNC3CC3)nn2CC2CCCCC2)c1] | ¹H-NMR (300 MHz, CDCl₃) δ: 0.35-0.46 (4H, m), 0.87-1.04 (2H, m), 1.09-1.30 (3H, m), 1.54-1.94 (6H, m), 2.15-2.25 (1H, m), 3.73-3.79 (4H, m), 5.09 (2H, s), 5.53 (1H, s), 6.97-7.18 (3H, m). |

-continued

| Example | Structure | Mass analysis Observed [M + 1]/ ¹H-NMR spectra/specific optical rotation |
|---|---|---|
| 344 | 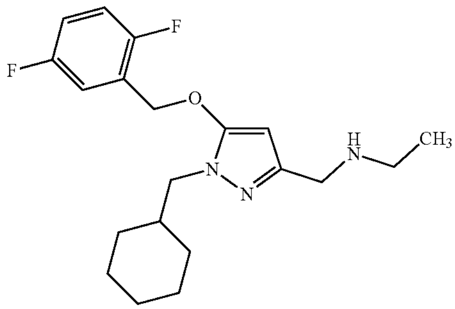 [SMILES: CCNCc1cc(OCc2cc(F)ccc2F)n(CC2CCCCC2)n1] | ¹H-NMR (300 MHz, CDCl₃) δ: 0.86-1.02 (2H, m), 1.07-1.29 (6H, m), 1.44-1.94 (6H, m), 2.70 (2H, q, J = 7.2 Hz), 3.69 (2H, s), 3.75 (2H, d, J = 7.3 Hz), 5.10 (2H, s), 5.56 (1H, s), 6.97-7.18 (3H, m). |
| 347 | 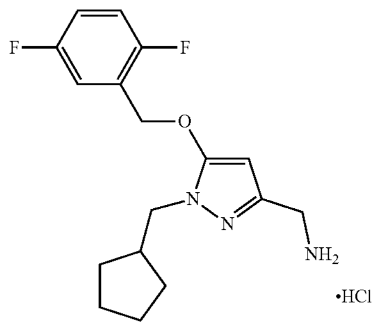 [SMILES: NCc1cc(OCc2cc(F)ccc2F)n(CC2CCCC2)n1 ; Cl] | 322.4 |
| 349 | 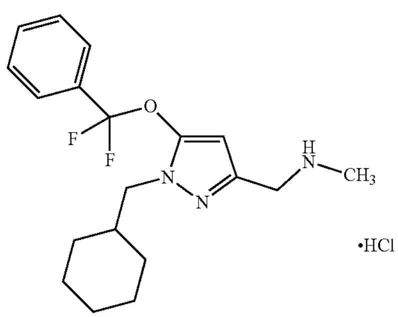 [SMILES: CNCc1cc(OC(F)(F)c2ccccc2)n(CC2CCCCC2)n1 ; Cl] | 350.4 |
| 369 | 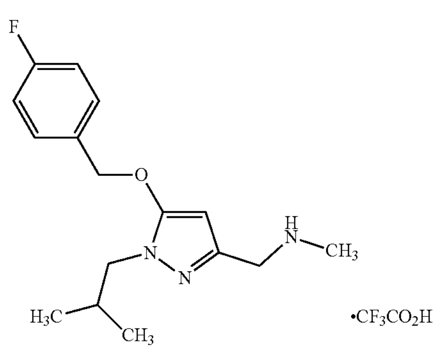 [SMILES: CNCc1cc(OCc2ccc(F)cc2)n(CC(C)C)n1 ; "·CF3CO2H"] | 292.3 |

-continued
| Example | Structure | Mass analysis Observed [M + 1]/ $^1$H-NMR spectra/specific optical rotation |
|---|---|---|
| 375 | 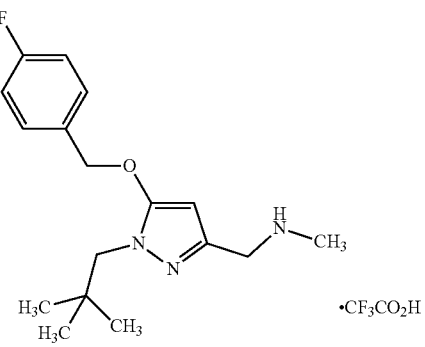 •CF$_3$CO$_2$H | 306.5 |
| 381 | 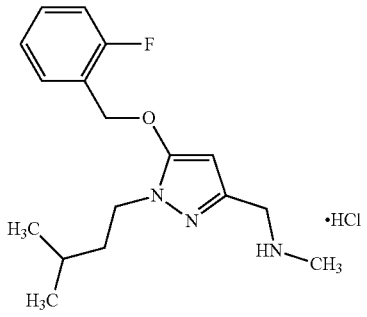 [SMILES: CNCc1cc(OCc2ccccc2F)n(CCC(C)C)n1 ; Cl] •HCl | 306.4 |
| 383 | 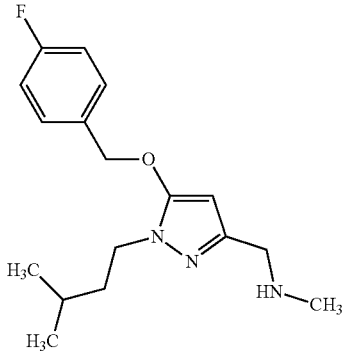 [SMILES: CNCc1cc(OCc2ccc(F)cc2)n(CCC(C)C)n1] | 306.4 |
| 446 | 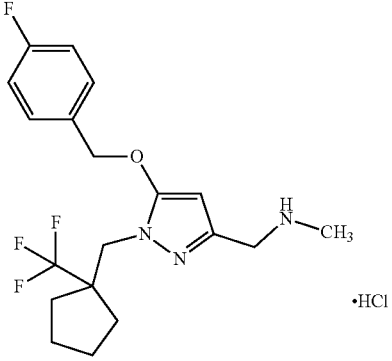 [SMILES: CNCc1cc(OCc2ccc(F)cc2)n(CC2(C(F)(F)F)CCCC2)n1 ; Cl] •HCl | 386.4 |

-continued

| Example | Structure | Mass analysis Observed [M + 1]/ ¹H-NMR spectra/specific optical rotation |
|---|---|---|
| 447 | (2,5-difluorobenzyl ether pyrazole with 1-(trifluoromethyl)cyclopentyl and N-methylaminomethyl) ·HCl | 404.6 |
| 448 | (5-chloro-2-fluorobenzyl ether pyrazole with 1-(trifluoromethyl)cyclopentyl and N-methylaminomethyl) ·HCl | 420.2 |
| 474 | (5-chloro-2-fluorobenzyl ether pyrazole with (tetrahydro-2H-pyran-2-yl)methyl** and N-methylaminomethyl) ·HCl | ¹H-NMR (300 MHz, CDCl₃) δ: 1.29 (1H, m), 1.43–1.67 (4H, m), 1.84 (1H, m), 2.62 (3H, s), 3.36 (1H, t, J = 10.8 Hz), 3.67 (1H, m), 3.88 (1H, dd, J = 14.1, 4.4 Hz), 3.97 (1H, m), 4.05 (1H, m), 4.09 (2H, s), 5.13 (2H, s), 6.11 (1H, s), 7.04 (1H, t, J = 9.0 Hz), 7.30 (1H, m), 7.47 (1H, dd, J = 6.0, 2.5 Hz), 9.78 (2H, br s). Specific optical rotation: [α] D²⁶ − 6.6 (c.1.21, CHCl₃) |
| 475 | (5-chloro-2-fluorobenzyl ether pyrazole with (tetrahydro-2H-pyran-2-yl)methyl** and N-methylaminomethyl) ·HCl | ¹H-NMR (300 MHz, CDCl₃) δ: 1.28 (1H, m), 1.41–1.65 (4H, m), 1.84 (1H, m), 2.61 (3H, s), 3.36 (1H, t, J = 11.1 Hz), 3.66 (1H, m), 3.88 (1H, dd, J = 13.9, 4.8 Hz), 3.97 (1H, m), 4.05 (1H, m), 4.09 (2H, s), 5.13 (2H, s), 6.11 (1H, s), 7.04 (1H, t, J = 9.0 Hz), 7.29 (1H, m), 7.47 (1H, dd, J = 6.1, 2.6 Hz), 9.79 (2H, br s). Specific optical rotation: [α] D²⁶ + 6.0 (c.1.14, 1 CHCl₃) |

-continued

| Example | Structure | Mass analysis Observed [M + 1]/ ¹H-NMR spectra/specific optical rotation |
|---|---|---|
| 476 | 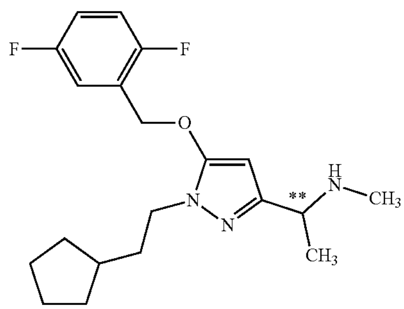 [SMILES: CNC(C)c1cc(OCc2cc(F)ccc2F)n(CCC2CCCC2)n1] | ¹H-NMR (300 MHz, CDCl₃) δ: 1.09 (2H, m), 1.35 (3H, d, J = 6.8 Hz), 1.44-1.63 (5H, m), 1.69-1.83 (5H, m), 2.37 (3H, s), 3.64 (1H, q, J = 6.7 Hz), 3.94 (2H, t, J = 7.2 Hz), 5.10 (2H, s), 5.52 (1H, s), 6.98-7.11 (2H, m), 7.15 (1H, m). Specific optical rotation: $[\alpha]D^{26}$ − 25.4 (c.1.42, CHCl₃) |
| 477 | 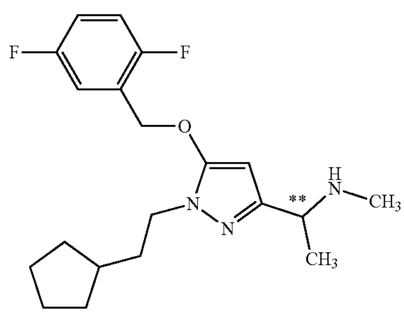 [SMILES: CNC(C)c1cc(OCc2cc(F)ccc2F)n(CCC2CCCC2)n1] | Specific optical rotation: $[\alpha]D^{26}$ + 25.0 (c.1.60, CHCl₃) |
| 481 | 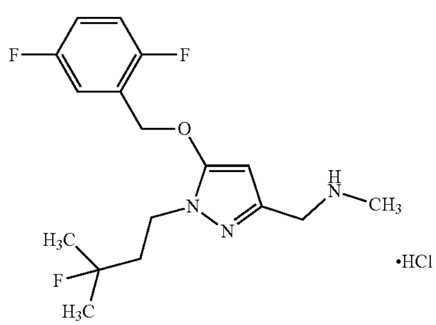 [SMILES: CNCc1cc(OCc2cc(F)ccc2F)n(CCC(C)(C)F)n1 ; Cl] | 342.3 |
| 482 | 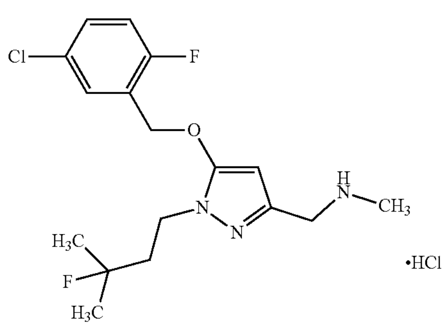 [SMILES: CNCc1cc(OCc2cc(Cl)ccc2F)n(CCC(C)(C)F)n1 ; Cl] | 358.2 |

| Example | Structure | Mass analysis Observed [M + 1]/ $^1$H-NMR spectra/specific optical rotation |
|---|---|---|
| 508 | 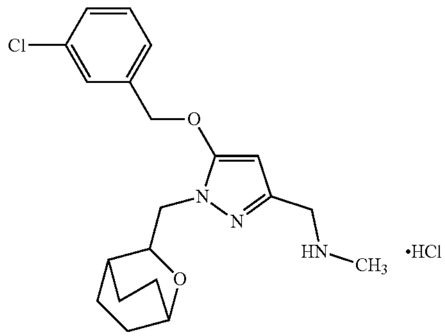 [SMILES: CNCc1cc(OCc2cccc(Cl)c2)n(CC2OC3CCC2CC3)n1 ; Cl] | 376.5 |

In the structures, the compounds wherein an assymetric carbon is shown with ** are optically active substances.

Compounds of Examples 492 to 507 were also prepared according to the methods as follows.

Reference Example 1

Ethyl 5-(benzyloxy)-1-(cyclohexylmethyl)-1H-pyrazol-3-carboxylate

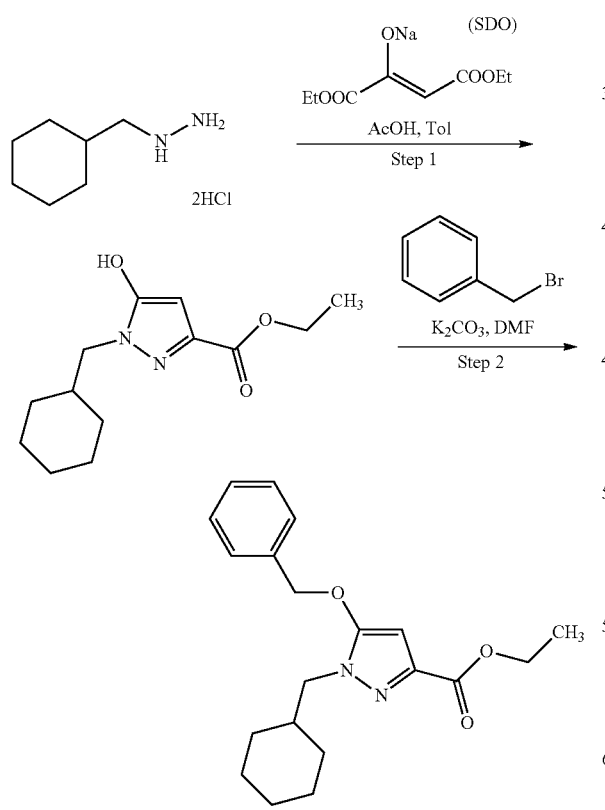

Step 1

(Cyclohexylmethyl)hydrazine hydrochloride was used for the starting material and reacted and treated according to the method of Reference Example 36 Step (i) described in Patent Literature 1 to give ethyl 1-(cyclohexylmethyl)-5-hydroxy-1H-pyrazol-3-carboxylate (2.16 g, 57%) as a solid.

$^1$H-NMR (300 MHz, CDCl$_3$) δ: 0.90-1.06 (2H, m), 1.08-1.27 (3H, m), 1.29-1.42 (3H, m), 1.51-1.77 (5H, m), 1.77-1.98 (1H, m), 3.54 (0.7H, s), 3.61 (0.7H, d, J=7.3 Hz), 3.87 (1.3H, d, J=7.5 Hz), 4.30-4.43 (2H, m), 5.96 (0.6H, s).

Step 2

Ethyl 1-(cyclohexylmethyl)-5-hydroxy-1H-pyrazol-3-carboxylate and benzyl bromide were used for the starting materials and reacted and treated according to the method of Reference Example 36 Step (ii) described in Patent Literature 1 to give the title compound (1.23 g, 90%) as an oil.

$^1$H-NMR (300 MHz, CDCl$_3$) δ: 0.85-1.03 (2H, m), 1.08-1.24 (3H, m), 1.38 (3H, t, J=7.2 Hz), 1.48-1.74 (5H, m), 1.85-1.99 (1H, m), 3.87 (2H, d, J=7.3 Hz), 4.38 (2H, q, J=7.2 Hz), 5.10 (2H, s), 6.10 (1H, s), 7.32-7.45 (5H, m).

Reference Example 2

5-(Benzyloxy)-1-(cyclohexylmethyl)-1H-pyrazol-3-carboxylic Acid

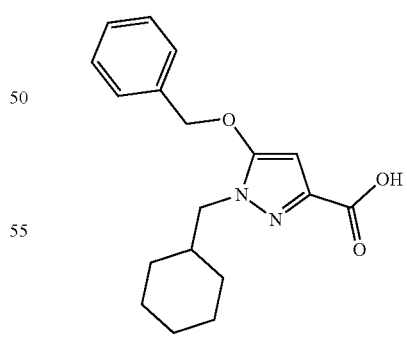

To the compound of Reference Example 1 (300 mg, 0.876 mmol) was added ethanol (4 ml). Then, thereto was added 6N aqueous solution of sodium hydroxide (1 ml). The mixture was stirred at room temperature for 1 hour and 25 minutes, and then ethanol was removed under reduced pressure. Then, the resultant was adjusted to pH 1 by addition of 2N hydrochloric acid (7 ml). The resulted aqueous layer was extracted with ethyl acetate, and then dried over MgSO$_4$ and concentrated after filtration to give the desired product (255 mg, 93%).

$^1$H-NMR (300 MHz, DMSO-D$_6$) 5: 0.78-1.01 (2H, m), 1.03-1.22 (3H, m), 1.38-1.53 (2H, m), 1.53-1.68 (3H, m), 1.69-1.83 (1H, m), 3.79 (2H, d, J=7.2 Hz), 5.21 (2H, s), 6.17 (1H, s), 7.34-7.48 (5H, m), 12.55 (1H, brs).

Reference Example 3

5-(Benzyloxy)-1-(cyclohexylmethyl)-N-($^2$H$_3$)methyl-1H-pyrazol-3-carboxamide

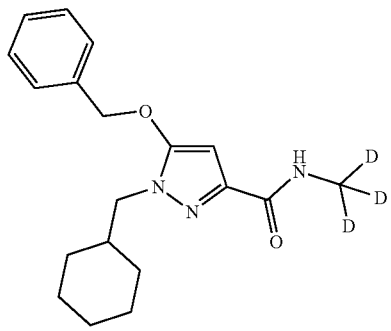 [SMILES: [2H]C([2H])([2H])NC(=O)c1cc(OCc2ccccc2)n(CC2CCCCC2)n1]

To the compound of Reference Example 2 (230 mg, 0.732 mmol) was added DMF (4 ml), followed by addition of deuterated methylamine hydrochloride (67.1 mg, 0.951 mmol), N-hydroxybenzotriazole hydrate (146 mg, 0.951 mmol), triethylamine (408 μl, 2.93 mmol), and 1-[3-(dimethylamino)propyl]-3-ethylcarbodiimide hydrochloride (210 mg, 1.10 mmol). The mixture was stirred at room temperature overnight, and then thereto was added water (50 ml). The mixture was extracted with ethyl acetate (50 ml) twice. The combined organic layers were dried over magnesium sulfate, and then solvents were removed under reduced pressure after filtration. The resulted concentrated residue was purified by silica gel column chromatography (solvent system: n-hexane-ethyl acetate) to give the desired compound (193 mg, 80%).

$^1$H-NMR (300 MHz, CDCl$_3$) δ: 0.86-1.03 (2H, m), 1.09-1.30 (3H, m), 1.51-1.75 (5H, m), 1.76-1.92 (1H, m), 3.78 (2H, d, J=7.3 Hz), 5.09 (2H, s), 6.10 (1H, s), 6.76 (1H, br s), 7.33-7.42 (5H, m).

Reference Example 4

5-(Benzyloxy)-1-(cyclohexylmethyl)-N-methyl-1H-pyrazol-3-carboxamide

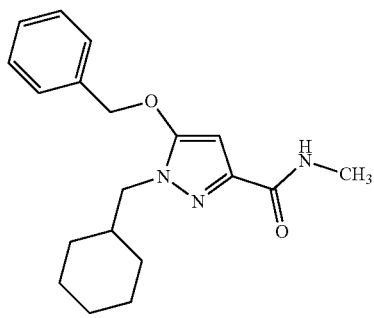 [SMILES: CNC(=O)c1cc(OCc2ccccc2)n(CC2CCCCC2)n1]

To the compound of Reference Example 1 (2.28 mg, 6.67 mmol) was added a 43% methylamine-methanol solution (13 ml). Then, the mixture was stirred at 40° C. overnight, and then solvent was removed under reduced pressure. The resulted concentrated residue was purified by silica gel column chromatography (solvent system: n-hexane-ethyl acetate) to give the desired compound (1.50 g, 69%).

$^1$H-NMR (300 MHz, CDCl$_3$) δ: 0.86-1.02 (2H, m), 1.09-1.28 (3H, m), 1.53-1.61 (2H, m), 1.63-1.75 (3H, m), 1.77-1.89 (1H, m), 2.94 (3H, d, J=5.1 Hz), 3.78 (2H, d, J=7.2 Hz), 5.09 (2H, s), 6.10 (1H, s), 6.78 (1H, brs), 7.33-7.42 (5H, m).

Example 492

1-[5-(Benzyloxy)-1-(cyclohexylmethyl)-1H-pyrazol-3-yl]-N-methyl($^2$H$_2$)methanamine

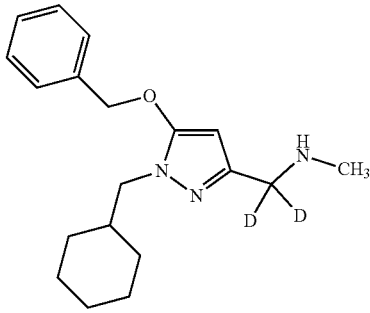 [SMILES: [2H]C([2H])(NC)c1cc(OCc2ccccc2)n(CC2CCCCC2)n1]

To deuterated lithium aluminum hydride (76.9 mg, 1.83 mmol) was added THF (1.5 ml). Then, thereto was added the compound of Reference Example 4 (200 mg, 0.611 mmol), and then the mixture was refluxed. After the reflux for 4 hours and 50 minutes, water (76 μl), 15% aqueous solution of sodium hydroxide (76 μL), and water (228 μl) were sequentially added thereto at 0° C., and then the mixture was stirred for 1 hour. Then, the mixture was filtered through Celite, followed by removal of solvents under reduced pressure. The resulted concentrated residue was purified by silica gel column chromatography (n-hexane-ethyl acetate→chloroform-methanol, solvent system) to give the desired compound (102 mg, 53%) as an oil.

$^1$H-NMR (300 MHz, CDCl$_3$) δ: 0.82-1.02 (2H, m), 1.08-1.30 (3H, m), 1.51-1.75 (5H, m), 1.77-1.90 (1H, m), 2.46 (3H, s), 3.75 (2H, d, J=7.3 Hz), 5.05 (2H, s), 5.55 (1H, s), 7.31-7.43 (5H, m).

Example 493

1-[5-(Benzyloxy)-1-(cyclohexylmethyl)-1H-pyrazol-3-yl]-N-($^2$H$_3$)methyl($^2$H$_2$) methanamine

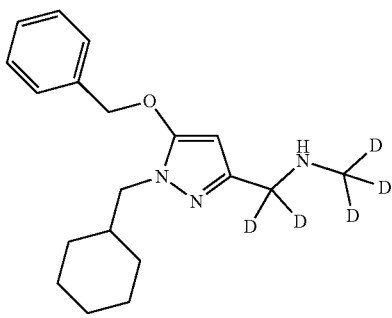 [SMILES: [2H]C([2H])([2H])NC([2H])([2H])c1cc(OCc2ccccc2)n(CC2CCCCC2)n1]

To the compound of Reference Example 3 (80 mg, 0.242 mmol) was added THF (1.0 ml), followed by addition of deuterated lithium aluminum hydride (30.5 mg, 0.726 mmol). Then, the mixture was heated to 70° C. The mixture was stirred at 70° C. overnight, and then thereto were added sequentially water (30.1 μl), 15% aqueous solution of sodium hydroxide (30.1 μL), and water (90.4 μl) at 0° C. The mixture was stirred at room temperature for 30 minutes, and then solvents were removed under reduced pressure after filtration through Celite. The resulted concentrated residue was purified by silica gel column chromatography (n-hexane-ethyl acetate→chloroform-methanol, solvent system) to give the desired compound (15.7 mg, 20%) as an oil.

$^1$H-NMR (300 MHz, CDCl$_3$) δ: 0.76-1.02 (2H, m), 1.04-1.31 (3H, m), 1.51-1.75 (5H, m), 1.76-1.92 (1H, m), 3.75 (2H, d, J=7.3 Hz), 5.06 (2H, s), 5.69 (1H, s), 7.31-7.44 (5H, m).

Example 494

1-[5-(Benzyloxy)-1-(cyclohexylmethyl)-1H-pyrazol-3-yl]-N-($^2$H$_3$)methylmethanamine

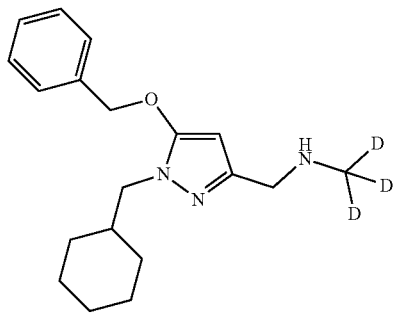 [SMILES: [2H]C([2H])([2H])NCc1cc(OCc2ccccc2)n(CC2CCCCC2)n1]

To the compound of Reference Example 3 (80 mg, 0.242 mmol) was added THF (1.0 ml), followed by addition of lithium aluminum hydride (27.6 mg, 0.726 mmol). Then, the mixture was heated to 70° C. The mixture was stirred at 70° C. overnight, and then thereto were added sequentially water (54.5 μl), 15% aqueous solution of sodium hydroxide (54.4 μL), and water (103 μl) at 0° C. The mixture was stirred at room temperature for 30 minutes, and then solvents were removed under reduced pressure after filtration through Celite. The resulted concentrated residue was purified by silica gel column chromatography (n-hexane-ethyl acetate→chloroform-methanol, solvent system) to give the desired compound (17.9 mg, 23%) as an oil.

$^1$H-NMR (400 MHz, CDCl$_3$) δ: 0.87-1.01 (2H, m), 1.08-1.28 (3H, m), 1.51-1.73 (5H, m), 1.77-1.90 (1H, m), 3.73 (2H, s), 3.75 (2H, d, J=7.3 Hz), 5.06 (2H, s), 5.62 (1H, s), 7.32-7.42 (5H, m).

Example 495

1-[1-(Cyclopentylmethyl)-5-{[(2,5-difluorophenyl)($^2$H$_2$)methyl]oxy}-1H-pyrazol-3-yl]-N-methylmethanamine Hydrochloride

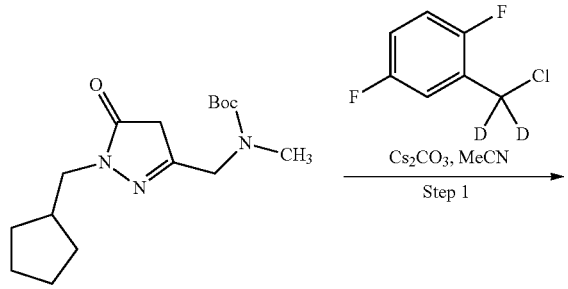

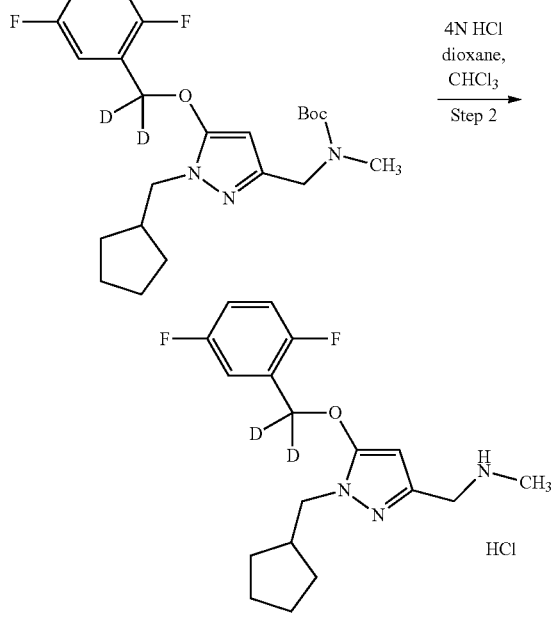

The compound of Reference Example 1 described in Patent Literature 1 (i.e., tert-butyl{[1-(cyclopentylmethyl)-5-oxo-4,5-dihydro-1H-pyrazol-3-yl]methyl}methylcarbamate) and (2,5-difluorophenyl) ($^2$H$_2$) methyl chloride were used for the starting materials and reacted and treated according to the method of Example 198 Step (iii) to (iv) described in Patent Literature 1 to give the title compound (87 mg, 72%).

$^1$H-NMR (DMSO-D$_6$) δ: 1.16-1.22 (2H, m), 1.44-1.55 (6H, m), 2.26-2.29 (1H, m), 2.50 (3H, brt), 3.78 (2H, d, J=7.6 Hz), 3.95-3.96 (2H, m), 5.95 (1H, s), 7.28-7.46 (3H, m), 9.04 (2H, brs).

Examples 496 to 498

The compound of Reference Example 1(i.e., tert-butyl{[1-(cyclopentylmethyl)-5-oxo-4,5-dihydro-1H-pyrazol-3-yl]methyl}methylcarbamate) or the compound of Reference Example 4 (i.e., tert-butyl{[1-(cyclohexylmethyl)-5-oxo-4,5-dihydro-1H-pyrazol-3-yl]methyl}methylcarbamate) as described in Patent Literature 1 and the corresponding benzyl chloride were used for the starting materials to provide the compounds of Examples 496 to 498 in a similar manner to Example 495.

Example 496

1-[5-{[(5-Chloro-2-fluorophenyl) ($^2$H$_2$)methyl]oxy}-1-(cyclopentylmethyl)-1H-pyrazol-3-yl]-N-methyl-methanamine Hydrochloride

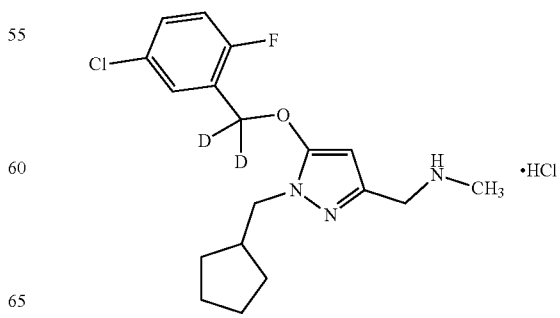

¹H-NMR (DMSO-D₆) δ: 1.17-1.20 (2H, m), 1.47-1.52 (6H, m), 2.24-2.27 (1H, m), 2.51 (3H, brs), 3.78 (2H, d, J=7.6 Hz), 3.96 (2H, s), 5.94 (1H, s), 7.35 (1H, t, J=9.3 Hz), 7.51-7.54 (1H, m), 7.65 (1H, dd, J=6.1, 2.4 Hz), 8.99 (2H, s).

Example 497

1-[1-(Cyclohexylmethyl)-5-{[(2,5-difluorophenyl) (²H₂)methyl]oxy}-1H-pyrazol-3-yl]-N-methylmethanamine Hydrochloride

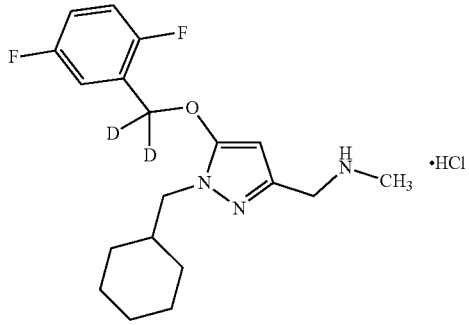 [SMILES: [2H]C([2H])(Oc1cc(CNC)nn1CC1CCCCC1)c1cc(F)ccc1F ; Cl]

¹H-NMR (DMSO-D₆) δ: 0.86-0.91 (2H, m), 1.09-1.11 (3H, m), 1.43-1.73 (6H, m), 2.50 (3H, brt), 3.70 (2H, d, J=7.1 Hz), 3.95 (2H, t, J=4.9 Hz), 5.96 (1H, s), 7.27-7.45 (3H, m)), 9.07 (2H, brs).

Example 498

1-[5-{[(5-Chloro-2-fluorophenyl) (²H₂)methyl]oxy}-1-(cyclohexylmethyl)-1H-pyrazol-3-yl]-N-methyl-methanamine Hydrochloride

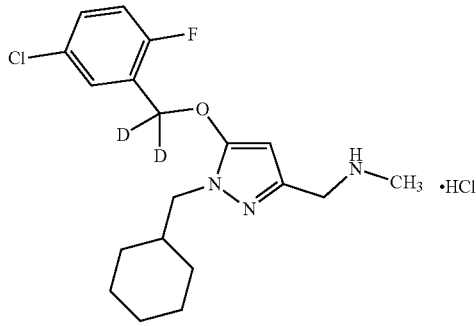 [SMILES: [2H]C([2H])(Oc1cc(CNC)nn1CC1CCCCC1)c1cc(Cl)ccc1F ; Cl]

¹H-NMR (DMSO-D₆) δ: 0.84-0.93 (2H, m), 1.07-1.12 (3H, m), 1.43-1.46 (2H, m), 1.57-1.73 (4H, m), 2.50 (3H, br), 3.70 (2H, d, J=7.1 Hz), 3.94-3.96 (2H, m), 5.95 (1H, s), 7.35 (1H, t, J=9.3 Hz), 7.51-7.53 (1H, m), 7.63-7.65 (1H, m), 9.05 (2H, s).

Example 499

1-[5-{[(2,5-Difluorophenyl) (²H₂)methyl]oxy}-1-(3,3-dimethylbutyl)-1H-pyrazol-3-yl]-N-methyl(²H₂) methanamine Citrate

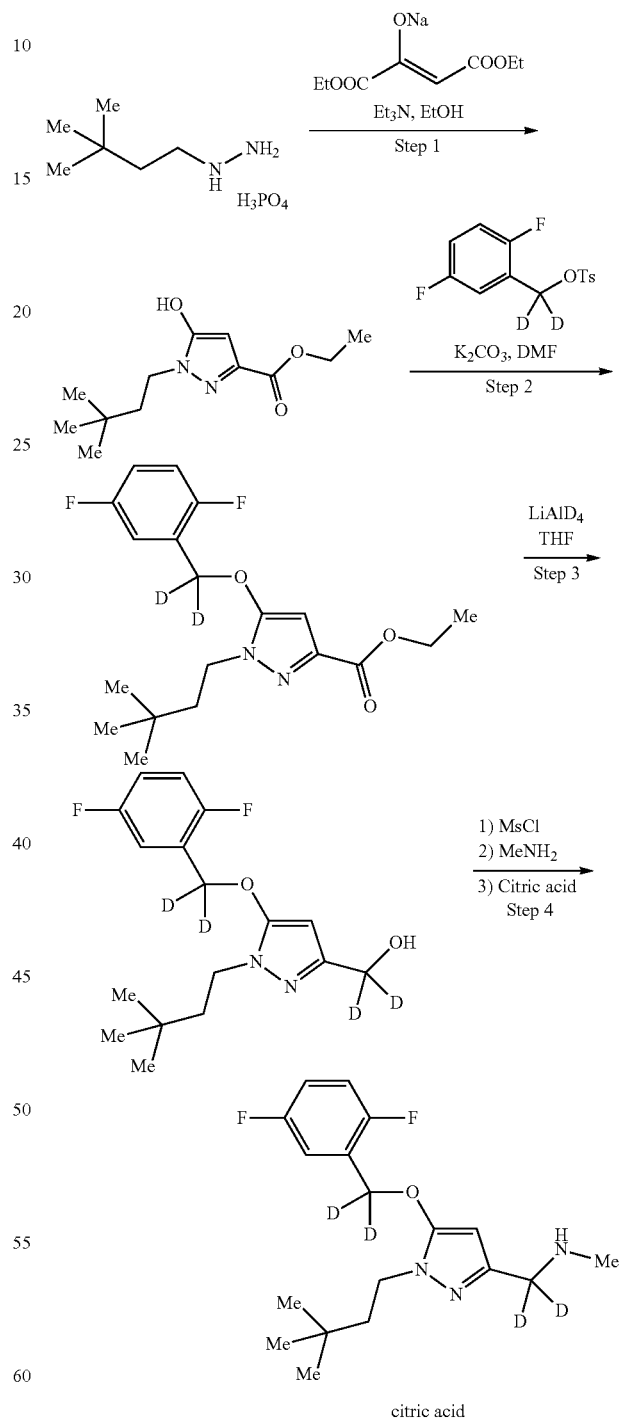

Step 1

(3,3-Dimethylbutyl)hydrazine phosphate was used for the starting material and reacted and treated according to the method of Reference Example 87 described in Patent Literature 1 to give ethyl 1-(3,3-dimethylbutyl)-5-hydroxy-1H-pyrazol-3-carboxylate (11.89 g, 71%).

Step 2

Ethyl 1-(3,3-dimethylbutyl)-5-hydroxy-1H-pyrazol-3-carboxylate and (2,5-difluorophenyl) ($^2H_2$)methyl 4-methylbenzenesulfonate were used for the starting materials and reacted and treated according to the method of Example 489 step (i) described in Patent Literature 1 to give ethyl 5-{[2,5-difluorophenyl) ($^2H_2$)methyl]oxy}-1-(3,3-dimethylbutyl)-1H-pyrazol-3-carboxylate (17.19 g, 95%).

Step 3

Ethyl 5-{[2,5-difluorophenyl) ($^2H_2$)methyl]oxy}-1-(3,3-dimethylbutyl)-1H-pyrazol-3-carboxylate and deuterated lithium aluminum hydride were used for the starting material and a reducing agent, respectively, and reacted and treated according to the method of Example 489 step (ii) described in Patent Literature 1 to give [5-{[2,5-difluorophenyl) ($^2H_2$)methyl]oxy}-1-(3,3-dimethylbutyl)-1H-pyrazol-3-yl] ($^2H_2$)methanol (9.99 g, 97%).

Step 4

[5-{[2,5-Difluorophenyl) ($^2H_2$)methyl]oxy}-1-(3,3-dimethylbutyl)-1H-pyrazol-3-yl]($^2H_2$)methanol was used for the starting material and reacted and treated according to the method of Example 489 step (iii) described in Patent Literature 1 to give 1-[5-{[(2,5-difluorophenyl) ($^2H_2$)methyl]oxy}-1-(3,3-dimethylbutyl)-1H-pyrazol-3-yl]-N-methyl($^2H_2$)methanamine, followed by reaction and treatment according to the method of Example 491 described in Patent Literature 1 to give 1-[5-{[(2,5-difluorophenyl) ($^2H_2$)methyl]oxy}-1-(3,3-dimethylbutyl)-1H-pyrazol-3-yl]-N-methyl($^2H_2$)methanamine citrate (4.29 g, 50%).

$^1$H-NMR (CD$_3$OD) δ: 0.92 (9H, s), 1.59-1.65 (2H, m), 2.68 (3H, s), 2.70-2.85 (4H, m), 3.96-4.02 (2H, m), 5.93 (1H, s), 7.13-7.31 (3H, m).

The following deuterated compounds may be prepared with corresponding starting materials according to the methods of Examples 492 to 499:

1-[5-{[(2,5-difluorophenyl) ($^2H_2$)methyl]oxy}-1-(3,3-dimethylbutyl)-1H-pyrazol-3-yl]-N-methylmethanamine;
1-{5-[(2,5-difluorobenzyl)oxy]-1-(3,3-dimethylbutyl)-1H-pyrazol-3-yl}-N-methyl($^2H_2$)methanamine;
1-{5-[(2,5-difluorobenzyl)oxy]-1-(3,3-dimethylbutyl)-1H-pyrazol-3-yl}-N-($^2H_3$)methyl($^2H_2$)methanamine; and
1-{5-[(2,5-difluorobenzyl)oxy]-1-(3,3-dimethylbutyl)-1H-pyrazol-3-yl}-N-($^2H_3$)methylmethanamine.

Example 500

1-{5-[(2,5-Difluorobenzyl)oxy]-1-(3,3-dimethylbutyl)-1H-pyrazol-3-yl}-N-methylmethanamine Monophosphate

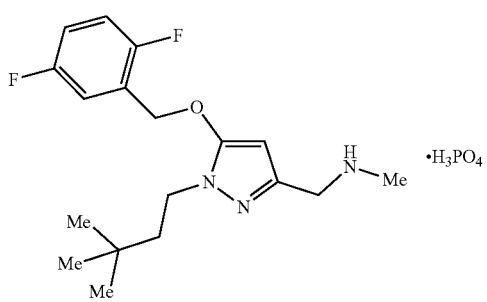 [SMILES: CNCc1cc(OCc2cc(F)ccc2F)n(CCC(C)(C)C)n1 ; "·H3PO4"]

To the compound of Example 266 described in Patent Literature 1 (i.e., 1-{5-[(2,5-difluorobenzyl)oxy]-1-(3,3-dimethylbutyl)-1H-pyrazol-3-yl}-N-methylmethanamine hydrochloride) (0.99 g, 2.65 mmol) was added chloroform (60 mL), followed by addition of 5% aqueous solution of potassium carbonate (20 mL) at 0° C., and the mixture was stirred at 0° C. for 10 minutes. Then, the organic layer was separated, and the aqueous layer was extracted with chloroform (20 mL). Combined organic layers were washed with water (20 ml), and then dried over anhydrous sodium sulfate and filtered. To the resulted chloroform solution was added a mixed solution of phosphoric acid (75%, 383 mg, 2.93 mmol) in 2-propanol (13 mL) under a water bath, and then the mixture was stirred at room temperature for 30 minutes. Then, solvents were removed under reduced pressure. To the residue was added 2-propanol (11 mL), and the mixture was warmed to 75° C. and then stirred at 65° C. for 60 minutes and cooled slowly to room temperature. The mixture was stirred at room temperature overnight, and then stirred at 0° C. for 2 hours. The resulted precipitate was filtered and dried under reduced pressure to give the title compound (998 mg, 86%) as a solid.

$^1$H-NMR (DMSO-D$_6$) δ: 0.85 (9H, s), 1.49-1.53 (2H, m), 2.35 (3H, s), 3.68 (2H, s), 3.82-3.86 (2H, m), 5.18 (2H, s), 5.87 (1H, s), 7.26-7.45 (3H, m).

Example 501

1-{5-[(2,5-Difluorobenzyl)oxy]-1-(3,3-dimethylbutyl)-1H-pyrazol-3-yl}-N-methylmethanamine

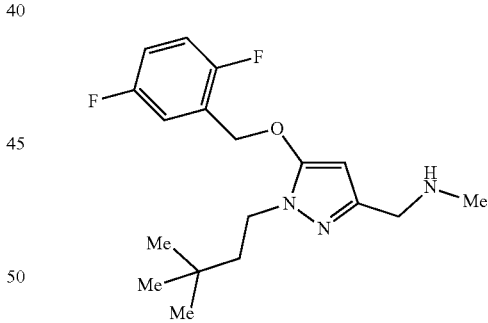

To the compound of Example 500 (5.0 g, 11.48 mmol) was added toluene (80 mL), followed by addition of 20% aqueous solution of potassium carbonate (40 mL) at room temperature, and the mixture was stirred at room temperature for 60 minutes. Then, the organic layer was separated and washed with water, and then solvents were removed under reduced pressure. The resulted concentrated residue was purified by silica gel column chromatography (chloroform-methanol solvent system) to give the title compound (3.70 g, 95%) as an oil.

$^1$H-NMR (DMSO-D$_6$) δ: 0.84 (9H, s), 1.49 (2H, t, J=8.0 Hz), 2.21 (3H, s), 3.41 (2H, s), 3.80 (2H, t, J=8.1 Hz), 5.15 (2H, s), 5.69 (1H, s), 7.23-7.44 (3H, m).

Example 502

1-{5-[(2,5-Difluorobenzyl)oxy]-1-(3,3-dimethylbutyl)-1H-pyrazol-3-yl}-N-methylmethanamine Monocitrate

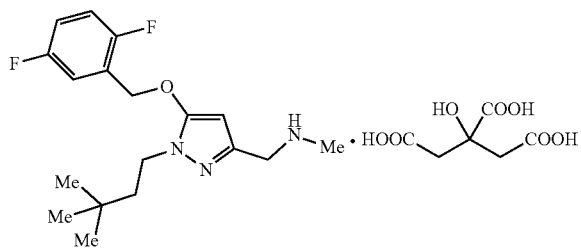 [SMILES: CNCc1cc(OCc2cc(F)ccc2F)n(CCC(C)(C)C)n1 ; O=C(O)CC(O)(CC(=O)O)C(=O)O]

To the compound of Example 501 (300 mg, 0.889 mmol) was added 2-propanol (1.5 mL), followed by addition of anhydrous citric acid (171 mg, 0.890 mmol), and the mixture was heated to 85° C. Then, thereto was added 2-propanol (1.5 mL), and the mixture was maintained at 75° C. Then, thereto was added a seed crystal that was synthesized separately, and the mixture was cooled slowly to room temperature. The precipitate was filtered and dried under reduced pressure to give the title compound (439 mg, 93%) as a solid.

$^1$H-NMR (CD$_3$OD) δ: 0.92 (s, 9H), 1.60-1.65 (m, 2H), 2.68 (s, 3H), 2.77 (dd, J=33.2, 15.4 Hz, 4H), 3.97-4.01 (m, 2H), 4.06 (s, 2H), 5.24 (s, 2H), 5.92 (s, 1H), 7.13-7.30 (m, 3H).

Example 503

1-{5-[(2,5-Difluorobenzyl)oxy]-1-(3,3-dimethylbutyl)-1H-pyrazol-3-yl}-N-methylmethanamine Monosuccinate

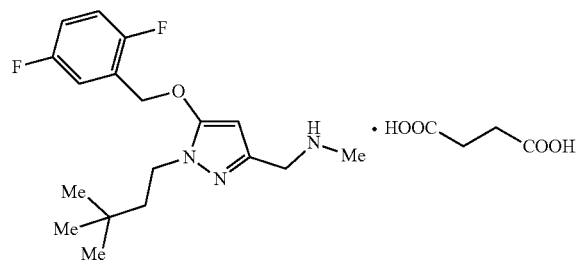 [SMILES: CNCc1cc(OCc2cc(F)ccc2F)n(CCC(C)(C)C)n1 ; O=C(O)CCC(=O)O]

The compound of Example 501 (2.68 g, 6.89 mmol) was dissolved in 2-propanol (20 mL), and then was added dropwise to a solution of succinic acid (814 mg, 6.89 mmol) in 2-propanol (20 mL). Solvents were removed under reduced pressure. To the residue was added 2-propanol (21 mL), and the mixture was warmed to 30 to 35° C. Then, thereto was added a seed crystal that was synthesized separately. Thereto was added n-hexane (11 ml), and the mixture was maintained at 30 to 35° C. for 60 minutes, and then cooled slowly to room temperature. Then, the mixture was stirred at 0° C. for 60 minutes, and then the precipitate was filtered and dried under reduced pressure to give the title compound (2.70 g, 86%) as a solid.

$^1$H-NMR (DMSO-D$_6$) δ: 0.86 (9H, s), 1.49-1.53 (2H, m), 2.29 (4H, s), 2.40 (3H, s), 3.73 (2H, s), 3.83-3.87 (2H, m), 5.19 (2H, s), 5.81 (1H, s), 7.26-7.44 (3H, m).

Example 504

1-{5-[(2,5-Difluorobenzyl)oxy]-1-(2,2-dimethylpropyl)-1H-pyrazol-3-yl}-N-methylmethanamine monophosphate dihydrate

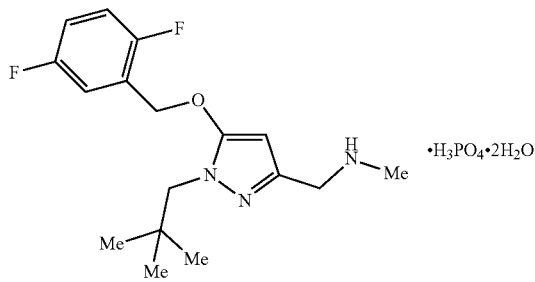 [SMILES: CNCc1cc(OCc2cc(F)ccc2F)n(CC(C)(C)C)n1 ; "·H3PO4·2H2O"]

The compound of Example 258 described in Patent Literature 1 (i.e., 1-{5-[(2,5-difluorobenzyl)oxy]-1-(2,2-dimethylpropyl)-1H-pyrazol-3-yl}-N-methylmethanamine hydrochloride) was reacted and treated according to the method of Example 501 to give 1-{5-[(2,5-difluorobenzyl)oxy]-1-(2,2-dimethylpropyl)-1H-pyrazol-3-yl}-N-methylmethanamine, which was then reacted and treated according to the method of Example 500 to give the title compound (170.80 g, 48%).

$^1$H-NMR (DMSO-d$_6$) δ: 0.85 (9H, s), 2.37 (3H, s), 3.63 (2H, s), 3.76 (2H, s), 5.15 (2H, s), 5.98 (1H, s), 7.23-7.39 (2H, m), 7.39-7.50 (1H, m).

Example 505

1-{5-[(2,5-Difluorobenzyl)oxy]-1-(3,3-dimethylbutyl)-1H-pyrazol-3-yl}methanamine Monophosphate

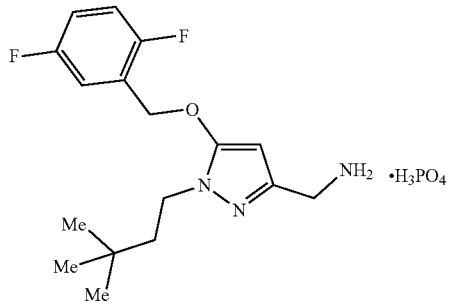

{5-[(2,5-Difluorobenzyl)oxy]-1-(3,3-dimethylbutyl)-1H-pyrazol-3-yl}methanol was used for the starting material with phosphoric acid instead of 4 mol/L hydrogen chloride-1,4-dioxane solution according to the method of Example 347 described in Patent Literature 1 to give the title compound (273 mg, 18%).

Obs MS[M+1]: 324.6

Example 506

1-{5-[(2,5-Difluorobenzyl)oxy]-1-(3,3-dimethylbutyl)-1H-pyrazol-3-yl}methanamine monocitrate The reaction and treatment according to the method of Example 502 gave the title compound (5.55 g, 93%).

$^1$H-NMR (CD$_3$OD) δ: 0.93 (s, 9H), 1.59-1.65 (m, 2H), 2.70-2.84 (m, 4H), 3.96-4.01 (m, 4H), 5.23 (s, 2H), 5.87 (s, 1H), 7.14-7.30 (m, 3H).

Using corresponding starting materials according to the methods of Examples 505 to 506 can give the following compound.

1-{5-[(2,5-Difluorobenzyl)oxy]-1-(2-methylpropyl)-1H-pyrazol-3-yl}methanamine

Example 507

1-[5-{[(2,5-Difluorophenyl) ($^2$H$_2$)methyl]oxy}-1-(3,3-dimethylbutyl)-1H-pyrazol-3-yl] ($^2$H$_2$)methanamine Monocitrate The compound obtained in Example 499 step 3 was reacted and treated with corresponding starting materials according to the method of Example 485 described in Patent Literature 1 to give 1-[5-{[(2,5-difluorophenyl) ($^2$H$_2$)methyl]oxy}-1-(3,3-dimethylbutyl)-1H-pyrazol-3-yl]($^2$H$_2$)methanamine, followed by reaction and treatment according to Example 502, to give the title compound (6.04 g, 70%).

$^1$H-NMR (CD$_3$OD) δ: 0.92 (s, 9H), 1.59-1.64 (m, 2H), 2.70-2.84 (m, 4H), 3.95-4.01 (m, 2H), 5.88 (s, 1H), 7.13-7.30 (m, 3H).

Using corresponding starting materials according to the method of Example 507 can give the following compounds.
1-[1-(Cyclopentylmethyl)-5-{[(2,5-difluorophenyl) ($^2$H$_2$)methyl]oxy}-1H-pyrazol-3-yl] ($^2$H$_2$)methanamine monocitrate;
1-[1-(3-Methylbutyl)-5-{[(2,4,5-trifluorophenyl) ($^2$H$_2$)methyl]oxy}-1H-pyrazol-3-yl] ($^2$H$_2$)methanamine monocitrate;
1-[5-{[(2,5-Difluorophenyl) ($^2$H$_2$)methyl]oxy}-1-(2-methylpropyl)-1H-pyrazol-3-yl]($^2$H$_2$)methanamine monocitrate.
1-{1-(Cyclohexylmethyl)-5-[(2,4,5-trifluorobenzyl)oxy]-1H-pyrazol-3-yl}-N-methylmethanamine can be prepared in a similar manner to Examples 20 to 40 described in Patent Literature 1.
1-{1-(4-Fluorobenzyl)-5-[(2,4,5-trifluorobenzyl)oxy]-1H-pyrazol-3-yl}-N-methylmethanamine can be prepared in a similar manner to Example 198 described in Patent Literature 1.
1-{5-[(2,5-Difluorobenzyl)oxy]-1-(4-methoxybenzyl)-1H-pyrazol-3-yl}-N-methylmethanamine can be prepared in a similar manner to Example 198 described in Patent Literature 1.

Test 1: In Vitro Receptor Affinity Evaluation
<Methods>
(1) Human Serotonin 5-HT$_{2A}$ Receptor Binding Test A 5-HT$_{2A}$ receptor binding test was performed as follows to determine the human 5-HT$_{2A}$ receptor binding activity of [$^3$H]-ketanserin.

A solution containing 50 μL of [$^3$H]-ketanserin (the final concentration: 1 nM), 2 μL of a solution of a test compound in DMSO or a solvent (DMSO), and 148 μL of human 5-HT$_{2A}$ receptor-expressed CHO cell membrane sample was reacted in a 50 mmol/L Tris-HCl buffer (pH=7.6), and then was let stand at 37° C. for 15 minutes. Then, the resultant was added promptly to a glass fiber filter plate (Multiscreen FB, Millipore) coated with 0.05% Brij 35 and filtered under reduced pressure. The filtered substance on the glass fiber filter was washed with 200 μL of ice-cooled 50 mmol/L Tris-HCl (pH=7.6) twice and repeated to be filtered under reduced pressure, followed by transfer to a vial containing 2 mL of Ecoscint A (National Diagnostics). The radioactivity of the filtered substance remained on the glass fiber filter was measured by liquid scintillation counter. The radioactivity value measured by liquid scintillation counter was deemed to be a receptor binding activity, and the binding inhibition was calculated from the total binding (TB), non-specific binding (NSB), and specific binding (SB) of a test compound according to the following equations.

Total binding (TB)=Radioactivity of the solvent-added group

Non-specific binding (NSB)=Radioactivity of the MDL-100907 solution-added group

Specific binding (SB)=Radioactivity of the test compound solution-added group−NSB Binding inhibition (%)=SB/(TB−NSB)×100

Non-specific binding was measured in the presence of 10 μmol/L of MDL-100907, and [$^3$H]-ketanserin binding inhibition (%) was calculated in each test concentration of a test compound.

Based on the calculated binding inhibition (%), the IC$_{50}$ value was calculated according to Hill analysis (Hill A. V., J. Physiol., 40, 190-200 (1910)), and the binding inhibition constant (Ki) was calculated from the following equation:

Binding inhibition constant $(Ki)=IC_{50}/(1+S/Kd)$

S refers to the concentration of [$^3$H]-ketanserin added. The Kd value refers to the binding dissociation constant of [$^3$H]-ketanserin. The value (0.63 nmol/L) calculated from a saturated binding test conducted separately with the same cell membrane sample was used. The lower the 5-HT$_{2A}$ binding inhibition constant Ki is, the stronger the human serotonin 5-HT$_{2A}$ receptor inhibitory action is. The results are shown in Table 1.

(2) Human Serotonin 5-HT$_{2C}$ Receptor Binding Test

The human 5-HT$_{2C}$ receptor binding activity of [$^3$H]-mesulergine was determined as follows.

A solution containing 50 μL of [$^3$H]-mesulergine (GE Healthcare) diluted with 50 mmol/L Tris-HCl (pH=7.4) (the final concentration: about 2 nM), 149 μL of h-5-HT$_{2C}$/CHO cell membrane sample (20 μg/well for the amount of protein), and 1 μL of a solution of a test compound dissolved in DMSO or a solvent (DMSO) was reacted at 37° C. for 30 minutes, and then filtered promptly by aspiration under lower pressure with a glass fiber filter coated with a 1% aqueous solution of bovine serum albumin. The filtered substance on the glass fiber filter was washed with 250 μL of 50 mmol/L Tris-HCl (pH=7.4) twice, and then transferred to an ACS-II (Amersham) 4-mL-glass vial. The radioactivity of the filtered substance remained on the filter was measured by liquid scintillation counter. The radioactivity value measured by liquid scintillation counter was deemed to be a receptor binding activity, and the binding inhibition was calculated from the total binding (TB), non-specific binding (NSB), and specific binding (SB) of a test compound according to the following equations.

Total binding (TB)=Radioactivity of the solvent-added group

Non-specific binding (NSB)=Radioactivity of the SB206553 solution-added group

Specific binding (SB)=Radioactivity of the test compound solution-added group−NSB Binding inhibition (%)=SB/(TB−NSB)×100

Non-specific binding of [$^3$H]-mesulergine was deemed to be the binding amount in the presence of 10 μmol/L of SB206553 (Sigma Aldrich), and [$^3$H]-mesulergine binding inhibition (%) was calculated in each test concentration of a test compound.

Based on the calculated binding inhibition (%), the IC$_{50}$ value was calculated according to Hill analysis (Hill A. V., J. Physiol., 40, 190-200 (1910)), and the binding inhibition constant (Ki) was calculated from the following equation:

Binding inhibition constant $(Ki)=IC_{50}/(1+S/Kd)$

S refers to the concentration of [$^3$H]-mesulergine added. The Kd value refers to the binding dissociation constant of [$^3$H]-mesulergine. The value (1.34 nmol/L) calculated from a saturated binding test conducted separately with the same cell membrane sample was used. The lower the 5-HT$_{2C}$ binding inhibition constant Ki is, the higher the affinity for human serotonin 5-HT$_{2C}$ receptor is. The results are shown in Table 1.

(3) Human Serotonin Transporter (SERT) Binding Test

The SERT binding activity of [$^3$H]-citalopram was determined according to the method of Owens et al. (Owens M. J. et al., J. Pharm. Exp. Ther., 283, 1305-1322 (1997)).

Specifically, a solution containing 50 μL of [$^3$H]-citalopram (GE Healthcare) diluted with SERT buffer (50 mmol/L Tris-HCl (pH=7.4) containing 120 mmol/L NaCl and 5 mmol/L KCl) (the final concentration: about 2 nmol/L), 149 μL of h-SERT/CHO cell membrane sample (40 μg/well for the amount of protein), and 1 μL of a solution of a test compound in DMSO or a solvent (DMSO) was reacted at room temperature for 60 minutes, and then filtered promptly by aspiration under lower pressure with a glass fiber filter coated with a 0.05% aqueous polyethyleneimine solution. The filtered substance on the glass fiber filter was washed with 250 μL of SERT buffer twice, and then transferred to an ACS-II (Amersham) 4-mL-glass vial. The radioactivity of the filtered substance remained on the filter was measured by liquid scintillation counter. The radioactivity value measured by liquid scintillation counter was deemed to be a receptor binding activity, and the binding inhibition was calculated from the total binding (TB), non-specific binding (NSB), and specific binding (SB) of a test compound according to the following equations.

Total binding (TB)=Radioactivity of a solvent-added group

Non-specific binding (NSB)=Radioactivity of the clomipramine solution-added group Specific binding (SB)=Radioactivity of the test compound solution-added group−NSB Binding inhibition (%)=SB/(TB−NSB)×100

Non-specific binding of [$^3$H]-citalopram was deemed to be the binding amount in the presence of 1 μmol/L of clomipramine (Sigma Aldrich), and [$^3$H]-citalopram binding inhibition (%) was calculated in each test concentration of a test compound.

Based on the calculated binding inhibition (%), the IC$_{50}$ value was calculated according to Hill analysis (Hill A. V., J. Physiol., 40, 190-200 (1910)), and the binding inhibition constant (Ki) was calculated from the following equation:

Binding inhibition constant $(Ki)=IC_{50}/(1+S/Kd)$

S refers to the concentration of [$^3$H]-citalopram added. The Kd value refers to the binding dissociation constant of [$^3$H]-citalopram. The value (2.83 nmol/L) calculated from a saturated binding test conducted separately with the same cell membrane sample was used. The lower the h-SERT binding inhibition constant Ki is, the stronger the human serotonin reuptake inhibitory action is. The results are shown in Table 1.

TABLE 1

| Example | 5-HT$_{2A}$ receptor binding inhibition constant Ki (nmol/L) | 5-HT$_{2C}$ receptor binding inhibition constant Ki (nmol/L) | h-SERT binding inhibition constant Ki (nmol/L) |
| --- | --- | --- | --- |
| 1 | 5.5 | 26 | 4.9 |
| 5 | 5.9 | 4.4 | 1.5 |
| 20 | 0.65 | 9.0 | 1.6 |
| 30 | 0.52 | 4.8 | 1.5 |
| 31 | 1.4 | 5.2 | 0.92 |
| 33 | 0.5 | 2.9 | 0.34 |
| 34 | 0.64 | 1.5 | 2.4 |
| 37 | 2.1 | 9.2 | 0.89 |
| 38 | 3.2 | 6.2 | 2.4 |
| 108 | 4.8 | 18 | 1.9 |
| 115 | 1.0 | 5.4 | 1.5 |
| 117 | 0.76 | 3.8 | 0.5 |
| 118 | 0.73 | 2.1 | 2.0 |
| 124 | 1.7 | 16 | 0.71 |
| 127 | 1.6 | 7.0 | 1.3 |
| 131 | 3 | 10 | 3.7 |
| 137 | 1.3 | 7.9 | 6.6 |
| 138 | 11 | 9.1 | 1.8 |
| 144 | 0.2 | 2.2 | 8.3 |
| 147 | 2.2 | 4.3 | 0.61 |
| 148 | 1.8 | 1.9 | 4.6 |
| 162 | 2.7 | 14 | 7.8 |
| 218 | 1.2 | 10 | 9.7 |
| 219 | 1.3 | 10 | 1.6 |
| 224 | 1.2 | 6.6 | 1.5 |
| 230 | 2.7 | 4.9 | 2.3 |
| 242 | 6.5 | 34 | 0.52 |
| 256 | 4.5 | 12 | 1.6 |
| 258 | 7.5 | 16 | 0.66 |
| 259 | 7.5 | 6.2 | 2.4 |
| 263 | 0.52 | 5.8 | 1.1 |
| 266 | 0.65 | 4.5 | 0.69 |
| 269 | 1.5 | 6.7 | 0.59 |
| 275 | 5.9 | 11 | 22 |
| 280 | 1.3 | 9.7 | 1.9 |
| 283 | 1.3 | 6.3 | 1.1 |
| 284 | 1.8 | 7.9 | 5.7 |
| 286 | 2.4 | 6.6 | 5.5 |
| 288 | 5.2 | 19 | 0.86 |
| 291 | 2.5 | 4.1 | 1.2 |
| 292 | 1.2 | 3.8 | 0.96 |
| 293 | 1.1 | 6.4 | 0.67 |
| 295 | 0.74 | 2.2 | 0.95 |
| 296 | 2.1 | 6.2 | 0.91 |
| 298 | 3.3 | 6.8 | 0.56 |
| 299 | 5.6 | 6.8 | 1.4 |
| 300 | 0.57 | 3.3 | 1.8 |
| 301 | 0.88 | 4.6 | 1.3 |
| 302 | 0.94 | 5.5 | 1.4 |
| 303 | 1.8 | 4.7 | 0.46 |
| 304 | 1.4 | 2.0 | 1.3 |
| 305 | 2.5 | 3.7 | 2.0 |
| 315 | 0.6 | 3.6 | 11 |
| 330 | 2.8 | 17 | 0.96 |
| 331 | 2.8 | 5.9 | 1.3 |
| 341 | 4.9 | 12 | 23 |
| 342 | 4.9 | 14 | 8.5 |
| 344 | 3.4 | 6.7 | 33 |
| 347 | 12 | 31 | 13 |
| 349 | 6.0 | 18 | 3.0 |
| 351 | 15 | 43 | 0.98 |
| 492 | 2.9 | 6.8 | 1.4 |

TABLE 1-continued

| Example | 5-HT$_{2A}$ receptor binding inhibition constant Ki (nmol/L) | 5-HT$_{2C}$ receptor binding inhibition constant Ki (nmol/L) | h-SERT binding inhibition constant Ki (nmol/L) |
| --- | --- | --- | --- |
| 493 | 2.3 | 7.2 | 1.1 |
| 494 | 3.6 | 7.1 | 1.1 |
| 495 | 2 | 2.5 | 0.24 |
| 496 | 1.7 | 1.1 | 2.0 |
| 497 | 2.4 | 2.6 | 0.32 |
| 498 | 2.5 | 1.1 | 2.2 |
| 508 | 9.4 | 7.7 | 8.1 |

The above test compounds showed high binding affinities (antagonism or inverse agonist action) for serotonin 5-HT$_{2A}$ receptor, serotonin 5-HT$_{2C}$ receptor, and serotonin transporter (SERT).

(4) Dopamine D$_{2L}$ Receptor Binding Test

The human D$_{2L}$ receptor binding activity of [$^3$H]-spiperone was determined as follows.

A solution containing 50 μL of [$^3$H]-spiperone (the final concentration: 0.5 nmol/L), 2 μL of a solution of a test compound in DMSO or a solvent (DMSO), and 148 μL of human D$_{2L}$ receptor-expressed CHO cell membrane sample was reacted in a 50 mmol/L Tris-HCl (pH=7.6) buffer, and then was let stand at room temperature for 60 minutes. Then, the resultant was added promptly to a glass fiber filter plate (Multiscreen FB, Millipore) coated with 0.3% polyethyleneimine (PEI) and filtered under reduced pressure. The filtered substance on the glass fiber filter was washed with 200 μL of ice-cooled 50 mmol/L Tris-HCl (pH=7.6) twice and repeated to be filtered under reduced pressure, followed by transfer to a vial containing 2 mL of Ecoscint A (National Diagnostics). The radioactivity of the filtered substance remained on the glass fiber filter was measured by liquid scintillation counter. The radioactivity value measured by liquid scintillation counter was deemed to be a receptor binding activity, and the binding inhibition was calculated from the total binding (TB), non-specific binding (NSB), and specific binding (SB) of a test drug according to the following equations.

Total binding (TB)=Radioactivity of a solvent-added group

Non-specific binding (NSB)=Radioactivity of the spiperone solution-added group

Specific binding (SB)=Radioactivity of the test compound solution-added group−NSB Binding inhibition (%)=SB/(TB−NSB)×100

Non-specific binding was measured in the presence of 10 μmol/L of spiperone solution, and [$^3$H]-spiperone binding inhibition (%) was calculated in 10 nmol/L of a test drug.

Based on the calculated binding inhibition (%), the IC$_{50}$ value was calculated according to Hill analysis (Hill A. V., J. Physiol., 40, 190-200 (1910)). When the binding inhibition was lower than 50% in the maximum evaluation concentration of a test compound (1 μmol/L or 10 μmol/L), the calculation of IC$_{50}$ value by Hill analysis was impossible and the IC$_{50}$ value was deemed to be >the maximum concentration. The higher the IC$_{50}$ value for human D$_{2L}$ receptor is, the weaker the binding affinity for human D$_{2L}$ receptor is. The results are shown in Table 2.

TABLE 2

| Example | D$_{2L}$ receptor IC$_{50}$ value (nmol/L) |
| --- | --- |
| 275 | >1000 |
| 283 | >1000 |
| 485 | >1000 |
| 500 | >1000 |
| 504 | >1000 |

The above test compounds did not show the binding affinity for dopamine D$_2$ receptor.

Test 2: Rat Tryptamine-Induced Forelimb Clonic Convulsion Model for Evaluation of In Vivo Serotonin 5-HT$_{2A}$ Receptor Antagonism Evaluation was conducted in a rodent tryptamine-induced forelimb clonic convulsion model which has been known as one of the methods for assessing the serotonin 5-HT$_{2A}$ receptor antagonism in vivo. The evaluation is to demonstrate that a test compound has serotonin 5-HT$_{2A}$ receptor antagonism when convulsion induced by serotonin 5-HT$_{2A}$ receptor-agonistic action is inhibited.

<Methods>

Seven-week-old SD-male rats were used. A dose solution for a test compound was prepared with 0.5% methylcellulose solution or saline for a solvent. A test compound was used in the form of a dose solution obtained by mixing with 0.5% methylcellulose solution to get cloudy (for oral administration) or dissolving in saline (for subcutaneous administration). Tryptamine was used and dissolved in saline as a substance inducing clonic convulsion.

A dose solution of a test compound or a solvent only was administered orally or subcutaneously to rats at the start of the test, and after 60 minutes of the administration, a saline solution containing tryptamine 25 mg/kg was administered intravenously to rats. Rats were transferred to an observation cage right after the administration of tryptamine, and their forelimb clonic convulsion was evaluated for 3 minutes. The forelimb clonic convulsion was evaluated according to the scores shown in Table 3.

TABLE 3

| Evaluation score for forelimb clonic convulsion | |
| --- | --- |
| Score | Symptoms |
| 0 | No observation of forelimb clonic convulsion. |
| 1 | Forelimb clonic convulsion was observed, but was not observed in both forelimbs at the same time, or bilateral forelimb clonic convulsion was terminated instantaneously. |
| 2 | Forelimb clonic convulsion continuing within less than 10 seconds was observed in both forelimbs at the same time. |
| 3 | Forelimb clonic convulsion continuing for 10 seconds or more was observed in both forelimbs at the same time. |

The average inhibition ratio of each individual calculated from the following equation was deemed to be the inhibition ratio of each administration group.

Inhibition ratio of each individual=(Average score of the solvent-administered group−Score of each individual)/Average score of the solvent-administered group×100

Statistical analysis of the test results was conducted by the following procedures with Stat Preclinica (Takumi Information Technology):

1) Jonckheere-Terpstra test was conducted in the solvent-administered group and test compound-administered group with the forelimb clonic convulsion score as indicator. A method option was approximation test with the significance level of 5% for both sides. A significant difference was deemed to be dosage dependence, and the analysis in 2) was conducted.

2) Non-parametric Dunnett's multiple comparison (Joint Ranking)-measured value was conducted between the solvent-administered group and test compound-administered group with the forelimb clonic convulsion score as indicator. The significance level was 5% for both sides. Significant reduction of score in any of doses in the test compound-administered group was considered that a test compound has $5\text{-}HT_{2A}$ receptor antagonism. The results are shown in Table 4.

TABLE 4

| Test compound | Dose | Inhibition ratio |
| --- | --- | --- |
| Pimavanserin | 1 mg/kg | 13% |
| | 3 mg/kg | 38% |
| | 10 mg/kg | 75%** |
| Example 147 | 1 mg/kg | 46% |
| | 3 mg/kg | 46% |
| | 10 mg/kg | 71%** |
| Example 502 | 10 mg/kg | 45%* |
| | 20 mg/kg | 65%** |
| | 30 mg/kg | 84%** |

*P < 0.05,
**P < 0.01
(Non-parametric Dunnett's multiple comparison test)

In Test 2, the test compounds were confirmed to show the $5\text{-}HT_{2A}$ receptor antagonism in vivo as observed for pimavanserin used for treatment of psychopathic symptoms.

Test 3: Rat-forced swimming test for evaluation of the antidepressant effect

A rat-forced swimming test, commonly used as one of the evaluation systems for the antidepressant effect, was conducted. In this test, a tricyclyl antidepressant, nortriptyline, which was confirmed to ameliorate depressive symptoms in Parkinson's disease has been reported to have the antidepressant effect (Non Patent Literature 18 and Non Patent Literature 19).

<Methods>

Eight-week-old Wistar-male rats were used. Dose solutions for a test compound and positive control compound, imipramine, were prepared with 0.5% methylcellulose solution for a solvent and used after mixing to get cloudy.

The forced swimming test was conducted as follows with a transparent plastic water tank filled with 5.8 L of tap water at 25° C. of a water temperature.

Specifically, on day 1 a swimming training was conducted by transferring animals into the water tank and forcing them to swim for 15 minutes. After the swimming training, the animals were wiped promptly to remove waterdrops adhered to them and brought back to a home cage, and 15 minutes after the training, a dose solution (solvent only, a positive control compound, or a test compound) was administered orally. On the next day or the day after next oral administration once per day only was conducted, and on day 4 a swimming test was conducted. The swimming test was conducted by forcing to swim in the water tank for 5 minutes after oral administration of a dose solution 1 hour before start of the test. Swimming behavior of each individual was videotaped from a side surface of the water tank, and immobility time was measured with a stopwatch. The immobility refers to the state of being suspended without moving the forelimbs or trunk in the water tank and is deemed to include slight actions required to remain suspended. The cumulative time of showing immobility was determined to be the immobility time for an individual.

The test results were analyzed as follows.

Specifically, parametric Dunnett's multiple comparison (significance level: two-sided 5%) was conducted for a test compound-administered group and solvent-administered group. When the test compound-administered group showed a significant reduction of the immobility time compared to the solvent-administered group, the test compound was determined to have the antidepressant effect. The results are shown in FIG. 1 and FIG. 2.

Test 4: Rat Social Interaction Evaluation on the Anxiolytic Effect

Rat social interaction evaluation, commonly used as one of the behavioral pharmacological tests of evaluation for the anxiolytic effect, was conducted. In this evaluation, a benzodiazepine anxiolytic drug, benzodiazepine, used in the treatment of anxiety symptoms in Parkinson's disease has been reported to have the efficacy (Non Patent Literature 20).

<Methods>

Seven-week old SD-male rats were used. Dose solutions for a test compound and positive control compound, diazepam, were prepared with 0.5% methylcellulose solution for a solvent and used after mixing to get cloudy.

The rat social interaction was evaluated with the anxiety state under a novel environment in an observation box (acrylic; wrapped a side surface up in black paper to be masked). The test was conducted as follows.

Specifically, on the day before the test, each individual had its body weight measured and was allocated into each administration group with "blocked allocation by one variable" of statistical analysis software (Stat Preclinica: Takumi Information Technology) with the average body weight of each cage as indicator.

On the test day, a dose solution (solvent only, diazepam, or a test compound) was administered orally to an administration group 1 hour before start of the test, and then one animal was transferred from each of two cages of the same administration group to an observation box with 200 1x of the illuminance. Behavior of each animal was videotaped for 10 minutes in the observation box, and social interaction behavior time was measured with a stopwatch. The social interaction behavior refers to sniffing partner, mutual grooming, crawling under and climbing over partner, following and walking around partner, and genital investigation, and the cumulative time of showing these behavior was determined to be the social interaction time for an individual.

The test results were analyzed by parametric Dunnett's multiple comparison (significance level: two-sided 5%). When the test compound-administered group showed a significant increase of the social interaction time compared to the solvent-administered group, the test compound was determined to have the anxiolytic effect. The results are shown in FIG. 3 to FIG. 6.

In Tests 3 and 4, the test compounds were confirmed to show the efficacy comparable to the existing antidepressants or anxiolytic drugs in the forced swimming test and social interaction evaluation commonly used for evaluation of the antidepressant effect and anxiolytic effect.

Test 5: Clinical Trial Evaluation of Psychopathic Symptoms and Depressive Symptoms in Parkinson's Disease The following clinical trial can confirm that the present compound is useful for psychopathic symptoms or depressive symptoms in Parkinson's disease. Clinical evaluation of psychopathic symptoms and depressive symptoms are illustrated as an example, and other non-motor symptoms can also be evaluated in a similar manner.

(1) Evaluation of Psychopathic Symptoms Based on the Scale for Assessment of Symptoms or Image Diagnostic Indicator Patients diagnosed as Parkinson's disease and having psychopathic symptoms (such as hallucination and delusion) are targeted. A test compound is administered to the patients once or several times (regardless of the number of doses a day). Psychopathic symptoms are evaluated on the basis of an appropriate scale for assessment of symptoms before and after start of the administration, and the efficacy of the present compound on psychopathic symptoms in Parkinson's disease can be determined if the score decreases compared to that before the administration. The efficacy of the present compound can also be determined if the amount of change of the scale is larger in the present compound than that in a control drug in a controlled study with a placebo or drug with similar drug efficacy.

The scale for assessment of psychopathic symptoms in Parkinson's disease includes, for example, clinical global impressions (CGI) and associated indicators thereof, the scale for assessment of positive symptoms-Parkinson's disease scale (SAPS-PD) or scale for assessment of positive symptoms (SAPS), and the whole or a part of Neuropsychiatric Inventory (NPI) (e.g., psychotic scores (Delusions [Domain A]+Hallucinations [Domain B])). The efficacy can also be determined on the basis of the change on an image in the region of interests (ROI) by image diagnostic indicator such as optical topography (near-infrared spectroscopy, NIRS) and functional magnetic resonance imaging (fMRI).

(2) Evaluation of Depressive Symptoms Based on the Scale for Assessment of Symptoms or Image Diagnostic Indicator Patients diagnosed as Parkinson's disease and having depressive symptoms are targeted. A test compound is administered to the patients once or several times (regardless of the number of doses a day). Depressive symptoms are evaluated on the basis of an appropriate scale for assessment of symptoms before and after start of the administration, and the efficacy of the present compound on depressive symptoms in Parkinson's disease can be determined if the score decreases compared to that before the administration. The efficacy of the present compound can also be determined if the amount of change of the scale is larger in the present compound than that in a control drug in a controlled study with a placebo or drug with similar drug efficacy.

The scale for assessment of depressive symptoms in Parkinson's disease includes, for example, CGI and associated indicators thereof, Montgomery-Asberg depression scale (MADRS) or Hamilton depression scale (HAM-D), and the whole or a part of NPI (e.g., depression scores). The efficacy can also be determined on the basis of the change on an image in the ROI by image diagnostic indicator such as NIRS and fMRI.

Test 6: Clinical Trial Evaluation of Psychopathic Symptoms, Depressive Symptoms, and Agitation Symptoms in Alzheimer Disease The following clinical trial can confirm that the present compound is useful for psychopathic symptoms, depressive symptoms, or agitation symptoms in Alzheimer disease. Clinical evaluation of psychopathic symptoms, depressive symptoms, and agitation symptoms are illustrated as an example, and other non-motor symptoms can also be evaluated in a similar manner.

(1) Evaluation of Psychopathic Symptoms Based on the Scale for Assessment of Symptoms or Image Diagnostic Indicator Patients diagnosed as Alzheimer disease and having psychopathic symptoms are targeted. A test compound is administered to the patients once or several times (regardless of the number of doses a day). Psychopathic symptoms are evaluated on the basis of an appropriate scale for assessment of symptoms before and after start of the administration, and the efficacy of the present compound on psychopathic symptoms in Alzheimer disease can be determined if the score decreases compared to that before the administration. The efficacy of the present compound can also be determined if the amount of change of the scale is larger in the present compound than that in a control drug in a controlled study with a placebo or drug with similar drug efficacy.

The scale for assessment of psychopathic symptoms in Alzheimer disease includes, for example, CGI and associated indicators thereof, and the whole or a part of NPI (e.g., psychotic scores (Delusions [Domain A]+Hallucinations [Domain B])). The scale for assessment such as SAPS, positive and negative symptom scale (PANSS), and brief psychiatric rating scale (BPRS) can also be used depending on the conditions of patients. The efficacy can also be determined on the basis of the change on an image in the ROI by image diagnostic indicator such as NIRS and fMRI.

(2) Evaluation of Depressive Symptoms Based on the Scale for Assessment of Symptoms or Image Diagnostic Indicator Patients diagnosed as Alzheimer disease and having depressive symptoms are targeted. A test compound is administered to the patients once or several times (regardless of the number of doses a day). Depressive symptoms are evaluated on the basis of an appropriate scale for assessment of symptoms before and after start of the administration, and the efficacy of the present compound on depressive symptoms in Alzheimer disease can be determined if the score decreases compared to that before the administration. The efficacy of the present compound can also be determined if the amount of change of the scale is larger in the present compound than that in a control drug in a controlled study with a placebo or drug with similar drug efficacy.

The scale for assessment of depressive symptoms in Alzheimer disease includes, for example, CGI and associated indicators thereof, Cornell Scale for Depression in Dementia (CSDD), and the whole or a part of NPI (depression scores). The scale for assessment such as MADRS and HAM-D can also be used depending on the conditions of patients. The efficacy can also be determined on the basis of the change on an image in the ROI by image diagnostic indicator such as NIRS and fMRI.

(3) Evaluation of Agitation Symptoms Based on the Scale for Assessment of Symptoms or Image Diagnostic Indicator Patients diagnosed as Alzheimer disease and having agitation symptoms are targeted. A test compound is administered to the patients once or several times (regardless of the number of doses a day). Agitation symptoms are evaluated on the basis of an appropriate scale for assessment of symptoms before and after start of the administration, and the efficacy of the present compound on agitation symptoms in Alzheimer disease can be determined if the score decreases compared to that before the administration. The efficacy of the present compound can also be determined if the amount of change of the scale is larger in the present compound than that in a control drug in a controlled study with a placebo or drug with similar drug efficacy.

The scale for assessment of agitation symptoms in Alzheimer disease includes, for example, CGI and associated indicators thereof, Cohen-Mansfield Agitation Inventory (CMAI), and the whole or a part of NPI. The efficacy can also be determined on the basis of the change on an image in the ROI by image diagnostic indicator such as NIRS and fMRI.

INDUSTRIAL APPLICABILITY

The present compound can exert potent efficacy on psychopathic symptoms in Parkinson's disease and other non-motor symptoms to provide improvement of life quality in Parkinson's disease patients and decrease of caregiver burden.

The invention claimed is:
1. A method for treating a non-motor symptom associated with Parkinson's disease or preventing a relapse thereof, wherein the non-motor symptom associated with Parkinson's disease is a psychopathic symptom or cognitive dysfunction, the method comprising administering a therapeutically effective amount of a compound of Formula (1),

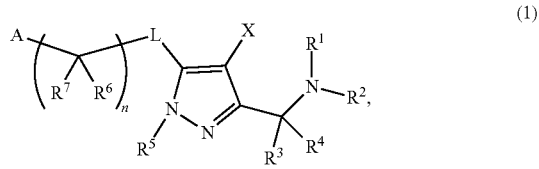

(1)

wherein:
$R^1$ and $R^2$ are each independently hydrogen atom, a $C_{1-6}$ alkyl group optionally substituted with 1 to 3 deuterium atoms, or a $C_{3-8}$ cycloalkyl group,
$R^3$ and $R^4$ are each independently hydrogen atom, deuterium atom, or a $C_{1-6}$ alkyl group,
$R^5$ is an optionally-substituted $C_{4-7}$ alkyl group or $—(CR^8R^9)_r$-E,
$R^6$ and $R^7$ are each independently hydrogen atom, deuterium atom, fluorine atom, or an optionally-substituted $C_{1-6}$ alkyl group,
$R^8$ and $R^9$ are each independently hydrogen atom, fluorine atom, or an optionally-substituted $C_{1-6}$ alkyl group,
A is an optionally-substituted $C_{6-10}$ aryl group or an optionally-substituted 5- to 10-membered heteroaryl group,
r is 1, 2, 3, or 4,
E is an optionally-substituted $C_{3-8}$ cycloalkyl group, an optionally-substituted $C_{4-8}$ cycloalkenyl group, an optionally-substituted 5- to 10-membered saturated heterocyclic group wherein the saturated heterocyclic group comprises 1 to 3 heteroatoms independently selected from the group consisting of oxygen atom and sulfur atom as a constituent atom of the ring, an optionally-substituted $C_{6-10}$ aryl group, or an optionally-substituted 5- to 10-membered heteroaryl group,
L is oxygen atom, sulfur atom, or $—NR^{10}—$,
n is 1, 2, or 3,
$R^{10}$ is hydrogen atom, a $C_{1-6}$ alkyl group, or a $C_{3-8}$ cycloalkyl group, X is hydrogen atom, a $C_{1-6}$ alkyl group optionally substituted with fluorine atom, or a halogen atom,
a substituent on the optionally-substituted $C_{6-10}$ aryl group and optionally-substituted 5- to 10-membered heteroaryl group is 1 to 2 substituents each independently selected from the group consisting of a halogen atom; a $C_{1-6}$ alkyl group optionally substituted with fluorine atom; a $C_{1-6}$ alkyloxy group optionally substituted with fluorine atom; hydroxy group; a $C_{1-6}$ alkylthio group; a $C_{6-10}$ aryloxy group; a $C_{6-10}$ arylthio group; cyano group; $—CO_2R^{11}$; $—SO_2R^{11}$; $—NR^{10}SO_2R^{11}$; $—OSO_2R^{11}$; $—COR^{12}$; $—SO_2NR^{12}R^{13}$; $—CONR^{12}R^{13}$; $—NR^{12}R^{13}$; $—NR^{10}CONR^{12}R^{13}$; $—NR^{10}COR^{12}$; $—CR^{12}=N(OR^{11})$; oxime group; a $C_{3-8}$ cycloalkyl group; a $C_{6-10}$ aryl group; and a 5- to 10-membered heteroaryl group, wherein $R^{10}$ is as defined above, $R^{11}$ is a $C_{1-6}$ alkyl group, a $C_{3-8}$ cycloalkyl group, a $C_{6-10}$ aryl group, or a 5- to 10-membered heteroaryl group, $R^{12}$ and $R^{13}$ are each independently hydrogen atom, a $C_{1-6}$ alkyl group, a $C_{3-8}$ cycloalkyl group, a $C_{6-10}$ aryl group, or a 5- to 10-membered heteroaryl group, and the $C_{6-10}$ aryl group and 5- to 10-membered heteroaryl group in $R^{11}$, $R^{12}$, and $R^{13}$ may be optionally further substituted with a halogen atom, a $C_{1-6}$ alkyl group, hydroxy group, or a $C_{1-6}$ alkyloxy group,
a substituent on the optionally-substituted $C_{1-6}$ alkyl group and optionally-substituted $C_{4-7}$ alkyl group is 1 to 2 substituents each independently selected from the group consisting of fluorine atom; hydroxy group; and a $C_{1-6}$ alkyloxy group optionally substituted with fluorine atom, and
a substituent on the optionally-substituted $C_{3-8}$ cycloalkyl group, optionally-substituted $C_{4-8}$ cycloalkenyl group, and optionally-substituted 5- to 10-membered saturated heterocyclic group is 1 to 2 substituents each independently selected from the group consisting of fluorine atom; a $C_{1-6}$ alkyl group optionally substituted with fluorine atom; hydroxy group; and a $C_{1-6}$ alkyloxy group optionally substituted with fluorine atom,
or a pharmaceutically acceptable salt thereof, to a patient in need thereof.

2. The method according to claim 1, wherein $R^1$ and $R^2$ are each independently hydrogen atom, methyl group, or methyl group substituted with 1 to 3 deuterium atoms, $R^3$ is hydrogen atom, deuterium atom, or methyl group, and $R^4$ is hydrogen atom or deuterium atom.

3. The method according to claim 1, wherein A is an optionally-substituted $C_{6-10}$ aryl group.

4. The method according to claim 1, wherein X is hydrogen atom.

5. The method according to claim 1, wherein L is oxygen atom.

6. The method according to claim 1, wherein n is 1.

7. The method according to claim 1, wherein $R^1$, $R^3$, and $R^4$ are hydrogen atom and $R^2$ is methyl group.

8. The method according to claim 1, wherein $R^6$ and $R^7$ are each independently hydrogen atom or deuterium atom and $R^8$ and $R^9$ are hydrogen atom.

9. The method according to claim 1, wherein E is an optionally-substituted $C_{3-8}$ cycloalkyl group, an optionally-substituted 5- to 10-membered saturated heterocyclic group wherein the saturated heterocyclic group comprises 1 to 3 oxygen atoms as a constituent atom of the ring, or an optionally-substituted phenyl group.

10. The method according to claim 1, wherein E is an optionally-substituted $C_{3-8}$ cycloalkyl group.

11. The method according to claim 1, wherein r is 1 or 2.

12. The method according to claim 1, wherein $R^5$ is an optionally-substituted $C_{4-7}$ alkyl group.

13. The method according to claim 1, wherein the compound of Formula (1) is at least one selected from the group consisting of:

1-[5-(benzyloxy)-1-(cyclohexylmethyl)-1H-pyrazol-3-yl]-N-methylmethanamine;
1-{1-(cyclohexylmethyl)-5-[(2-fluorobenzyl)oxy]-1H-pyrazol-3-yl}-N-methylmethanamine;
1-{5-[(2-chloro-4-fluorobenzyl)oxy]-1-(cyclohexylmethyl)-1H-pyrazol-3-yl}-N-methylmethanamine;
1-{1-(cyclohexylmethyl)-5-[(4-fluoro-2-methylbenzyl)oxy]-1H-pyrazol-3-yl}-N-methylmethanamine;
1-{1-(cyclohexylmethyl)-5-[(2,5-difluorobenzyl)oxy]-1H-pyrazol-3-yl}-N-methylmethanamine;
1-{5-[(5-chloro-2-fluorobenzyl)oxy]-1-(cyclohexylmethyl)-1H-pyrazol-3-yl}-N-methylmethanamine;
1-{5-[(2-chloro-5-fluorobenzyl)oxy]-1-(cyclohexylmethyl)-1H-pyrazol-3-yl}-N-methylmethanamine;
1-{1-(cyclohexylmethyl)-5-[(2,5-dichlorobenzyl)oxy]-1H-pyrazol-3-yl}-N-methylmethanamine;
1-{1-(cyclopentylmethyl)-5-[(4-fluorobenzyl)oxy]-1H-pyrazol-3-yl}-N-methylmethanamine;
1-{5-[(2-chlorobenzyl)oxy]-1-(cyclopentylmethyl)-1H-pyrazol-3-yl}-N-methylmethanamine;
1-{1-(cyclopentylmethyl)-5-[(2,4-difluorobenzyl)oxy]-1H-pyrazol-3-yl}-N-methylmethanamine;
1-{1-(cyclopentylmethyl)-5-[(2,5-difluorobenzyl)oxy]-1H-pyrazol-3-yl}-N-methylmethanamine;
1-{5-[(5-chloro-2-fluorobenzyl)oxy]-1-(cyclopentylmethyl)-1H-pyrazol-3-yl}-N-methylmethanamine;
1-{5-[(2,5-difluorobenzyl)oxy]-1-(3,3-dimethylbutyl)-1H-pyrazol-3-yl}-N-methylmethanamine;
1-{5-[(2,5-difluorobenzyl)oxy]-1-(3-methylbutyl)-1H-pyrazol-3-yl}-N-methylmethanamine;
1-{5-[(5-chloro-2-fluorobenzyl)oxy]-1-(3-methoxy-3-methylbutyl)-1H-pyrazol-3-yl}-N-methylmethanamine;
1-{1-(cyclopentylmethyl)-5-[(2,4,5-trifluorobenzyl)oxy]-1H-pyrazol-3-yl}-N-methylmethanamine;
1-{1-(2-cyclopentylethyl)-5-[(2,5-difluorobenzyl)oxy]-1H-pyrazol-3-yl}-N-methylmethanamine;
N-methyl-1-{1-(3-methylbutyl)-5-[(2,4,5-trifluorobenzyl)oxy]-1H-pyrazol-3-yl}-methylmethanamine;
1-{1-(3,3-dimethylbutyl)-5-[(2,4,5-trifluorobenzyl)oxy]-1H-pyrazol-3-yl}-N-methylmethanamine;
1-{1-(4-fluorobenzyl)-5-[(2-fluorobenzyl)oxy]-1H-pyrazol-3-yl}-N-methylmethanamine;
1-{5-[(2,5-difluorobenzyl)oxy]-1-(4-fluorobenzyl)-1H-pyrazol-3-yl}-N-methylmethanamine;
1-{5-[(2,5-difluorobenzyl)oxy]-1-(4-methylbenzyl)-1H-pyrazol-3-yl}-N-methylmethanamine;
N-methyl-1-{1-(4-methylbenzyl)-5-[(2,4,5-trifluorobenzyl)oxy]-1H-pyrazol-3-yl}methanamine;
1-{5-[(5-chloro-2-fluorobenzyl)oxy]-1-(cyclopropylmethyl)-1H-pyrazol-3-yl}-N-methylmethanamine;
1-{5-[(5-chloro-2-fluorobenzyl)oxy]-1-(2-methylpropyl)-1H-pyrazol-3-yl}-N-methylmethanamine;
1-{5-[(2,5-difluorobenzyl)oxy]-1-(2,2-dimethylpropyl)-1H-pyrazol-3-yl}-N-methylmethanamine;
1-{5-[(5-chloro-2-fluorobenzyl)oxy]-1-(2,2-dimethylpropyl)-1H-pyrazol-3-yl}-N-methylmethanamine;
1-[1-benzyl-5-(benzyloxy)-1H-pyrazol-3-yl]-N-methylmethanamine;
1-{5-[(4-fluoro-2-methylbenzyl)oxy]-1-(tetrahydro-2H-pyran-2-ylmethyl)-1H-pyrazolo-3-yl}-N-methylmethanamine;
1-[5-(benzyloxy)-1-(bicyclo[2.2.1]hept-2-ylmethyl)-1H-pyrazol-3-yl]-N-methylmethanamine;
1-{1-(bicyclo[2,2,1]hept-2-ylmethyl)-5-[(2,5-difluorobenzyl)oxy]-1H-pyrazol-3-yl}-N-methylmethanamine;
1-{1-(bicyclo[2,2,1]hept-2-ylmethyl)-5-[(5-chloro-2-fluorobenzyl)oxy]-1H-pyrazol-3-yl}-N-methylmethanamine;
1-{5-[(3-chlorobenzyl)oxy]-1-(2-oxabicyclo[2,2,2]oct-3-ylmethyl)-1H-pyrazol-3-yl}-N-methylmethanamine;
1-{5-[(2,5-difluorobenzyl)oxy]-1-[(4,4-difluorocyclohexyl)methyl]-1H-pyrazol-3-yl}-N-methylmethanamine;
1-{5-[(2,5-difluorobenzyl)oxy]-1-[(1-fluorocyclohexyl)methyl]-1H-pyrazol-3-yl}-N-methylmethanamine;
2-[({1-(cyclopentylmethyl)-3-[(methylamino)methyl]-1H-pyrazol-5-yl}oxy)methyl]benzonitrile;
1-{1-(4-chlorobenzyl)-5-[(2,5-difluorobenzyl)oxy]-1H-pyrazol-3-yl}-N-methylmethanamine;
1-{5-[(5-chloro-2-fluorobenzyl)oxy]-1-(2-ethylbutyl)-1H-pyrazol-3-yl}-N-methylmethanamine;
1-[5-(benzyloxy)-1-(1-cyclopentylethyl)-1H-pyrazol-3-yl]-N-methylmethanamine;
1-{5-[(5-chloro-2-fluorobenzyl)oxy]-1-(1-cyclopentylethyl)-1H-pyrazol-3-yl}-N-methylmethanamine;
1-[5-(benzyloxy)-1-(1-cyclohexylethyl)-1H-pyrazol-3-yl]-N-methylmethanamine;
1-{1-(1-cyclohexylethyl)-5-[(2-fluorobenzyl)oxy]-1H-pyrazol-3-yl}-N-methylmethanamine;
1-{1-(1-cyclohexylethyl)-5-[(4-fluorobenzyl)oxy]-1H-pyrazol-3-yl}-N-methylmethanamine;
1-{5-[(2-chlorobenzyl)oxy]-1-(1-cyclohexylethyl)-1H-pyrazol-3-yl}-N-methylmethanamine;
1-{1-(1-cyclohexylethyl)-5-[(2-methylbenzyl)oxy]-1H-pyrazol-3-yl}-N-methylmethanamine;
1-{1-(1-cyclohexylethyl)-5-[(3-methylbenzyl)oxy]-1H-pyrazol-3-yl}-N-methylmethanamine;
1-{1-(1-cyclohexylethyl)-5-[(2,4-difluorobenzyl)oxy]-1H-pyrazol-3-yl}-N-methylmethanamine;
1-{5-[(2-chloro-4-fluorobenzyl)oxy]-1-(1-cyclohexylethyl)-1H-pyrazol-3-yl}-N-methylmethanamine;
1-{1-(1-cyclohexylethyl)-5-[(4-fluoro-2-methylbenzyl)oxy]-1H-pyrazol-3-yl}-N-methylmethanamine;
1-{1-(1-cyclohexylethyl)-5-[(2,5-difluorobenzyl)oxy]-1H-pyrazol-3-yl}-N-methylmethanamine;
1-{5-[(5-chloro-2-fluorobenzyl)oxy]-1-(1-cyclohexylethyl)-1H-pyrazol-3-yl}-N-methylmethanamine;
1-{1-(1-cyclohexylethyl)-5-[(2-fluoro-5-methylbenzyl)oxy]-1H-pyrazol-3-yl}-N-methylmethanamine;
1-[5-(benzyloxy)-1-(1-cyclohexyl-2-fluoroethyl)-1H-pyrazol-3-yl]-N-methylmethanamine;
1-{5-(benzyloxy)-1-[(1-methylcyclohexyl)methyl]-1H-pyrazol-3-yl}-N-methylmethanamine;
1-{5-[(3-chlorobenzyl)oxy]-1-(3,4-dihydro-2H-chromen-2-ylmethyl)-1H-pyrazol-3-yl}-N-methylmethanamine;
N-({1-(cyclohexylmethyl)-5-[(2,5-difluorobenzyl)oxy]-1H-pyrazol-3-yl}methyl)cyclopropanamine;
N-({1-(cyclohexylmethyl)-5-[(2,5-difluorobenzyl)oxy]-1H-pyrazol-3-yl}methyl)ethanamine;
1-{1-(cyclohexylmethyl)-5-[(2,5-difluorobenzyl)oxy]-1H-pyrazol-3-yl}methanamine;
1-{1-(cyclohexylmethyl)-5-[difluoro(phenyl)methoxy]-1H-pyrazol-3-yl}-N-methylmethanamine;

1-[5-(benzyloxy)-1-(cyclohexylmethyl)-1H-pyrazol-3-yl]-N-methyl($^2$H$_2$)methanamine;
1-[5-(benzyloxy)-1-(cyclohexylmethyl)-1H-pyrazol-3-yl]-N-($^2$H$_3$)methyl($^2$H$_2$)methanamine;
1-[5-(benzyloxy)-1-(cyclohexylmethyl)-1H-pyrazol-3-yl]-N-($^2$H$_3$)methylmethanamine;
1-[1-(cyclopentylmethyl)-5-{[(2,5-difluorophenyl)($^2$H$_2$)methyl]oxy}-1H-pyrazol-3-yl]-N-methylmethanamine;
1-[5-{[(5-chloro-2-fluorophenyl)($^2$H$_2$)methyl]oxy}-1-(cyclopentylmethyl)-1H-pyrazol-3-yl]-N-methylmethanamine;
1-[1-(cyclohexylmethyl)-5-{[(2,5-difluorophenyl)($^2$H$_2$)methyl]oxy}-1H-pyrazol-3-yl]-N-methylmethanamine;
1-[5-{[(5-chloro-2-fluorophenyl)($^2$H$_2$)methyl]oxy}-1-(cyclohexylmethyl)-1H-pyrazol-3-yl]-N-methylmethanamine; and
1-[5-{[(2,5-difluorophenyl)($^2$H$_2$)methyl]oxy}-1-(3,3-dimethylbutyl)-1H-pyrazol-3-yl]-N-methyl($^2$H$_2$)methanamine,
or a pharmaceutically acceptable salt thereof.

14. The method according to claim 1, wherein the non-motor symptom associated with Parkinson's disease is cognitive dysfunction.

15. The method according to claim 1, wherein the non-motor symptom associated with Parkinson's disease is a psychopathic symptom.

16. A method for antagonizing a serotonin 5-HT$_{2A}$ receptor, inhibiting a serotonin transporter, and antagonizing a serotonin 5-HT$_{2C}$ receptor, comprising administering a therapeutically effective amount of a compound of Formula (1)

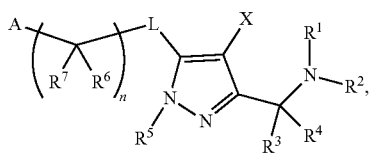

(1)

wherein:
R$^1$ and R$^2$ are each independently hydrogen atom, a C$_{1-6}$ alkyl group optionally substituted with 1 to 3 deuterium atoms, or a C$_{3-8}$ cycloalkyl group,
R$^3$ and R$^4$ are each independently hydrogen atom, deuterium atom, or a C$_{1-6}$ alkyl group,
R$^5$ is an optionally-substituted C$_{4-7}$ alkyl group or —(CR$^8$R$^9$)$_r$-E,
R$^6$ and R$^7$ are each independently hydrogen atom, deuterium atom, fluorine atom, or an optionally-substituted C$_{1-6}$ alkyl group,
R$^8$ and R$^9$ are each independently hydrogen atom, fluorine atom, or an optionally-substituted C$_{1-6}$ alkyl group,
A is an optionally-substituted C$_{6-10}$ aryl group or an optionally-substituted 5- to 10-membered heteroaryl group,
r is 1, 2, 3, or 4,
E is an optionally-substituted C$_{3-8}$ cycloalkyl group, an optionally-substituted C$_{4-8}$ cycloalkenyl group, an optionally-substituted 5- to 10-membered saturated heterocyclic group wherein the saturated heterocyclic group comprises 1 to 3 heteroatoms independently selected from the group consisting of oxygen atom and sulfur atom as a constituent atom of the ring, an optionally-substituted C$_{6-10}$ aryl group, or an optionally-substituted 5- to 10-membered heteroaryl group,
L is oxygen atom, sulfur atom, or —NR$^{10}$—,
n is 1, 2, or 3,
R$^{10}$ is hydrogen atom, a C$_{1-6}$ alkyl group, or a C$_{3-8}$ cycloalkyl group,
X is hydrogen atom, a C$_{1-6}$ alkyl group optionally substituted with fluorine atom, or a halogen atom,
a substituent on the optionally-substituted C$_{6-10}$ aryl group and optionally-substituted 5- to 10-membered heteroaryl group is 1 to 2 substituents each independently selected from the group consisting of a halogen atom; a C$_{1-6}$ alkyl group optionally substituted with fluorine atom; a C$_{1-6}$ alkyloxy group optionally substituted with fluorine atom; hydroxy group; a C$_{1-6}$ alkylthio group; a C$_{6-10}$ aryloxy group; a C$_{6-10}$ arylthio group; cyano group; —CO$_2$R$^{11}$; —SO$_2$R$^{11}$; —NR$^{10}$SO$_2$R$^{11}$; —OSO$_2$R$^{11}$; —COR$^{12}$; —SO$_2$NR$^{12}$R$^{12}$; —CONR$^{12}$R$^{13}$; —NR$^{12}$R$^{13}$; —NR$^{10}$CONR$^{12}$R$^{13}$; —NR$^{10}$COR$^{12}$; —CR$^{12}$=N(OR$^{11}$); oxime group; a C$_{3-8}$ cycloalkyl group; a C$_{6-10}$ aryl group; and a 5- to 10-membered heteroaryl group, wherein R$^{10}$ is as defined above, R$^{11}$ is a C$_{1-6}$ alkyl group, a C$_{3-8}$ cycloalkyl group, a C$_{6-10}$ aryl group, or a 5- to 10-membered heteroaryl group, R$^{12}$ and R$^{13}$ are each independently hydrogen atom, a C$_{1-6}$ alkyl group, a C$_{3-8}$ cycloalkyl group, a C$_{6-10}$ aryl group, or a 5- to 10-membered heteroaryl group, and the C$_{6-10}$ aryl group and 5- to 10-membered heteroaryl group in R$^{11}$, R$^{12}$, and R$^{13}$ may be optionally further substituted with a halogen atom, a C$_{1-6}$ alkyl group, hydroxy group, or a C$_{1-6}$ alkyloxy group,
a substituent on the optionally-substituted C$_{1-6}$ alkyl group and optionally-substituted C$_{4-7}$ alkyl group is 1 to 2 substituents each independently selected from the group consisting of fluorine atom; hydroxy group; and a C$_{1-6}$ alkyloxy group optionally substituted with fluorine atom, and
a substituent on the optionally-substituted C$_{3-8}$ cycloalkyl group, optionally-substituted C$_{4-8}$ cycloalkenyl group, and optionally-substituted 5- to 10-membered saturated heterocyclic group is 1 to 2 substituents each independently selected from the group consisting of fluorine atom; a C$_{1-6}$ alkyl group optionally substituted with fluorine atom; hydroxy group; and a C$_{1-6}$ alkyloxy group optionally substituted with fluorine atom,
or a pharmaceutically acceptable salt thereof,
to a patient in need thereof.

17. The method according to claim 1, wherein the compound has the action of antagonizing a serotonin 5-HT$_{2A}$ receptor, inhibiting a serotonin transporter, and antagonizing a serotonin 5-HT$_{2C}$ receptor.

18. The method according to claim 1, wherein the compound is administered in combination with at least one medicament selected from the group consisting of an antidepressant, an anxiolytic drug, an antipsychotic agent, a dopamine replacement drug, a dopamine receptor agonist, an antiparkinsonian drug, an anti-epilepsy drug, an analgesic drug, a hormone preparation, an antimigraine drug, an adrenaline β receptor antagonist, an antidementia drug, a therapeutic drug for a mood disorder, an antiemetic drug, and a sleep-inducing drug, to the patient in need thereof.

19. The method according to claim 1, wherein the compound of Formula (1) is at least one selected from the group consisting of:
- 1-{1-(cyclopentylmethyl)-5-[(2,5-difluorobenzyl)oxy]-1H-pyrazol-3-yl}-N-methylmethanamine;
- 1-{5-[(2,5-difluorobenzyl)oxy]-1-(3,3-dimethylbutyl)-1H-pyrazol-3-yl}-N-methylmethanamine;
- N-methyl-1-{1-(3-methylbutyl)-5-[(2,4,5-trifluorobenzyl)oxy]-1H-pyrazol-3-yl}methanamine;
- 1-{5-[(5-chloro-2-fluorobenzyl)oxy]-1-(cyclopropylmethyl)-1H-pyrazol-3-yl}-N-methylmethanamine; and
- 1-{5-[(5-chloro-2-fluorobenzyl)oxy]-1-(2-methylpropyl)-1H-pyrazol-3-yl}-N-methylmethanamine, or a pharmaceutically acceptable salt thereof.

20. The method according to claim 1, wherein the compound of Formula (1) is 1-{1-(cyclopentylmethyl)-5-[(2,5-difluorobenzyl)oxy]-1H-pyrazol-3-yl}-N-methylmethanamine, or a pharmaceutically acceptable salt thereof.

21. The method according to claim 1, wherein the compound of Formula (1) is 1-{5-[(2,5-difluorobenzyl)oxy]-1-(3,3-dimethylbutyl)-1H-pyrazol-3-yl}-N-methylmethanamine, or a pharmaceutically acceptable salt thereof.

22. The method according to claim 1, wherein the compound of Formula (1) is N-methyl-1-{1-(3-methylbutyl)-5-[(2,4,5-trifluorobenzyl)oxy]-1H-pyrazol-3-yl}methanamine, or a pharmaceutically acceptable salt thereof.

23. The method according to claim 1, wherein the compound of Formula (1) is 1-{5-[(5-chloro-2-fluorobenzyl)oxy]-1-(cyclopropylmethyl)-1H-pyrazol-3-yl}-N-methylmethanamine, or a pharmaceutically acceptable salt thereof.

24. The method according to claim 1, wherein the compound of Formula (1) is 1-{5-[(5-chloro-2-fluorobenzyl)oxy]-1-(2-methylpropyl)-1H-pyrazol-3-yl}-N-methylmethanamine, or a pharmaceutically acceptable salt thereof.

* * * * *